United States Patent
Dyroff et al.

(10) Patent No.: US 12,251,382 B2
(45) Date of Patent: Mar. 18, 2025

(54) SUBSTITUTED AMINO-PYRIMIDINE COMPOUND FOR USE IN A METHOD FOR TREATMENT AND PREVENTION OF MULTIPLE SCLEROSIS

(71) Applicant: Merck Patent GmbH, Darmstadt (DE)

(72) Inventors: Martin Dyroff, Wayland, MA (US); David Mitchell, Broomfield, CO (US); Orestis Papasouliotis, Geneva (CH)

(73) Assignee: Merck Patent GmbH, Darmstadt (DE)

( * ) Notice: Subject to any disclaimer, the term of this patent is extended or adjusted under 35 U.S.C. 154(b) by 528 days.

(21) Appl. No.: 17/261,407

(22) PCT Filed: Jul. 19, 2019

(86) PCT No.: PCT/IB2019/056198
§ 371 (c)(1),
(2) Date: Jan. 19, 2021

(87) PCT Pub. No.: WO2020/016850
PCT Pub. Date: Jan. 23, 2020

(65) Prior Publication Data
US 2021/0260060 A1    Aug. 26, 2021

Related U.S. Application Data

(60) Provisional application No. 62/839,273, filed on Apr. 26, 2019, provisional application No. 62/730,184, filed on Sep. 12, 2018, provisional application No. 62/700,977, filed on Jul. 20, 2018.

(51) Int. Cl.
*A61K 31/506*    (2006.01)
*A61K 9/00*    (2006.01)
*A61P 25/28*    (2006.01)

(52) U.S. Cl.
CPC .......... *A61K 31/506* (2013.01); *A61K 9/0053* (2013.01); *A61P 25/28* (2018.01)

(58) Field of Classification Search
CPC ..... A61K 31/506; A61K 9/0053; A61P 25/28; A61P 25/00
USPC ......................................................... 514/256
See application file for complete search history.

(56) References Cited

U.S. PATENT DOCUMENTS

| | | | | |
|---|---|---|---|---|
| 10,689,363 B2 * | 6/2020 | Becker | ................. | C07D 403/12 |
| 10,716,788 B2 * | 7/2020 | Dellovade | .............. | A61K 31/69 |
| 2017/0136018 A1 * | 5/2017 | Dellovade | .............. | A61K 45/06 |

OTHER PUBLICATIONS

FDA Guidance for Industry Estimating the Maximum Safe Starting Dose in Initial Clinical Trials for Therapeutics in Adult Healthy Volunteers, 2005 (Year: 2005).*
NCT 02975349 "A Study of Efficacy and Safety of M2951 in Participants With Relapsing Multiple Sclerosis", History of Changes for Study, Version 1, available on Nov. 23, 2016 (Year: 2016).*
Tecfidera prescribing information, 2013, https://www.accessdata.fda.gov/drugsatfda_docs/label/2013/204063lbl.pdf. (Year: 2013).*
Manjunatha et al. Multiple Sclerosis: Therapeutic Strategies on the Horizon. Cureus 14(5): e24895. DOI 10.7759/cureus.24895, May 10, 2022, (Year: 2022).*
News Release by Merck KGaA on Oct. 12, 2018: "Positive Late-Breaking Phase II Data Evaluating Investigational Oral Therapy, Evobrutinib in RMS", retrieved from the Internet: https://www.emdgroup.com/en/news/positive-late-breaking-phase-II-12-10-2018.html. (Year: 2018).*
Montalban et al. New England Journal of Medicine 2019;380:2406-17. DOI: 10.1056/NEJMoa1901981, "Placebo-Controlled Trial of an Oral BTK Inhibitor in Multiple Sclerosis". (Year: 2019).*
Passaouliotis et al. Clin Transl Sci. 2022;15:2888-2898. "Determination of a clinically effective evobrutinib dose: Exposure-response analyses of a phase II relapsing multiple sclerosis study" (Year: 2022).*
Caldwell et al. J. Med. Chem. 2019, 62, 7643-7655 DOI: 10.1021/acs.jmedchem.9b00794, Discovery of Evobrutinib: An Oral, Potent, and Highly Selective, Covalent Bruton's Tyrosine Kinase (BTK) Inhibitor for the Treatment of Immunological Diseases (Year: 2019).*
Gajofatto, et al., "*Investigational immunosuppressants in early-stage clinical trials for the treatment of multiple sclerosis,*" Expert Opinion On Investigational Drugs, 2018, vol. 27, No. 3, 273-286.
International Search Report issued Dec. 3, 2019 in PCT/IB2019/056198, 5 Pages.
Montalban, et al., "*Primary analysis of a randomised, placebo-controlled phase 2 study of the Bruton's tyrosine kinase inhibitor evobrutinib (M2951) in patients with relapsing multiple sclerosis,*" Multiple Sclerosis Journal, Oct. 1, 2018, vol. 24, No. 2, 984-985, 1 page.
Montalban, et al., "*Efficacy and Safety of the Bruton's Tyrosine Kinase Inhibitor Evobrutinib (M2951) in Patients with Relapsing Multiple Sclerosis over 48 Weeks: a Randomized, Placebo-Controlled, Phase 2 Study,*" Journal of Neurology, Neurosurgery & Psychiatry 2019; 90:A18-A19, 1 page.
Merck, "*Merck Announces Positive Phase IIB Results for Evobrutinib in Relapsing Multiple Sclerosis,*" News Release, Retrieved From "https://www.emdgroup.com/press-releases/2018/mar/us/Evobrutinib-Positive-Phase-IIb-Results-US.pdf", Mar. 7, 2018, 2 Pages.
Written Opinion issued Dec. 3, 2019 in PCT/IB2019/056198, 6 Pages.

(Continued)

*Primary Examiner* — Jared Barsky
*Assistant Examiner* — Liyuan Mou
(74) *Attorney, Agent, or Firm* — EMD SERONO RESEARCH INSTITUTE

(57) ABSTRACT

Methods, compositions, and medical kits are useful for treating and preventing multiple sclerosis using 1-(4-(((6-amino-5-(4-phenoxyphenyl)pyrimidin-4-yl)amino)methyl)piperidin-1-yl)prop-2-en-1-one, or a pharmaceutically acceptable salt thereof, according to preferred dosing regimens.

32 Claims, 16 Drawing Sheets

(56) References Cited

OTHER PUBLICATIONS

Montalban X. et al. "Design of a phase II dose range finding, efficacy and safety study of the Bruton's tyrosine kinase inhibitor evobrutinib (M2951) in relapsing multiple sclerosis patients", Multiple Sclerosis Journal, vol. 23, S3, 2017, p. 324 (Whole document pp. 85-426).

* cited by examiner

SUBSTITUTED AMINO-PYRIMIDINE COMPOUND FOR USE IN A METHOD FOR TREATMENT AND PREVENTION OF MULTIPLE SCLEROSIS

CROSS-REFERENCE TO RELATED APPLICATIONS

This application is the National Stage entry under § 371 of International Application No. PCT/IB2019/056198, filed on Jul. 19, 2019, which claims the benefit of and priority to U.S. Provisional Patent Application Ser. No. 62/700,977, filed Jul. 20, 2018; U.S. Provisional Patent Application Ser. No. 62/730,184, filed Sep. 12, 2018; and U.S. Provisional Patent Application Ser. No. 62/839,273, filed Apr. 26, 2019; the content of each of which are hereby incorporated by reference.

BACKGROUND OF THE INVENTION

Field of the Invention

The invention provides methods, compositions, and medical kits for treating and preventing multiple sclerosis using 1-(4-(((6-amino-5-(4-phenoxyphenyl)pyrimidin-4-yl)amino)methyl)piperidin-1-yl)prop-2-en-1-one or a pharmaceutically acceptable salt thereof according to preferred dosing regimens.

Description of Related Art

Multiple sclerosis is a chronic, inflammatory, demyelinating disease of the central nervous system and is a common cause of serious neurological disability in young adults. Approximately 85% of patients with multiple sclerosis initially present with relapsing multiple sclerosis, which is characterized by periodic acute exacerbations of disease activity (multifocal inflammatory lesion, relapses) and periods of remission, consisting of partial or complete recovery. With recurring relapses, disability tends to accumulate.

There is an unmet need for highly effective and well-tolerated therapies for patients with relapsing multiple sclerosis at all stages of the disease. Early treatment with a highly efficacious, but safe disease-modifying drug could be highly advantageous for long-term quality of life for multiple sclerosis patients and might slow the process of brain atrophy, which accompanies axonal damage and loss in grey and white matter. An oral and safe solution for the treatment of multiple sclerosis patients with high disease activity would be an attractive treatment choice for patients switching therapy. Currently available therapeutic approaches for treating multiple sclerosis include interferon-beta, glatiramer acetate, fingolimod, and natalizumab. However, these therapeutics are not able to treat all patient and/or cause adverse side effects.

U.S. Patent Application Publication US 2017/0136018 describes methods of treating or preventing multiple sclerosis using certain compounds. Particular dosing protocols for treatment and prevention of multiple sclerosis using certain compounds would be desirable.

Accordingly, the need exists for new therapeutic methods that provide improved efficacy and/or reduced side effects for treating multiple sclerosis. The present invention addresses this need and provides other related advantages.

SUMMARY OF THE INVENTION

The invention provides methods, compositions, and medical kits for treating and preventing multiple sclerosis using 1-(4-(((6-amino-5-(4-phenoxyphenyl)pyrimidin-4-yl)amino)methyl)piperidin-1-yl)prop-2-en-1-one or a pharmaceutically acceptable salt thereof according to preferred dosing regimens. The compound is administered orally to the patient at a dosing amount and frequency selected to achieve superior therapeutic effects. The compound 1-(4-(((6-amino-5-(4-phenoxyphenyl)pyrimidin-4-yl)amino)methyl)piperidin-1-yl)prop-2-en-1-one has international nonproprietary name evobrutinib and is represented by Formula I having the formula:

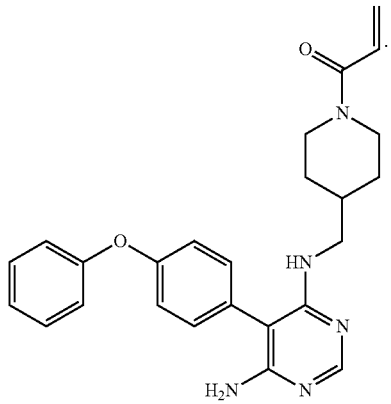 [SMILES: C=CC(=O)N1CCC(CNc2ncnc(N)c2-c2ccc(Oc3ccccc3)cc2)CC1]

Evobrutinib is also known under its research code M2951. Patients treated using the therapeutic methods, compositions, and kits are preferably adult patients, and a preferred method pertains to the treatment of adult patients with relapsing forms of multiple sclerosis, such as where evobrutinib is administered to the patient each day of the week for the duration needed.

Methods are provided herein where the compound is administered orally to the patient in proximity in time to when the patient consumes food. Additionally, methods are provided herein where the compound is administered orally to the patient when the patient is in a fasted state. It has been found that orally administering evobrutinib to a patient in proximity in time to when the patient consumes food results a significant increase in the bioavailability of evobrutinib—the significant increase in bioavailability of evobrutinib provides the benefit of being able to administer a reduced amount of evobrutinib to the patient. For this reason, there can be benefits to, for example, a dosing regimen in which a first unit dosage containing evobrutinib is administered to the patient at the time the patient consumes a breakfast meal in the morning, and a second unit dosage containing evobrutinib is administered to the patient at the time the patient consumes a dinner meal in the evening. This and other features for the therapeutic methods are described in more detail below.

Accordingly, one aspect of the invention provides a method for treating or preventing multiple sclerosis, wherein the method comprises orally administering to a patient in need thereof a compound of Formula I at a daily amount ranging from about 20 mg to about 300 mg or a pharmaceutically acceptable salt thereof. The daily amount may be administered as a single dose (QD) or as multiple dosages, such as two doses (BID). The doses may be administered in the form of one or more tablets or capsules. The method may be further characterized according to, for example, whether the patient has recently consumed food, such as preferably where the patient has consumed food (e.g., a meal) within 1 hour prior to receiving the unit formulation(s).

Another aspect of the invention provides a method for treating or preventing multiple sclerosis, where the method comprises orally administering to a patient in need thereof a compound of Formula I at a daily amount ranging from about 25 mg to about 150 mg or a pharmaceutically acceptable salt thereof. The compound of Formula I or pharmaceutically acceptable salt thereof may be administered to the patient in the form of two or more unit formulations containing compound of Formula I or a pharmaceutically acceptable salt thereof. In certain embodiments, the unit formulations are a tablet or capsule. The method may be further characterized according to, for example, whether the patient has recently consumed food, such as preferably where the patient has consumed food (e.g., a meal) within 1 hour prior to receiving the unit formulation(s), which may be, for example, a once daily dosage.

Another aspect of the invention provides a method for treating or preventing multiple sclerosis, where the method comprises orally administering to a patient in need thereof a once daily dosage of a compound of Formula I in an amount ranging from about 50 mg to about 100 mg or a pharmaceutically acceptable salt thereof. The once daily dosage may be administered to the patient in the form of two or more unit formulations containing compound of Formula I or a pharmaceutically acceptable salt thereof. In certain embodiments, the once daily dosage may be administered to the patient in the form a single unit formulation containing compound of Formula I or a pharmaceutically acceptable salt thereof. In certain embodiments, the unit formulation(s) are a tablet or capsule. The method may be further characterized according to, for example, whether the patient has recently consumed food, such as preferably where the patient has consumed food (e.g., a meal) within 1 hour prior to receiving the once daily dosage. The method may also be further characterized by, for example, features of the daily dosage of a compound of Formula I or a pharmaceutically acceptable salt thereof, such as where the daily dosage is about 75 mg of compound of Formula I or a pharmaceutically acceptable salt thereof.

Another aspect of the invention provides a method for treating or preventing multiple sclerosis, where the method comprises orally administering to a patient in need thereof two times per day a unit dosage containing a compound of Formula I in an amount ranging from about 25 mg to about 50 mg or a pharmaceutically acceptable salt thereof. Such twice daily administration of the unit dosage can provide advantages, such as reducing the variation in blood plasma levels of active ingredient throughout the day by administering the first unit dosage in the morning and the second unit dosage in the evening. The unit dosage may be administered to the patient in the form of two or more unit formulations containing compound of Formula I or a pharmaceutically acceptable salt thereof. In certain embodiments, the unit dosage may be administered to the patient in the form of a single unit formulation containing compound of Formula I or a pharmaceutically acceptable salt thereof. In certain embodiments, the unit formulation(s) are a tablet or capsule. The method may be further characterized according to, for example, whether the patient has recently consumed food, such as preferably where the patient has consumed food (e.g., a meal) within 1 hour prior to receiving the unit dosage. The method may also be further characterized by, for example, features of the unit dosage, such as where the unit dosage contains compound of Formula I in an amount of about 35 mg or a pharmaceutically acceptable salt thereof.

Another aspect of the invention provides a method for treating or preventing multiple sclerosis, wherein the method comprises orally administering to a patient in need thereof twice daily a unit dosage containing a compound of Formula I in an amount of about 45 mg or a pharmaceutically acceptable salt thereof, wherein the patient consumes a meal within about 1 hour of said administering. The unit dosage may be, for example, in the form of a tablet or capsule. The method may be further characterized according to the proximity in time between said administering and the patient consuming a meal. For example, in certain embodiments, a first unit dosage is administered to the patient within 1 hour after the patient consumes a breakfast meal, and a second unit dosage is administered to the patient within 1 hour after the patient consumes a dinner meal. As indicated above, it has been found that orally administering evobrutinib to a patient in proximity in time to when the patient consumes food results a significant increase in the bioavailability of evobrutinib—the significant increase in bioavailability of evobrutinib provides the benefit of being able to administer a reduced amount of evobrutinib to the patient.

DETAILED DESCRIPTION OF THE INVENTION

Figure 1:
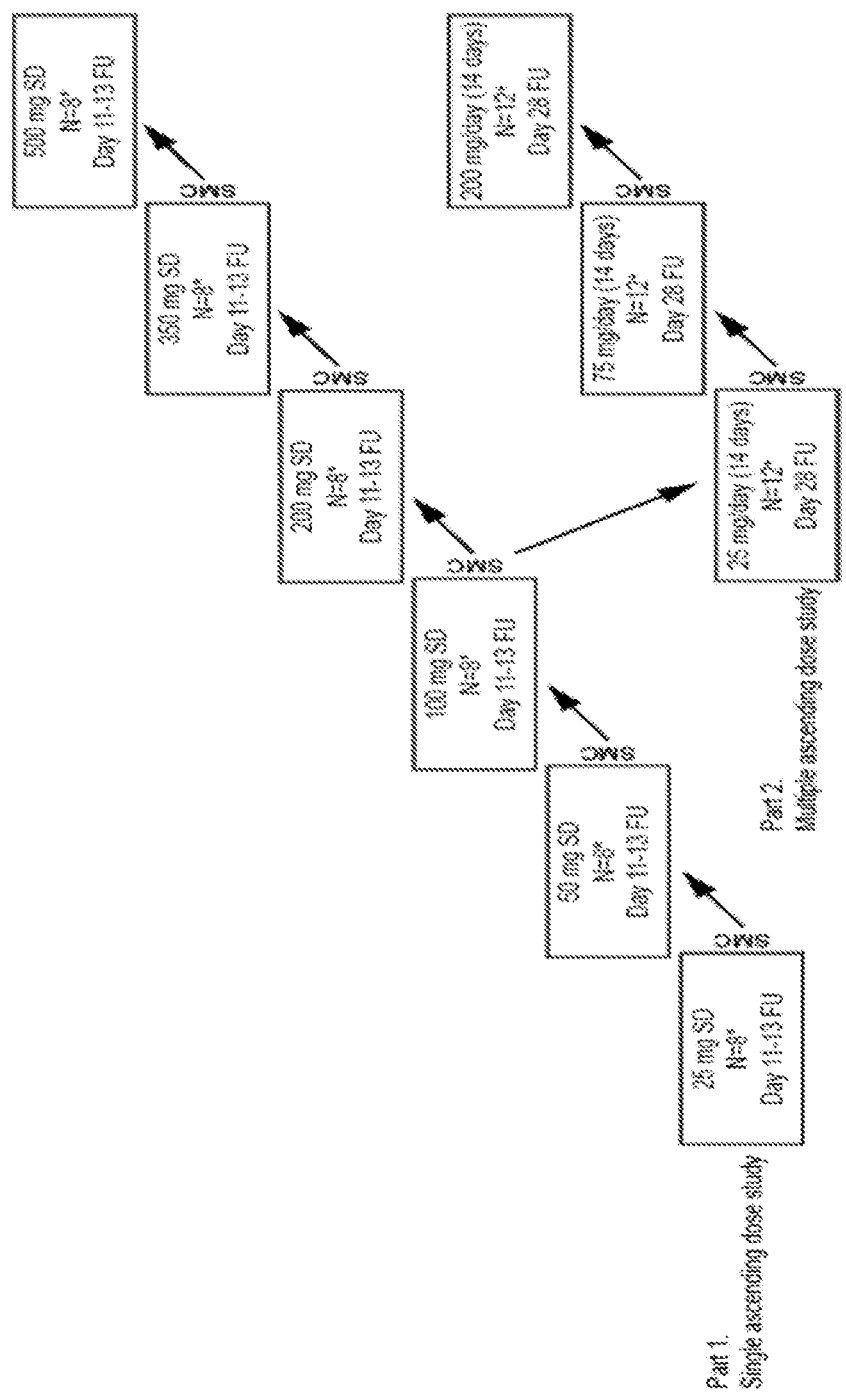
FIG. 1 depicts a flow chart of the design for the single ascendant dose study (Part 1) and the multiple ascendant dose study (Part 2) with evobrutinib in a phase I clinical study, as further described in Example 1.

The invention provides methods, compositions, and medical kits for treating and preventing multiple sclerosis using 1-(4-(((6-amino-5-(4-phenoxyphenyl)pyrimidin-4-yl)amino)methyl)piperidin-1-yl)prop-2-en-1-one or a pharmaceutically acceptable salt thereof according to preferred dosing regimens. The compound is administered orally to the patient at a dosing amount and frequency selected to achieve superior therapeutic effects. One dosing regimen for treating or preventing multiple sclerosis comprises orally administering to a patient in need thereof a compound of Formula I, as defined herein, at a daily amount ranging from about 20 mg to about 300 mg or a pharmaceutically acceptable salt thereof. Another dosing regimen for treating or preventing multiple sclerosis comprises orally administering to a patient in need thereof a compound of Formula I, as defined herein, at a daily amount ranging from about 25 mg to about 150 mg or a pharmaceutically acceptable salt thereof. Another dosing regimen for treating or preventing multiple sclerosis comprises orally administering to a patient in need thereof a once daily dosage of a compound of Formula I, as described herein, in an amount ranging from about 50 mg to about 100 mg or a pharmaceutically acceptable salt thereof. Still another dosing regimen for treating or preventing multiple sclerosis comprises orally administering to a patient in need thereof two times per day a unit dosage containing a compound of Formula I, as described herein, in an amount ranging from about 25 mg to about 50 mg or a pharmaceutically acceptable salt thereof. Such twice daily administration of the unit dosage can provide advantages, such as reducing the variation in blood plasma levels of active ingredient throughout the day by administering the first unit dosage in the morning and the second unit dosage in the evening.

Yet another dosing regimen for treating or preventing multiple sclerosis comprises orally administering to a patient in need thereof two times per day a unit dosage containing a compound of Formula I, as described herein, in an amount of about 45 mg or a pharmaceutically acceptable salt thereof. Where the method utilizes a unit dosage that provides the compound of Formula I in the form of a pharmaceutically acceptable salt, the unit dosage contains an amount of the pharmaceutically acceptable salt of Formula I sufficient to provide 45 mg of compound of Formula I. Preferably, in the said dosing regimen, the unit dosage, which is administered two times per day, contains a compound of Formula I in free base form in an amount of 45 mg.

Methods are provided herein where the compound is administered orally to the patient in proximity in time to when the patient consumes food. It has been found that orally administering evobrutinib to a patient in proximity in time to when the patient consumes food results a significant increase in the bioavailability of evobrutinib. The significant increase in bioavailability of evobrutinib when administered to a patient under a fed state provides the benefit of being able to administer a lower amount of evobrutinib to the patient. For this reason, there can be benefits to, for example, a dosing regimen in which a first unit dosage containing evobrutinib is administered to the patient at the time the patient consumes a breakfast meal in the morning, and a second unit dosage containing evobrutinib is administered to the patient at the time the patient consumes a dinner meal in the evening.

Preferably, the multiple sclerosis is relapsing multiple sclerosis.

The methods may be further characterized according to embodiments described herein. Various aspects and embodiments of the invention are set forth below in sections; however, aspects and/or embodiments of the invention described in one particular section are not to be limited to any particular section.

I. Definitions

To facilitate an understanding of the present invention, a number of terms and phrases are defined below.

The terms "a," "an" and "the" as used herein mean "one or more" and include the plural unless the context is inappropriate As used herein, the term "evobrutinib" refers to the compound having the following chemical structure:

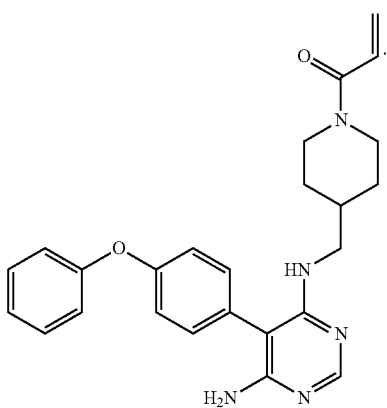 [SMILES: C=CC(=O)N1CCC(CNc2ncnc(N)c2-c2ccc(Oc3ccccc3)cc2)CC1]

The chemical name of evobrutinib is 1-(4-(((6-amino-5-(4-phenoxyphenyl)pyrimidin-4-yl)amino)methyl)piperidin-1-yl)prop-2-en-1-one.

As used herein, the term "patient" refers to organisms to be treated by the methods of the present invention. Such organisms preferably include, but are not limited to, mammals (e.g., murines, simians, equines (horses), bovines (cattle), porcines, canines, felines, and the like), and most preferably includes humans.

As used herein, the term "treating" includes any effect, e.g., lessening, reducing, modulating, ameliorating or eliminating, that results in the improvement of the condition, disease, disorder, and the like.

As used herein, the term "pharmaceutical composition" refers to one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, a pharmaceutical composition of the present invention encompasses any composition made by admixing a compound of the present invention and a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

A compound of the invention may be presented in the form of a free base, pharmaceutically acceptable salt, a solvate, or a solvate of a salt. In certain embodiments, a compound of the invention may be in the form of a pharmaceutically acceptable salt. The term "pharmaceutically acceptable salt" refers to salts prepared from pharmaceutically acceptable non-toxic bases or acids, including inorganic bases or acids and organic bases or acids. Accordingly, a compound of the invention which contains one or more acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. A compound of the invention which contains one or more basic groups, i.e., groups which can be protonated, can be present in salt form, and can be used according to the invention in the form of an addition salt with inorganic or organic acid. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. The present invention also includes all salts of a compound of the present invention which, owing to low physiological compatibility, are not directly suitable for use in pharmaceuticals but which can be used, for example, as intermediates for chemical reactions or for the preparation of pharmaceutically acceptable salts.

As a general matter, compositions specifying a percentage are by weight unless otherwise specified. Further, if a variable is not accompanied by a definition, then the previous definition of the variable controls.

II. Therapeutic Applications

The invention provides methods for treating or preventing multiple sclerosis using evobrutinib or a pharmaceutically acceptable salt thereof. The methods are described in more detail below.

First Therapeutic Method

One aspect of the invention provides a method for treating or preventing multiple sclerosis. The method comprises orally administering to a patient in need thereof a compound of Formula I at a daily amount ranging from about 20 mg to about 300 mg or a pharmaceutically acceptable salt thereof, wherein Formula I is represented by:

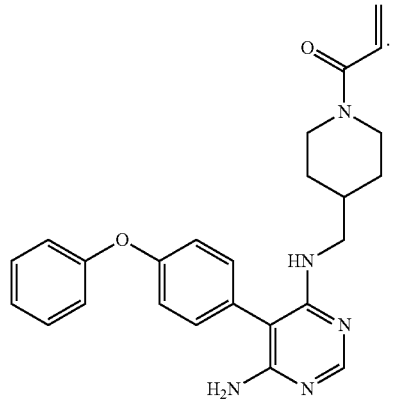 [SMILES: C=CC(=O)N1CCC(CNc2ncnc(N)c2-c2ccc(Oc3ccccc3)cc2)CC1]

The method may be further characterized by, for example, the amount of compound of Formula I or pharmaceutically acceptable salt thereof that is administered to the patient. For example, in certain embodiments, the patient is orally administered a compound of Formula I at a daily amount ranging from about 20 mg to about 200 mg or a pharmaceutically acceptable salt thereof. In certain embodiments, the patient is orally administered a compound of Formula I at a daily amount ranging from about 30 mg to about 300 mg or a pharmaceutically acceptable salt thereof. In certain embodiments, the patient is orally administered a compound of Formula I at a daily amount ranging from about 25 mg to about 150 mg or a pharmaceutically acceptable salt thereof. In certain embodiments, the patient is orally administered a compound of Formula I at a daily amount ranging from about 85 mg to about 95 mg or a pharmaceutically acceptable salt thereof. In certain embodiments, the patient is orally administered a compound of Formula I at a daily amount of about 90 mg or a pharmaceutically acceptable salt thereof. In certain embodiments, the patient is orally administered a compound of Formula I at a daily amount of 90 mg or a pharmaceutically acceptable salt thereof. In certain embodiments, the patient is orally administered a compound of Formula I at a daily amount of about 90 mg. In certain embodiments, the patient is orally administered a compound of Formula I at a daily amount of 90 mg. For clarity, the phrase a compound of Formula I at a daily amount ranging from about 85 mg to about 95 mg or a pharmaceutically acceptable salt thereof means that the compound of Formula I is administered in an amount ranging from about 85 mg to about 95 mg or that a molar equivalent amount of a pharmaceutically acceptable salt of Formula I is administered to the patient.

In a more specific aspect, the invention provides a method for treating or preventing multiple sclerosis, wherein the method comprises orally administering to a patient in need thereof a compound of Formula I at a daily amount ranging from about 25 mg to about 150 mg or a pharmaceutically acceptable salt thereof, wherein Formula I is represented by:

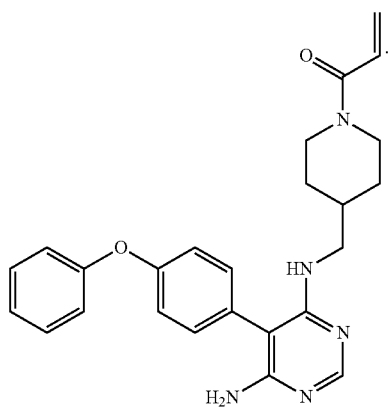 [SMILES: C=CC(=O)N1CCC(CNc2ncnc(N)c2-c2ccc(Oc3ccccc3)cc2)CC1]

The method may be further characterized by, for example, the amount of compound of Formula I or pharmaceutically acceptable salt thereof that is administered to the patient. For example, in certain embodiments, the patient is orally administered a compound of Formula I at a daily amount ranging from about 25 mg to about 50 mg or a pharmaceutically acceptable salt thereof. In certain embodiments, the patient is orally administered a compound of Formula I at a daily amount ranging from about 50 mg to about 75 mg or a pharmaceutically acceptable salt thereof. In certain embodiments, the patient is orally administered a compound of Formula I at a daily amount ranging from about 75 mg to about 100 mg or a pharmaceutically acceptable salt thereof. In certain embodiments, the patient is orally administered a compound of Formula I at a daily amount ranging from about 100 mg to about 125 mg or a pharmaceutically acceptable salt thereof. In certain embodiments, the patient is orally administered a compound of Formula I at a daily amount ranging from about 125 mg to about 150 mg or a pharmaceutically acceptable salt thereof.

In yet other embodiments, the patient is orally administered a compound of Formula I at a daily amount ranging from about 25 mg to about 35 mg or a pharmaceutically acceptable salt thereof. In yet other embodiments, the patient is orally administered a compound of Formula I at a daily amount ranging from about 35 mg to about 45 mg or a pharmaceutically acceptable salt thereof. In yet other embodiments, the patient is orally administered a compound of Formula I at a daily amount ranging from about 45 mg to about 55 mg or a pharmaceutically acceptable salt thereof. In yet other embodiments, the patient is orally administered a compound of Formula I at a daily amount ranging from about 55 mg to about 65 mg or a pharmaceutically acceptable salt thereof. In yet other embodiments, the patient is orally administered a compound of Formula I at a daily amount ranging from about 65 mg to about 75 mg or a pharmaceutically acceptable salt thereof. In yet other embodiments, the patient is orally administered a compound of Formula I at a daily amount ranging from about 75 mg to about 85 mg or a pharmaceutically acceptable salt thereof. In yet other embodiments, the patient is orally administered a compound of Formula I at a daily amount ranging from about 85 mg to about 95 mg or a pharmaceutically acceptable salt thereof. In yet other embodiments, the patient is orally administered a compound of Formula I at a daily amount ranging from about 95 mg to about 100 mg or a pharmaceutically acceptable salt thereof. In yet other embodiments, the patient is orally administered a compound of Formula I at a daily amount ranging from about 100 mg to about 105 mg or a pharmaceutically acceptable salt thereof. In yet other embodiments, the patient is orally administered a compound of Formula I at a daily amount ranging from about 105 mg to about 110 mg or a pharmaceutically acceptable salt thereof. In yet other embodiments, the patient is orally administered a compound of Formula I at a daily amount ranging from about 110 mg to about 115 mg or a pharmaceutically acceptable salt thereof. In yet other embodiments, the patient is orally administered a compound of Formula I at a daily amount ranging from about 115 mg to about 120 mg or a pharmaceutically acceptable salt thereof. In yet other embodiments, the patient is orally administered a compound of Formula I at a daily amount ranging from about 120 mg to about 125 mg or a pharmaceutically acceptable salt thereof. In yet other embodiments, the patient is orally administered a compound of Formula I at a daily amount ranging from about 125 mg to about 130 mg or a pharmaceutically acceptable salt thereof. In yet other embodiments, the patient is orally administered a compound of Formula I at a daily amount ranging from about 130 mg to about 135 mg or a pharmaceutically acceptable salt thereof. In yet other embodiments, the patient is orally administered a compound of Formula I at a daily amount ranging from about 135 mg to about 140 mg or a pharmaceutically acceptable salt thereof. In yet other embodiments, the patient is orally administered a compound of Formula I at a daily amount ranging from about 145 mg to about 150 mg or a pharmaceutically acceptable salt thereof. In certain embodiments, the patient is orally administered a compound of Formula I at a daily amount ranging from about 50 mg to about 100 mg or a pharmaceutically acceptable salt thereof.

In yet other embodiments, the patient is orally administered a compound of Formula I at a daily amount ranging from about 50 mg to about 150 mg or a pharmaceutically acceptable salt thereof. In yet other embodiments, the patient is orally administered a compound of Formula I at a daily amount of about 90 mg or a pharmaceutically acceptable salt thereof. In yet other embodiments, the patient is orally administered a compound of Formula I at a daily amount of 90 mg or a pharmaceutically acceptable salt thereof. In certain embodiments, the patient is orally administered a compound of Formula I at a daily amount of about 90 mg. In certain embodiments, the patient is orally administered a compound of Formula I at a daily amount of 90 mg.

The method may be further characterized by, for example, the number of times per day that the compound of Formula I or a pharmaceutically acceptable salt thereof is administered to the patient. In certain embodiments, the compound of Formula I or a pharmaceutically acceptable salt thereof is administered only once per day. In certain embodiments, the compound of Formula I or a pharmaceutically acceptable salt thereof is administered twice per day.

In certain embodiments, the patient is orally administered twice per day a unit dosage, wherein each unit dosage contains a compound of Formula I in an amount of about 45 mg or a pharmaceutically acceptable salt thereof. In certain embodiments, the patient is orally administered twice per day a unit dosage, wherein each unit dosage contains a compound of Formula I in an amount of 45 mg or a pharmaceutically acceptable salt thereof. In certain embodiments, the patient is orally administered twice per day a unit dosage, wherein each unit dosage contains a compound of Formula I in an amount of about 45 mg. In certain embodiments, the patient is orally administered twice per day a unit dosage, wherein each unit dosage contains a compound of Formula I in an amount of 45 mg.

In certain embodiments where the compound of Formula I or a pharmaceutically acceptable salt thereof is administered twice per day, the method may be further characterized by the duration of time between the first administration and the second administration. For example, in certain embodiments, there is at least 4, 5, 6, 7, 8, 9, 10, 11, 12, 13, or 14 hours between the first administration and the second administration. In certain embodiments, there is at least 4 hours between administration of a first unit dosage and a second unit dosage to the patient on the same day. In certain embodiments, there is at least 5 hours between administration of a first unit dosage and a second unit dosage to the patient on the same day. In certain embodiments, there is at least 6 hours between administration of a first unit dosage and a second unit dosage to the patient on the same day. In certain embodiments, there is at least 7 hours between administration of a first unit dosage and a second unit dosage to the patient on the same day. In certain embodiments, there is at least 8 hours between administration of a first unit dosage and a second unit dosage to the patient on the same day. In certain embodiments, there is at least 9 hours between administration of a first unit dosage and a second unit dosage to the patient on the same day. In certain embodiments, there is at least 10 hours between administration of a first unit dosage and a second unit dosage to the patient on the same day. In certain embodiments, there is at least 11 hours between administration of a first unit dosage and a second unit dosage to the patient on the same day. In certain embodiments, there is at least 12 hours between administration of a first unit dosage and a second unit dosage to the patient on the same day. In certain embodiments, there is from about 4 hours to about 14 hours between the first administration and the second administration. In certain embodiments, there is from about 6 hours to about 14 hours between the first administration and the second administration. In certain embodiments, there is from about 6 hours to about 8 hours, about 7 hours to about 9 hours, about 8 hours to about 10 hours, about 9 hours to about 11 hours, about 10 hours to about 12 hours, about 11 hours to about 13 hours, or about 12 hours to about 14 hours between the first administration and the second administration.

The method may be further characterized by, for example, whether or not the patient has recently consumed or will consume food in relation to when the patient receives the compound of Formula I or a pharmaceutically acceptable salt thereof. For example, in certain embodiments, the patient has recently consumed food prior to receiving the compound (i.e., the compound of Formula I or a pharmaceutically acceptable salt thereof). In certain embodiments, the patient has consumed food within 1 hour prior to receiving the compound (i.e., the compound of Formula I or a pharmaceutically acceptable salt thereof). In certain embodiments, the patient has not recently consumed food prior to receiving the compound (i.e., the compound of Formula I or a pharmaceutically acceptable salt thereof). In certain embodiments, the patient has not consumed food within 1 hour prior to receiving the compound (i.e., the compound of Formula I or a pharmaceutically acceptable salt thereof). In yet other embodiments, the patient consumes a meal within 1 hour of receiving said compound. In yet other embodiments, the patient consumes a meal within 30 minutes of receiving said compound. In yet other embodiments, the administering is performed at a time the patient consumes a meal.

Alternatively or in addition, the method may be further characterized by whether or not the patient is in a fed state or in a fasted state when the compound of Formula I or a pharmaceutically acceptable salt thereof is administered to the patient. For example, in certain embodiments, patient is in a fed state when the compound of Formula I or a pharmaceutically acceptable salt thereof is administered to the patient. In certain embodiments, patient is in a fasted state when the compound of Formula I or a pharmaceutically acceptable salt thereof is administered to the patient.

In a more specific aspect, the invention provides a method for treating or preventing multiple sclerosis, wherein the method comprises orally administering to a patient in need thereof a once daily dosage of a compound of Formula I in an amount ranging from about 30 mg to about 300 mg or a pharmaceutically acceptable salt thereof, wherein the patient is in a fasted state when the compound of Formula I or a pharmaceutically acceptable salt thereof is administered to the patient.

In a more specific aspect, the invention provides a method for treating or preventing multiple sclerosis, wherein the method comprises orally administering to a patient in need thereof a once daily dosage of a compound of Formula I in an amount ranging from about 20 mg to about 200 mg or a pharmaceutically acceptable salt thereof, wherein the patient is in a fed state when the compound of Formula I or a pharmaceutically acceptable salt thereof is administered to the patient.

Another aspect of the invention provides a method for treating or preventing multiple sclerosis, wherein the method comprises orally administering to a patient in need thereof two times per day a unit dosage containing a compound of Formula I in an amount ranging from about 15 mg to about 150 mg or a pharmaceutically acceptable salt thereof, wherein the patient is in a fasted state when the compound of Formula I or a pharmaceutically acceptable salt thereof is administered to the patient.

Another aspect of the invention provides a method for treating or preventing multiple sclerosis, wherein the method comprises orally administering to a patient in need thereof two times per day a unit dosage containing a compound of Formula I in an amount ranging from about 10 mg to about 100 mg or a pharmaceutically acceptable salt thereof, wherein the patient is in a fed state when the compound of Formula I or a pharmaceutically acceptable salt thereof is administered to the patient. Such twice daily administration of the unit dosage can provide advantages, such as reducing the variation in blood plasma levels of active ingredient throughout the day by administering the first unit dosage in the morning and the second unit dosage in the evening. Administering the first unit dosage in the morning after the patient wakes up and then administering the second unit dosage in the evening before the patient goes to sleep is procedurally desirable for facilitating patient compliance.

Second Therapeutic Method

One aspect of the invention provides a method for treating or preventing multiple sclerosis. The method comprises orally administering to a patient in need thereof a once daily dosage of a compound of Formula I in an amount ranging from about 50 mg to about 100 mg or a pharmaceutically acceptable salt thereof, wherein Formula I is represented by:

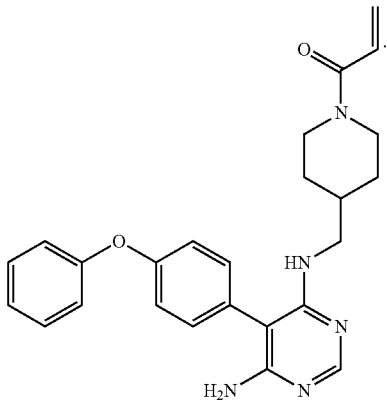 [SMILES: C=CC(=O)N1CCC(CNc2ncnc(N)c2-c2ccc(Oc3ccccc3)cc2)CC1]

The method may be further characterized by, for example, whether the once daily dosage is administered to the patient as a single unit formulation or as two or more unit formulations. In certain embodiments, the once daily dosage is administered to the patient in the form of a single unit formulation containing compound of Formula I or a pharmaceutically acceptable salt thereof. In certain embodiments, the once daily dosage is administered to the patient in the form of two or more unit formulations containing compound of Formula I or a pharmaceutically acceptable salt thereof. In certain embodiments, the once daily dosage is administered to the patient in the form of three unit formulations containing compound of Formula I or a pharmaceutically acceptable salt thereof. In certain embodiments, the once daily dosage is administered to the patient in the form of three unit formulations each containing compound of Formula I in an amount of about 25 mg. In certain embodiments, the once daily dosage is administered to the patient in the form of three unit formulations each containing compound of Formula I in an amount of 25 mg.

The method may be further characterized by, for example, the nature of the unit formulation(s). In certain embodiments, the unit formulation(s) are a tablet or capsule.

The method may be further characterized by, for example, whether the once daily dosage contains (i) a compound of Formula I or (ii) a pharmaceutically acceptable salt of a compound of Formula I. In certain embodiments, the once daily dosage is about 75 mg of the compound of Formula I. In yet other embodiments, the once daily dosage is 75 mg of the compound of Formula I. In certain embodiments, the once daily dosage is about 100 mg of the compound of Formula I. In yet other embodiments, the once daily dosage is 100 mg of the compound of Formula I.

The method may be further characterized by, for example, the time of day in which the once daily dosage is administered to the patient. In certain embodiments, the once daily dosage is administered to the patient in the morning.

The method may be further characterized by, for example, whether or not the patient has recently consumed or will consume food in relation to when the patient receives the once daily dosage. In certain embodiments, the patient has consumed food within 2 hours prior to receiving the once daily dosage. In certain embodiments, the patient has consumed food within 1 hour prior to receiving the once daily dosage. In certain embodiments, the patient consumes food within 30 minutes of receiving the once daily dosage.

The method may be further characterized by, for example, the number of consecutive days in which the patient receives the once daily dosage. For example, in certain embodiments, the patient receives the once daily dosage for a duration of at least 2 weeks. In certain embodiments, the patient receives the once daily dosage for a duration of at least 1 month. In certain embodiments, the patient receives the once daily dosage for a duration of at least 2 months, 3 months, 4 months, or 5 months. In certain embodiments, the patient receives the once daily dosage for a duration of at least 6 months.

Third Therapeutic Method

One aspect of the invention provides a method for treating or preventing multiple sclerosis. The method comprises orally administering to a patient in need thereof two times per day a unit dosage containing a compound of Formula I in an amount ranging from about 25 mg to about 50 mg or a pharmaceutically acceptable salt thereof, wherein Formula I is represented by:

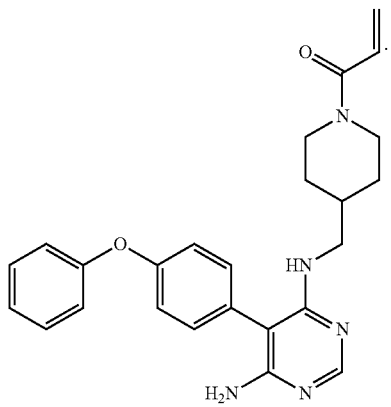 [SMILES: C=CC(=O)N1CCC(CNc2ncnc(N)c2-c2ccc(Oc3ccccc3)cc2)CC1]

Such twice daily administration of the unit dosage can provide advantages, such as reducing the variation in blood plasma levels of active ingredient throughout the day by administering the first unit dosage in the morning and the second unit dosage in the evening. Administering the first unit dosage in the morning after the patient wakes up and then administering the second unit dosage in the evening before the patient goes to sleep is procedurally desirable for facilitating patient compliance.

The method may be further characterized by, for example, the unit dosage is administered to the patient as a single unit formulation or two or more unit formulations. In certain embodiments, the unit dosage is administered to the patient in the form of two or more unit formulations containing compound of Formula I or a pharmaceutically acceptable salt thereof. In certain embodiments, the unit dosage is administered to the patient in the form of two unit formulations containing compound of Formula I or a pharmaceutically acceptable salt thereof. In certain embodiments, the unit dosage is administered to the patient in the form of a single unit formulation containing compound of Formula I or a pharmaceutically acceptable salt thereof.

The method may be further characterized by, for example, the nature of the unit formulation(s). In certain embodiments, the unit formulation(s) are a tablet or capsule.

The method may be further characterized by, for example, the amount of compound of Formula I in a unit dosage. In certain embodiments, the unit dosage contains the compound of Formula I in the amount of about 35 mg. In certain embodiments, the unit dosage contains the compound of Formula I in the amount of 35 mg. In certain embodiments, the unit dosage contains the compound of Formula I in the amount of about 45 mg. In certain embodiments, the unit dosage contains the compound of Formula I in the amount of 45 mg.

The method may be further characterized by, for example, the duration of time between administering a first unit dosage to a patient and administering a second unit dosage to the patient on the same day. In certain embodiments, there is at least 4 hours between administration of a first unit dosage and a second unit dosage to the patient on the same day. In certain embodiments, there is at least 5 hours between administration of a first unit dosage and a second unit dosage to the patient on the same day. In certain embodiments, there is at least 6 hours between administration of a first unit dosage and a second unit dosage to the patient on the same day. In certain embodiments, there is at least 7 hours between administration of a first unit dosage and a second unit dosage to the patient on the same day. In certain embodiments, there is at least 8 hours between administration of a first unit dosage and a second unit dosage to the patient on the same day. In certain embodiments, there is at least 9 hours between administration of a first unit dosage and a second unit dosage to the patient on the same day. In certain embodiments, there is at least 10 hours between administration of a first unit dosage and a second unit dosage to the patient on the same day. In certain embodiments, there is at least 11 hours between administration of a first unit dosage and a second unit dosage to the patient on the same day. In certain embodiments, there is at least 12 hours between administration of a first unit dosage and a second unit dosage to the patient on the same day. In certain embodiments, there is from about 4 hours to about 14 hours between administration of a first unit dosage and a second unit dosage to the patient on the same day. In certain embodiments, there is from about 6 hours to about 14 hours between administration of a first unit dosage and a second unit dosage to the patient on the same day. In certain embodiments, there is from about 6 hours to about 8 hours between administration of a first unit dosage and a second unit dosage to the patient on the same day. In certain embodiments, there is from about 7 hours to about 9 hours between administration of a first unit dosage and a second unit dosage to the patient on the same day. In certain embodiments, there is from about 8 hours to about 10 hours between administration of a first unit dosage and a second unit dosage to the patient on the same day. In certain embodiments, there is from about 9 hours to about 11 hours between administration of a first unit dosage and a second unit dosage to the patient on the same day. In certain embodiments, there is from about 10 hours to about 12 hours between administration of a first unit dosage and a second unit dosage to the patient on the same day. In certain embodiments, there is from about 11 hours to about 13 hours between administration of a first unit dosage and a second unit dosage to the patient on the same day. In certain embodiments, there is from about 12 hours to about 14 hours between administration of a first unit dosage and a second unit dosage to the patient on the same day. In certain other embodiments, there is about 4, 5, 6, 7, 8, 9, 10, 11, 12, 13, or 14 hours between administration of a first unit dosage and a second unit dosage to the patient on the same day.

The method may be further characterized by, for example, the time of day in which the unit dosages are administered to the patient. In certain embodiments, a first unit dosage is administered to the patient in the morning, and a second unit dosage is administered to the patient in the evening.

The method may be further characterized by, for example, whether or not the patient has recently consumed or will consume food in relation to when the patient receives a unit dosage. In certain embodiments, the patient has consumed food within 2 hours prior to receiving the unit dosage. In certain embodiments, the patient has consumed food within 1 hour prior to receiving the unit dosage. In certain embodiments, the patient consumes food within 30 minutes of receiving the unit dosage.

The method may be further characterized by, for example, the number of consecutive days in which the patient receives the once daily dosage. For example, in certain embodiments, the patient receives the unit dosage two times per day for a duration of at least 2 weeks. In certain embodiments, the patient receives the unit dosage two times per day for a duration of at least 1 month. In certain embodiments, the patient receives the unit dosage two times per day for a duration of at least 6 months.

Fourth Therapeutic Method

One aspect of the invention provides a method for treating or preventing multiple sclerosis, wherein the method comprises orally administering to a patient in need thereof a compound of Formula I at a daily amount ranging from about 20 mg to about 300 mg or a pharmaceutically acceptable salt thereof, wherein the patient is a fed state or a fasted state, and Formula I is represented by:

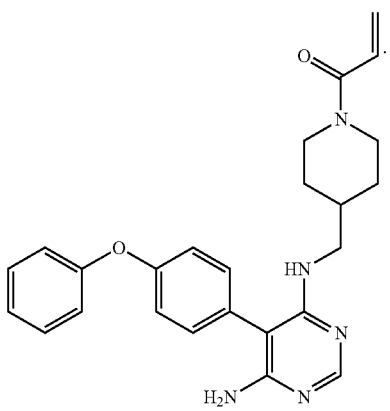 [SMILES: C=CC(=O)N1CCC(CNc2ncnc(N)c2-c2ccc(Oc3ccccc3)cc2)CC1]

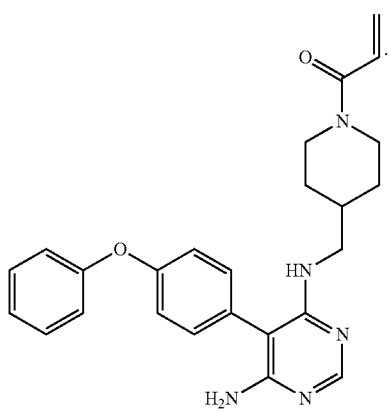 [SMILES: C=CC(=O)N1CCC(CNc2ncnc(N)c2-c2ccc(Oc3ccccc3)cc2)CC1]

The method may be further characterized according to whether the patient is in a fed state or a fasted state when the compound of Formula I is administered to the patient. For example, in certain embodiments, the patient is in a fed state. In certain other embodiments, the patient is in a fasted state. The method may be further characterized by, for example, whether or not the patient has recently consumed or will consume food. In certain embodiments, the patient has consumed food within 2 hours prior to receiving the compound of Formula I or pharmaceutically acceptable salt thereof. In certain embodiments, the patient has consumed food within 1 hour prior to receiving the Formula I or pharmaceutically acceptable salt thereof. In certain embodiments, the patient consumes food within 30 minutes of receiving the Formula I or pharmaceutically acceptable salt thereof.

The method may be further characterized by, for example, the amount of compound of Formula I or pharmaceutically acceptable salt thereof that is administered to the patient. For example, in certain embodiments, the patient is orally administered a compound of Formula I at a daily amount ranging from about 20 mg to about 200 mg or a pharmaceutically acceptable salt thereof. In certain embodiments, the patient is orally administered a compound of Formula I at a daily amount ranging from about 30 mg to about 300 mg or a pharmaceutically acceptable salt thereof. In certain embodiments, the patient is orally administered a compound of Formula I at a daily amount ranging from about 25 mg to about 150 mg or a pharmaceutically acceptable salt thereof. In certain embodiments, the patient is orally administered a compound of Formula I at a daily amount ranging from about 85 mg to about 95 mg or a pharmaceutically acceptable salt thereof. In certain embodiments, the patient is orally administered a compound of Formula I at a daily amount of about 90 mg or a pharmaceutically acceptable salt thereof. In certain embodiments, the patient is orally administered a compound of Formula I at a daily amount of about 90 mg.

A more specific aspect of the invention provides a method for treating or preventing multiple sclerosis, wherein the method comprises orally administering to a patient in need thereof twice daily a unit dosage containing a compound of Formula I in an amount of about 45 mg or a pharmaceutically acceptable salt thereof, wherein the patient is in a fed state and Formula I is represented by:

The method may be further characterized by, for example, the amount of compound of Formula I in a unit dosage. In certain embodiments, the unit dosage contains about 45 mg of compound of Formula I. In certain embodiments, the unit dosage contains 45 mg of compound of Formula I.

Another more specific aspect of the invention provides a method for treating or preventing multiple sclerosis, wherein the method comprises orally administering to a patient in need thereof twice daily a unit dosage containing a compound of Formula I in an amount of about 45 mg or a pharmaceutically acceptable salt thereof, wherein the patient consumes a meal within about 1 hour of said administering, and Formula I is represented by:

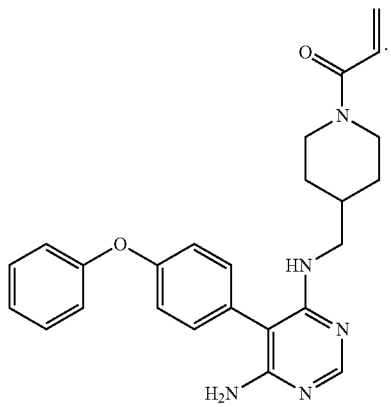 [SMILES: C=CC(=O)N1CCC(CNc2ncnc(N)c2-c2ccc(Oc3ccccc3)cc2)CC1]

The method may be further characterized by, for example, the amount of compound of Formula I in a unit dosage. In certain embodiments, the unit dosage contains about 45 mg of compound of Formula I. In certain embodiments, the unit dosage contains 45 mg of compound of Formula I.

The method may be further characterized by, for example, an embodiment where the unit dosage is administered to the patient as a single unit formulation or two or more unit formulations. In certain embodiments, the unit dosage is administered to the patient in the form of one or more unit formulations containing compound of Formula I or a pharmaceutically acceptable salt thereof. In certain embodiments, the unit dosage is administered to the patient in the form of two or more unit formulations containing compound of Formula I or a pharmaceutically acceptable salt thereof. In certain embodiments, the unit dosage is administered to the patient in the form of a single unit formulation containing compound of Formula I or a pharmaceutically acceptable salt thereof. In certain embodiments, the unit formulation(s) are a tablet or capsule.

The method may be further characterized by, for example, the duration of time between administering a first unit dosage to a patient and administering a second unit dosage to the patient on the same day. In certain embodiments, there is at least 4 hours between administration of a first unit dosage and a second unit dosage to the patient on the same day. In certain embodiments, there is at least 5 hours between administration of a first unit dosage and a second unit dosage to the patient on the same day. In certain embodiments, there is at least 6 hours between administration of a first unit dosage and a second unit dosage to the patient on the same day. In certain embodiments, there is at least 7 hours between administration of a first unit dosage and a second unit dosage to the patient on the same day. In certain embodiments, there is at least 8 hours between administration of a first unit dosage and a second unit dosage to the patient on the same day. In certain embodiments, there is at least 9 hours between administration of a first unit dosage and a second unit dosage to the patient on the same day. In certain embodiments, there is at least 10 hours between administration of a first unit dosage and a second unit dosage to the patient on the same day. In certain embodiments, there is at least 11 hours between administration of a first unit dosage and a second unit dosage to the patient on the same day. In certain embodiments, there is at least 12 hours between administration of a first unit dosage and a second unit dosage to the patient on the same day. In certain embodiments, there is from about 4 hours to about 14 hours between administration of a first unit dosage and a second unit dosage to the patient on the same day. In certain embodiments, there is from about 6 hours to about 14 hours between administration of a first unit dosage and a second unit dosage to the patient on the same day. In certain embodiments, there is from about 6 hours to about 8 hours between administration of a first unit dosage and a second unit dosage to the patient on the same day. In certain embodiments, there is from about 7 hours to about 9 hours between administration of a first unit dosage and a second unit dosage to the patient on the same day. In certain embodiments, there is from about 8 hours to about 10 hours between administration of a first unit dosage and a second unit dosage to the patient on the same day. In certain embodiments, there is from about 9 hours to about 11 hours between administration of a first unit dosage and a second unit dosage to the patient on the same day. In certain embodiments, there is from about 10 hours to about 12 hours between administration of a first unit dosage and a second unit dosage to the patient on the same day. In certain embodiments, there is from about 11 hours to about 13 hours between administration of a first unit dosage and a second unit dosage to the patient on the same day. In certain embodiments, there is from about 12 hours to about 14 hours between administration of a first unit dosage and a second unit dosage to the patient on the same day. In certain other embodiments, there is about 4, 5, 6, 7, 8, 9, 10, 11, 12, 13, or 14 hours between administration of a first unit dosage and a second unit dosage to the patient on the same day.

The method may be further characterized by, for example, the time of day in which the unit dosages are administered to the patient. In certain embodiments, a first unit dosage is administered to the patient in the morning, and a second unit dosage is administered to the patient in the evening. Administering the first unit dosage in the morning after the patient wakes up and then administering the second unit dosage in the evening before the patient goes to sleep is procedurally desirable for facilitating patient compliance The method may be further characterized by, for example, the consumption of food (e.g., a meal) by the patient in proximity to the time of administering the compound of Formula I or pharmaceutically acceptable salt thereof. Consumption of food (e.g., a meal) can facilitate absorption of the compound and, thereby, provide greater bioavailability of the compound. The food is desirably solid food, and most desirably is a meal (e.g., a light-fat meal or a medium-fat meal). The meal may be, for example, a breakfast meal or a dinner meal.

In certain embodiments, said administering is performed at the time the patient consumes a meal. More specifically, in certain embodiments, a first unit dosage is administered to the patient at the time the patient consumes a breakfast meal in the morning, and a second unit dosage is administered to the patient at the time the patient consumes a dinner meal in the evening. In certain other embodiments, a first unit dosage is administered to the patient within 1 hour of the time the patient consumes a breakfast meal, and a second unit dosage is administered to the patient within 1 hour of the time the patient consumes a dinner meal. In a preferred embodiment, a first unit dosage is administered to the patient within 1 hour after the patient consumes a breakfast meal, and a second unit dosage is administered to the patient within 1 hour after the patient consumes a dinner meal. Further features characterizing the consumption of food are described herein below.

Further Characterization of First, Second, Third, and Fourth Therapeutic Methods The First, Second, Third, and Fourth Therapeutic Methods may be further characterized by, for example, result to be achieved by the therapeutic method, type of multiple sclerosis, identity of the patient, effect of the method on the number and/or size of gadolinium positive T1 magnetic resonance imaging lesions, and whether the patient is in a fasted state or a fed state when the compound of Formula I or pharmaceutically acceptable salt thereof is administered to the patient. These features are described in more detail below.

Result Achieved

The method may be further characterized by, for example, result to be achieved. For example, in certain embodiments, the method is for treating multiple sclerosis. In yet other embodiments, the method is for preventing multiple sclerosis.

Type of Multiple Sclerosis

The method may be further characterized according to the type of multiple sclerosis. In certain embodiments, the multiple sclerosis is relapsing multiple sclerosis, relapsing-remitting multiple sclerosis, progressive multiple sclerosis, secondary-progressive multiple sclerosis, primary-progressive multiple sclerosis, or progressive-relapsing multiple sclerosis. In yet other embodiments, the multiple sclerosis is relapsing multiple sclerosis.

Identity of the Patient

The methods may be further characterized by, for example, identity of the patient. In certain embodiments, the patient is an adult human.

Effect of the Method

The methods may be further characterized by, for example, effect of the method on the number and/or size of gadolinium positive T1 magnetic resonance imaging lesions. For example, in certain embodiments, the patient experiences at least a 5% reduction in the number of gadolinium positive T1 magnetic resonance imaging lesions after receiving for a duration of 24 weeks the compound of Formula I or a pharmaceutically acceptable salt thereof. In certain embodiments, the patient experiences at least a 15% reduction in the number of gadolinium positive T1 magnetic resonance imaging lesions after receiving for a duration of 24 weeks the compound of Formula I or a pharmaceutically acceptable salt thereof. In certain embodiments, the patient experiences at least a 30% reduction in the number of gadolinium positive T1 magnetic resonance imaging lesions after receiving for a duration of 24 weeks the compound of Formula I or a pharmaceutically acceptable salt thereof. In certain embodiments, the patient experiences at least a 50% reduction in the number of gadolinium positive T1 magnetic resonance imaging lesions after receiving for a duration of 24 weeks the compound of Formula I or a pharmaceutically acceptable salt thereof.

In certain embodiments, the patient experiences at least a 5% reduction in the collective size of gadolinium positive T1 magnetic resonance imaging lesions after receiving for a duration of 24 weeks the compound of Formula I or a pharmaceutically acceptable salt thereof. In certain embodiments, the patient experiences at least a 15% reduction in the collective size of gadolinium positive T1 magnetic resonance imaging lesions after receiving for a duration of 24 weeks the compound of Formula I or a pharmaceutically acceptable salt thereof. In certain embodiments, the patient experiences at least a 30% reduction in the collective size of gadolinium positive T1 magnetic resonance imaging lesions after receiving for a duration of 24 weeks the compound of Formula I or a pharmaceutically acceptable salt thereof. In certain embodiments, the patient experiences at least a 50% reduction in the collective size of gadolinium positive T1 magnetic resonance imaging lesions after receiving for a duration of 24 weeks the compound of Formula I or a pharmaceutically acceptable salt thereof.

Fasted State or Fed State of the Patient

The methods may be further characterized by, for example, whether the patient is a in a fasted state or a fed state when the compound of Formula I or pharmaceutically acceptable salt thereof is administered to the patient. In certain embodiments, the patient is in a fasted state when the compound of Formula I or pharmaceutically acceptable salt thereof is administered to the patient. In certain other embodiments, the patient is in a fed state when the compound of Formula I or pharmaceutically acceptable salt thereof is administered to the patient.

Figure 9:
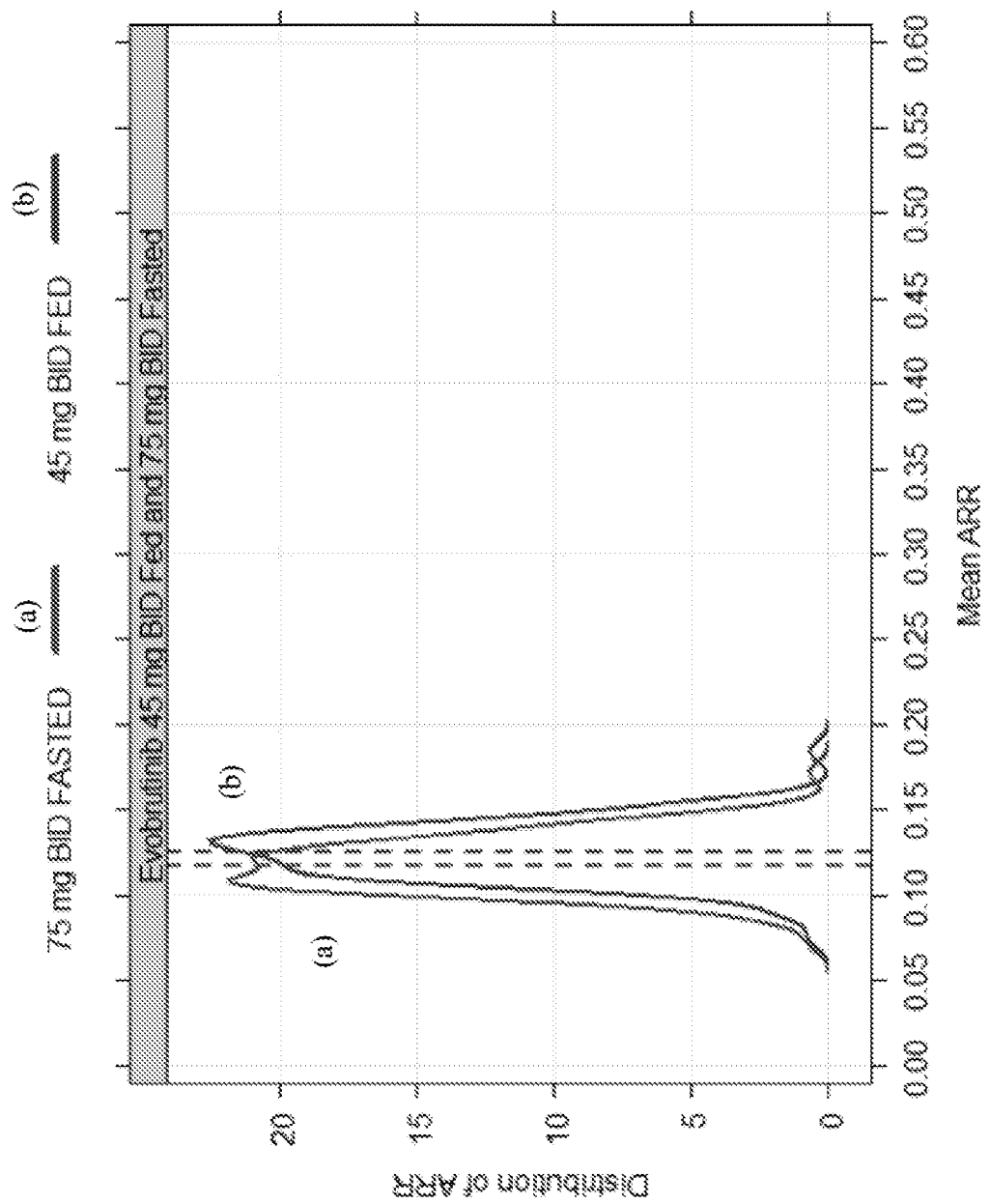
FIG. 9 is a graph depicting simulated distribution of annualized relapse rate for evobrutinib administered at (i) 75 mg BID under fasted state or (ii) 45 mg BID under fed state, as further described in Example 3.

The consumption of food by the patient resulting in a fed state at the time of administering the compound of Formula I or pharmaceutically acceptable salt thereof can facilitate absorption of the compound and, thereby, provide greater bioavailability of the compound. In certain embodiments, the increase in bioavailability of the compound due to the patient being in a fed state can be characterized, such as where there is an increase in bioavailability of the compound by at least 15%, 25%, 35%, 40%, 45% 50%, 55%, 60%, 70%, 75%, 100%, 125%, 150%, 175%, or 200%. As shown in FIG. 9, a twice daily dose of 45 mg of evobrutinib administered under fed state is expected to achieve a level of efficacy that is at least as good as a twice daily dose of 75 mg of evobrutinib administered under fasted state. This is due to a significant increase in bioavailability when switching from fasted to fed state. Accordingly, preferred methods are those where a dose of compound of Formula I or pharmaceutically acceptable salt thereof is administered to the patient according to a protocol in which the dose is taken orally twice daily with food.

A fed state results from the patient consuming food in proximity in time to when the patient receives the compound of Formula I or pharmaceutically acceptable salt thereof. The food is desirably solid food, which may be a meal (e.g., breakfast, lunch, or dinner). The meal may be further characterized by, for example, whether the meal is a light-fat meal or a medium-fat meal. In certain embodiments, the meal is a light-fat meal. In certain embodiments, the meal is a medium-fat meal.

The consumption of food may be characterized by the quantity and/or caloric content consumed by the patient. For example, in certain embodiments, the quantity of food is at least 100 g, 200 g, 300 g, 400 g, or 500 g. In certain embodiments, the food consumed by the patient provides calories in an amount of at least 100, 200, 250, 300, 400, 500, 600, 700, 800, 900, 1000, 1100, 1200, 1500, or 2000 Calories (i.e., kilocalories).

Accordingly, a method described herein can be further characterized by, for example, the feature that said administering is performed at the time the patient consumes a meal. In certain embodiments, the administering is performed within 1 hour of the patient consuming a meal. In certain embodiments, the administering is performed within 1 hour after the patient consumes a meal.

In certain other embodiments, a first unit dosage is administered to the patient at the time the patient consumes a breakfast meal in the morning, and a second unit dosage is administered to the patient at the time the patient consumes a dinner meal in the evening. In certain other embodiments, a first unit dosage is administered to the patient within 1 hour of the time the patient consumes a breakfast meal, and a second unit dosage is administered to the patient within 1 hour of the time the patient consumes a dinner meal. In a preferred embodiment, a first unit dosage is administered to the patient within 1 hour after the patient consumes a breakfast meal, and a second unit dosage is administered to the patient within 1 hour after the patient consumes a dinner meal.

The compound of Formula I or pharmaceutically acceptable salt thereof is desirably administered in the form of a tablet. The tablet is desirably swallowed whole with water by the patient.

Compositions for Medical Use

The invention also provides compositions described herein for use in medicine, such as treatment or prevention of multiple sclerosis as described herein. To illustrate, one aspect of the invention provides a compound of Formula I for oral administration for treating or preventing multiple sclerosis at a daily amount ranging from about 25 mg to about 150 mg or a pharmaceutically acceptable salt thereof, wherein Formula I is represented by:

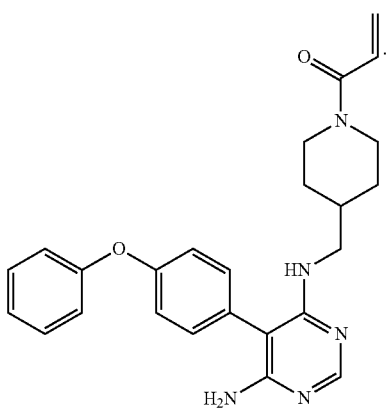 [SMILES: C=CC(=O)N1CCC(CNc2ncnc(N)c2-c2ccc(Oc3ccccc3)cc2)CC1]

The composition for use may be characterized according to features described herein above for methods of treatment. Preferably, the amounts of the compound of Formula I used for preparing the said medicaments are 25, 45, or 75 mg.

Use of Compositions in the Preparation of a Medicament

The invention also provides compositions described herein for use in preparing a medicament for treating or preventing multiple sclerosis. To illustrate, one aspect of the invention provides the use of a compound of Formula I or a pharmaceutically acceptable salt thereof in the preparation of a medicament for treating or preventing multiple sclerosis, wherein the medicament contains the compound of Formula I in an amount ranging from about 25 mg to about 150 mg or a pharmaceutically acceptable salt thereof, the medicament is for oral administration, and Formula I is represented by:

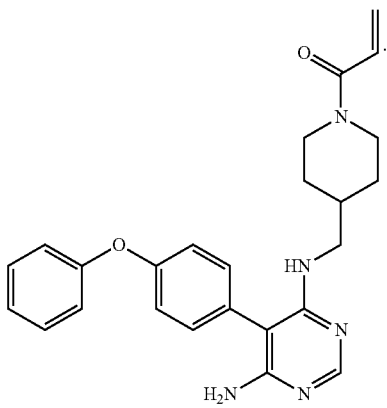 [SMILES: C=CC(=O)N1CCC(CNc2ncnc(N)c2-c2ccc(Oc3ccccc3)cc2)CC1]

The use may be characterized according to features described herein above for methods of treatment. Preferably, the amount of the compound of Formula I used for preparing the said medicament is 25, 45, or 75 mg.

IV. Medical Kits

Another aspect of the invention provides medical kits containing a therapeutic agent and/or pharmaceutical composition described herein, along with instructions for using the kits to treat a disorder described herein. In certain embodiments, the medical kit comprises (i) once daily dosage of a compound of Formula I, as described herein, in an amount ranging from about 50 mg to about 100 mg or a pharmaceutically acceptable salt thereof and (ii) instructions treating or preventing multiple sclerosis. In certain other embodiments, the medical kit comprises (i) a unit dosage containing a compound of Formula I, as described herein, in an amount ranging from about 25 mg to about 50 mg or a pharmaceutically acceptable salt thereof and (ii) instructions treating or preventing multiple sclerosis by orally administering to a patient in need thereof the unit dosage of evobrutinib two times per day. In yet other embodiments, the medical kit comprises (i) compound of Formula I, as described herein, or a pharmaceutically acceptable salt thereof and (ii) instructions for method for treating or preventing multiple sclerosis by orally administering to a patient in need thereof evobrutinib in a daily amount ranging from about 25 mg to about 150 mg or a pharmaceutically acceptable salt thereof.

The medical kit may be further characterized according to one or more of the features described herein in connection with the Therapeutic Applications herein.

V. Pharmaceutical Compositions

Therapeutic agents described herein may be formulated as a pharmaceutical composition comprising a therapeutic agent and a pharmaceutically acceptable carrier.

A compound of the present invention is desirably formulated for oral administration. The compound, as the active ingredient, may be combined in intimate admixture with a pharmaceutical carrier according to conventional pharmaceutical compounding techniques. The carrier may take a variety of forms depending on the desired properties for the oral formulation. In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are used. If desired, tablets may be coated by standard aqueous or nonaqueous techniques. The amount of active compound in such therapeutically useful compositions is such that an effective dosage will be obtained. In certain embodiments, tablet is a film-coated tablet for oral use.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin.

When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The description above describes multiple aspects and embodiments of the invention, including therapeutic methods, pharmaceutical compositions, and medical kits. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and are not intended to limit the invention.

Example 1—Phase I, Double-Blind, Placebo-Controlled Investigation of Safety/Tolerability, Pharmacokinetics (PK) and Effects on QT Interval of Evobrutinib This study was designed to examine the safety and tolerability, pharmacokinetics (PK), and pharmacodynamics (PD) of evobrutinib administered as either single or multiple ascending oral doses, compared with placebo, in healthy subjects. A range of doses administered in a placebo-controlled, double-blind fashion were used to perform early QTc-exposure evaluation for evobrutinib.

Healthy human subjects were administered evobrutinib in a phase I clinical study in two parts. Part 1: 48 participants in six successive dose cohorts (25, 50, 100, 200, 350 and 500 mg of evobrutinib) randomized to a single dose of evobrutinib or placebo. Part 2: 36 subjects in three ascending dose cohorts (25, 75, 200 mg/day op evobrutinib) randomized to evobrutinib or placebo once daily for 14 days.

Trial Design

A randomized, double-blind, placebo-controlled trial conducted in healthy volunteers. The study was carried out in accordance with the principles of the International Conference on Harmonization requirements for Good Clinical Practice, the Declaration of Helsinki, and was reviewed and approved by MidLands Independent Review Board Overland Park, Kans. 66212, USA. Written informed consent was obtained from all participants. The primary endpoint was the safety and tolerability of evobrutinib.

The study was comprised of two distinct parts: Part 1 examined single ascending dose (SAD) of evobrutinib; and Part 2 examined multiple ascending dose (MAD) of evobrutinib, as shown in FIG. 1.

Part 1 involved SAD cohorts of evobrutinib (25, 50, 100, 200, 350 and 500 mg) administered as an oral solution (2.5 mg/mL). In each dose cohort, eight subjects were randomized to receive a single administration of evobrutinib or placebo (6:2) using consecutive randomization codes. A sentinel dosing strategy was employed in all SAD cohorts whereby the first two subjects were initially dosed with evobrutinib or placebo (1:1) on Day 1 with the remainder (5:1) dosed after 24 hours if safety was deemed satisfactory. Subjects remained resident at the trial site until discharge on Day 8 and returned for a follow-up visit between Days 11 and 13. Part 2 examined MAD cohorts of evobrutinib (25, 75, 200 mg) administered once daily over 14 days. In each dose cohort, 12 subjects were randomized to receive evobrutinib or placebo (9:3). Subjects remained resident at the trial site until discharge on Day 18 and returned for a single follow-up visit on Day 28±2 days.

Dose Escalation Criteria

Following completion of each dose cohort in both parts of the study, a safety monitoring committee (SMC) decided whether protocol-defined dose escalation to the next level was appropriate to a maximum of 500 mg in Part 1, or to the highest safe and tolerated dose or highest dose from Part 1 in Part 2, based on all safety data and other available data (including PK and PD data). If two or more subjects per cohort experienced a per-protocol DLE related to evobrutinib, i.e., identification of a non-tolerated dose, dose escalation was to be terminated. DLEs were defined as follows: lymphocyte count decreased to <500/mm$^3$ or increased to >20,000/mm$^3$; severe infection requiring antibiotic and/or antimycotic treatment; alanine aminotransferase or aspartate aminotransferase >3 times the upper limit of normal; adverse events considered related to evobrutinib or placebo with Grade 3/4 toxicity as specified by the Toxicity Grading Scale for Healthy Adult and Adolescent Volunteers Enrolled in Preventative Vaccine Clinical Trials. Other safety data (e.g., hematology parameters) were also taken into consideration for dose escalation decisions as a matter of course.

The decision whether to initiate Part 2 of the study, as well as the MAD starting dose, was determined by the SMC based on review of safety data from Part 1, with PK and PD data also used to inform the decision. Dose-limiting criteria and termination/stopping rules were as per Part 1 of the study. Multiple doses were not to be escalated if three or more subjects per cohort experienced a DLE related to evobrutinib and the maximum daily dose was not to exceed the highest dose given in Part 1. Ultimately, dose levels of 25, 75, and 200 mg were selected.

Subjects

Study participants were healthy male and female subjects aged 18-55 years with a body mass index between 19.0 and 30.0 kg/m$^2$ who had been stable non-smokers for at least 6 months, had no significant clinical abnormalities, and were in good general health.

Safety and Tolerability

In both SAD and MAD cohorts, safety assessments included physical examination, vital signs, 12-lead ECG, 24 hour ECG telemetry and Holter monitoring for QT assessment, clinical laboratory assessments (hematology, biochemistry, coagulation and urinalysis), and assessment of the humoral immune response IgG subclasses). TEAEs and SAEs were recorded from time of informed consent until study completion. Safety and tolerability were assessed in all subjects who had received at least one dose of evobrutinib or placebo with AEs summarized by treatment group, evobrutinib dose level, and system organ class preferred term (MedDRA version 17.0). Assessment of severity considered the Toxicity Grading Scale for Healthy Adult and Adolescent Volunteers Enrolled in Preventative Vaccine Clinical Trials. Data were summarized using descriptive statistics.

PK Assessments and Endpoints

PK analysis was performed in all subjects who received at least one dose of evobrutinib and had at least one primary PK parameter evaluable by non-compartmental methods using PHOENIX® WINNONLIN® Version 6.3 (Certara LP, Princeton, N.J., US). Serial blood samples were obtained on Day 1 pre-dose and 0.25, 0.5, 1.0, 1.5, 2, 2.5, 3, 4, 5, 6, 8, 12, 16, 24 (Day 2), 36 (Day 2), and 48 h (Day 3) post-dose during Part 1, and used to prepare plasma samples for evobrutinib PK analysis. A similar sampling schedule was undertaken in Part 2 on Days 1 and 14, with additional trough samples obtained on Days 5, 8, 11, as well at Day 17 and 18.

PK samples were analyzed by Quintiles Bioanalytical and ADME Laboratory (Ithaca, N.Y., USA) using a validated bioanalytical liquid chromatographic assay with tandem mass spectrometric detection (UPLC-MS/MS) to determine evobrutinib concentration; the LLOQ of the assay was 0.1 ng/mL. Plasma evobrutinib concentrations and PK parameters were summarized descriptively. To test dose proportionality, PK parameters were analyzed graphically as AUC/dose and $C_{max}$/dose and via a power model (PK parameter=$\alpha$*dose$^\beta$) approach with log-transformed PK parameters as the dependent variable and log-transformed dose as the independent variable. Accumulation of evobrutinib and time dependency of PK parameters were evaluated for each dose level during Part 2 using a linear mixed-effect analysis of variance for log-transformed PK parameters with a fixed-repeated effect for day and random effect for subject.

ECG Assessments

Holter ECG recordings of 24 h duration were performed on Day 1 in Parts 1 and 2 of the study using digital 12-lead Holter devices (GI M12R, Manlius, N.Y.) and analyzed in the Quintiles central ECG laboratory. Ten second 12-lead ECGs were extracted in triplicate using Antares ECG extraction software (version 2.15.1.0, AMPS-LLC, New York, N.Y.) for each PK time point (predose and 0.25, 0.5, 1.0, 1.5, 2, 2.5, 3, 4, 5, 6, 8, 12, 16, 24 h postdose) within a −5 to 0 minute window prior to and a 5 minute window after each sampling time point. The quality of extracted ECG snapshots was checked by a Holter Associate/Specialist using the Anatares quality control review interface. The mean QT and RR values from the triplicate ECGs were used to calculate QTcF for each time point.

Concentration-QTcF Analysis

The main endpoint for statistical analysis of ECG data was the relationship between time-matched mean $\Delta$QTcF and evobrutinib plasma concentration after a single dose, with adjustment for the effect of placebo on $\Delta$QTcF (i.e. $\Delta\Delta$QTcF).

A linear modelling approach was conducted using SAS software (version 9.3; SAS-Institute, Cary NC., USA) to explore the relationship between evobrutinib plasma concentration and $\Delta$QTcF. The dataset consisted of Day 1 ECG and PK data from all subjects in Parts 1 and 2 of the study. For the subjects who had received placebo, the evobrutinib concentration data was assumed equal to 0 for the corresponding PK time point. Hysteresis between the plasma concentration of evobrutinib and $\Delta$QTcF was assessed visually by graphical means and tested statistically on the basis of the difference between $\Delta\Delta$QTcF at $T_{max}$ and $\Delta\Delta$QTcF at the timepoint corresponding to largest mean $\Delta\Delta$QTcF. Non-linearity was assessed via visual inspection of the scatterplot of $\Delta$QTcF versus evobrutinib concentration for all time points, and a significance test of the coefficient ($b_2$) for the quadratic term for concentration in a model for $\Delta$QTcF ($\Delta$QTcF=intercept+$b_1$*Concentration+$b_2$*concentration$^2$).

Model derived predicted mean $\Delta\Delta$QTcF was calculated for the geometric mean $C_{max}$ of each dose cohort. Two-sided 90% CIs of the estimate were determined using bootstrapping (1,000 resamples). By-time point analysis of actual values and change from baseline was performed for QTcF. Mean $\Delta\Delta$QTcF with an associated 90% CI was summarized by time point for each dose cohort.

Results

Subject Disposition

In total, 48 subjects (46 males and two females) were randomized into Part 1: six subjects to each evobrutinib dose (25, 50, 100, 200, 350, and 500 mg of evobrutinib), and 12 subjects to placebo. All 48 randomized subjects were treated and completed the trial. Thirty-six subjects were randomized into Part 2: nine subjects to each once daily evobrutinib dose cohort (25, 75, and 200 mg q.d. of evobrutinib), and nine subjects to placebo. All 36 randomized subjects were treated according to protocol. However, two subjects discontinued prematurely from Part 2. One subject on placebo withdrew consent post-dose on Day 14 and one subject on evobrutinib (75 mg) was withdrawn due to non-compliance post-dose on Day 13. Demographic data are summarized in Table 1.

TABLE 1

Baseline Demographics.

| | Part 1 (single-ascending dose study) | | | | | | | Part 2 (multiple-ascending dose study) | | | |
|---|---|---|---|---|---|---|---|---|---|---|---|
| | | Evobrutinib | | | | | | | Evobrutinib | | |
| | Placebo (n = 12) | 25 mg (n = 6) | 50 mg (n = 6) | 100 mg (n = 6) | 200 mg (n = 6) | 350 mg (n = 6) | 500 mg (n = 6) | Placebo (n = 9) | 25 mg (n = 9) | 75 mg (n = 9) | 200 mg (n = 9) |
| Age (years), mean (SD) | 29.5 (10.8) | 30.8 (8.8) | 40.6 (9.6) | 33.2 (9.3) | 31.4 (11.7) | 26.7 (6.3) | 32.0 (10.6) | 33.0 (13.3) | 32.2 (6.6) | 36.7 (9.0) | 35.1 (7.2) |
| Males, n (%) | 12 (100) | 6 (100) | 4 (66.7) | 6 (100) | 6 (100) | 6 (100) | 6 (100) | 9 (100) | 9 (100) | 8 (88.9) | 9 (100) |
| Females, n (%) | 0 (0) | 0 (0) | 2 (33.3) | 0 (0) | 0 (0) | 0 (0) | 0 (0) | 0 (0) | 0 (0) | 1 (11.1) | 0 (0) |
| Race, n (%) | | | | | | | | | | | |
| White | 10 (83.3) | 4 (66.7) | 6 (100) | 5 (83.3) | 4 (66.7) | 6 (100) | 3 (50.0) | 5 (55.6) | 3 (33.3) | 4 (44.4) | 5 (55.6) |
| Black/African-American | 1 (8.3) | 2 (33.3) | 0 (0) | 1 (16.7) | 2 (33.3) | 0 (0) | 3 (50.0) | 3 (33.3) | 6 (66.7) | 3 (33.3) | 4 (44.4) |
| Other | 1 (8.3) | 0 (0) | 0 (0) | 0 (0) | 0 (0) | 0 (0) | 0 (0) | 1 (11.1) | 0 (0) | 2 (22.2) | 0 (0) |
| BMI (mg/kg$^2$), mean (SD) | 25.6 (2.8) | 24.8 (3.9) | 26.6 (3.3) | 26.3 (3.1) | 26.1 (2.4) | 22.7 (3.5) | 25.4 (2.2) | 25.8 (2.9) | 25.6 (1.3) | 25.8 (2.4) | 26.0 (2.5) |

BMI, body mass index; SD, standard deviation.

Safety and Tolerability Assessment

All randomized subjects were included in the safety analysis. Analysis of treatment-emergent adverse events (TEAEs) following single and multiple dosing are shown in Table 2 and Table 3, respectively. There were no deaths or serious adverse events (SAEs) related to treatment. A single SAE of multi-trauma due to an automobile accident was experienced by a subject in the evobrutinib 350 mg single ascending dose cohort 7 days after study administration, but was unrelated to the study drug.

TABLE 2

Treatment-emergent adverse events in Part 1 (single ascending dose study).

| Preferred Term, n (%), [TEAEs] | Placebo (n = 12) | Evobrutinib | | | | | | Pooled active (n = 36) |
| --- | --- | --- | --- | --- | --- | --- | --- | --- |
| | | 25 mg (n = 6) | 50 mg (n = 6) | 100 mg (n = 6) | 200 mg (n = 6) | 350 mg (n = 6) | 500 mg (n = 6) | |
| Overall total | 4 (33.3) [6] | 0 (0.0) | 3 (50.0) [6] | 1 (16.7) [1] | 2 (33.3) [4] | 1 (16.7) [1] | 2 (33.3) [3] | 9 (25.5) [15] |
| Headache | 1 (8.3) [1] | 0 (0.0) | 1 (16.7) [2] | 0 (0.0) | 0 (0.0) | 0 (0.0) | 1 (16.7) [2] | 2 (5.6) [3] |
| Contact dermatitis | 0 (0.0) | 0 (0.0) | 2 (33.3) [2] | 0 (0.0) | 0 (0.0) | 0 (0.0) | 0 (0.0) | 2 (5.6) [2] |
| Amylase increased | 0 (0.0) | 0 (0.0) | 0 (0.0) | 0 (0.0) | 1 (16.7) [1] | 0 (0.0) | 0 (0.0) | 1 (2.8) [1] |
| Back pain | 0 (0.0) | 0 (0.0) | 1 (16.7) [1] | 0 (0.0) | 0 (0.0) | 0 (0.0) | 0 (0.0) | 1 (2.8) [1] |
| Dizziness | 0 (0.0) | 0 (0.0) | 0 (0.0) | 0 (0.0) | 1 (16.7) [1] | 0 (0.0) | 0 (0.0) | 1 (2.8) [1] |
| Dry eye | 0 (0.0) | 0 (0.0) | 0 (0.0) | 0 (0.0) | 0 (0.0) | 0 (0.0) | 1 (16.7) [1] | 1 (2.8) [1] |
| Dyspepsia | 0 (0.0) | 0 (0.0) | 1 (16.7) [1] | 0 (0.0) | 0 (0.0) | 0 (0.0) | 0 (0.0) | 1 (2.8) [1] |
| Excoriation | 0 (0.0) | 0 (0.0) | 0 (0.0) | 0 (0.0) | 1 (16.7) [1] | 0 (0.0) | 0 (0.0) | 1 (2.8) [1] |
| Lipase increased | 0 (0.0) | 0 (0.0) | 0 (0.0) | 0 (0.0) | 1 (16.7) [1] | 0 (0.0) | 0 (0.0) | 1 (2.8) [1] |
| Multiple injuries | 0 (0.0) | 0 (0.0) | 0 (0.0) | 0 (0.0) | 0 (0.0) | 1 (16.7) [1] | 0 (0.0) | 1 (2.8) [1] |
| Nasal congestion | 0 (0.0) | 0 (0.0) | 0 (0.0) | 1 (16.7) [1] | 0 (0.0) | 0 (0.0) | 0 (0.0) | 1 (2.8) [1] |
| Odynophagia | 0 (0.0) | 0 (0.0) | 0 (0.0) | 0 (0.0) | 0 (0.0) | 0 (0.0) | 1 (16.7) [1] | 1 (2.8) [1] |
| Abdominal pain | 1 (8.3) [1] | 0 (0.0) | 0 (0.0) | 0 (0.0) | 0 (0.0) | 0 (0.0) | 0 (0.0) | 0 (0.0) |
| Application site pruritus (due to ECG stickers) | 1 (8.3) [1] | 0 (0.0) | 0 (0.0) | 0 (0.0) | 0 (0.0) | 0 (0.0) | 0 (0.0) | 0 (0.0) |
| Dry mouth | 1 (8.3) [1] | 0 (0.0) | 0 (0.0) | 0 (0.0) | 0 (0.0) | 0 (0.0) | 0 (0.0) | 0 (0.0) |
| Noncardiac chest pain | 1 (8.3) [1] | 0 (0.0) | 0 (0.0) | 0 (0.0) | 0 (0.0) | 0 (0.0) | 0 (0.0) | 0 (0.0) |
| Upper respiratory tract infection | 1 (8.3) [1] | 0 (0.0) | 0 (0.0) | 0 (0.0) | 0 (0.0) | 0 (0.0) | 0 (0.0) | 0 (0.0) |

TABLE 3

Treatment-emergent adverse events in Part 2 (multiple ascending dose study).

| Preferred Term, n (%), [TEAEs] | Placebo (n = 9) | Evobrutinib | | | Pooled active (n = 27) |
| --- | --- | --- | --- | --- | --- |
| | | 25 mg (n = 9) | 75 mg (n = 9) | 200 mg (n = 9) | |
| Overall total | 2 (22.2) [2] | 3 (33.3) [6] | 7 (77.8) [14] | 3 (33.3) [3] | 13 (48.1) [23] |
| Headache | 1 (11.1) [1] | 1 (11.1) [1] | 2 (22.2) [2] | 0 (0.0) | 3 (11.1) [3] |
| Application site irritation | 0 (0.0) | 0 (0.0) | 1 (11.1) [1] | 1 (11.1) [1] | 2 (7.4) [2] |
| Fatigue | 0 (0.0) | 0 (0.0) | 2 (22.2) [2] | 0 (0.0) | 2 (7.4) [2] |
| Upper respiratory tract infection | 0 (0.0) | 0 (0.0) | 1 (11.1) [1] | 1 (11.1) [1] | 2 (7.4) [2] |
| Abdominal pain | 0 (0.0) | 0 (0.0) | 1 (11.1) [2] | 0 (0.0) | 1 (3.7) [2] |
| Nausea | 0 (0.0) | 0 (0.0) | 1 (11.1) [2] | 0 (0.0) | 1 (3.7) [2] |
| Abdominal discomfort | 0 (0.0) | 1 (11.1) [1] | 0 (0.0) | 0 (0.0) | 1 (3.7) [1] |
| Complex regional pain | 0 (0.0) | 1 (11.1) [1] | 0 (0.0) | 0 (0.0) | 1 (3.7) [1] |
| Constipation | 0 (0.0) | 0 (0.0) | 1 (11.1) [1] | 0 (0.0) | 1 (3.7) [1] |
| Dry throat | 0 (0.0) | 0 (0.0) | 1 (11.1) [1] | 0 (0.0) | 1 (3.7) [1] |
| Excoriation | 0 (0.0) | 1 (11.1) [1] | 0 (0.0) | 0 (0.0) | 1 (3.7) [1] |

TABLE 3-continued

Treatment-emergent adverse events in Part 2 (multiple ascending dose study).

| | | Evobrutinib | | | |
|---|---|---|---|---|---|
| Preferred Term, n (%), [TEAEs] | Placebo (n = 9) | 25 mg (n = 9) | 75 mg (n = 9) | 200 mg (n = 9) | Pooled active (n = 27) |
| Muscle spasms | 0 (0.0) | 0 (0.0) | 1 (11.1) [1] | 0 (0.0) | 1 (3.7) [1] |
| Muscle strain | 0 (0.0) | 1 (11.1) [1] | 0 (0.0) | 0 (0.0) | 1 (3.7) [1] |
| Rhinorrhea | 1 (11.1) [1] | 1 (11.1) [1] | 0 (0.0) | 0 (0.0) | 1 (3.7) [1] |
| Sneezing | 0 (0.0) | 0 (0.0) | 1 (11.1) [1] | 0 (0.0) | 1 (3.7) [1] |
| Toothache | 0 (0.0) | 0 (0.0) | 0 (0.0) | 1 (11.1) [1] | 1 (3.7) [1] |

ECG, electrocardiogram; TEAE, treatment-emergent adverse event

Overall, the nature and incidence of TEAEs were similar in evobrutinib-treated and placebo-treated subjects after single dosing in Part 1. In total, 15 TEAEs developed in nine (25.0%) subjects receiving evobrutinib and six TEAEs in four (33.3%) subjects on placebo. The most common TEAEs in subjects on evobrutinib were headache (three events in two [5.6%] subjects) and contact dermatitis at locations of electrocardiogram (ECG) pads (two events in two [5.6%] subjects). Headache also occurred in one subject (8.3%) on placebo. All TEAEs were mild (Grade 1) except in one subject in the 200 mg treatment group, who experienced a dose-limiting TEAE of Grade 4 increased lipase in combination with Grade 3 increased amylase on Day 11. However, there were no accompanying clinical signs and symptoms, ultrasound examination of the abdomen revealed no abnormality of the pancreas, and values returned rapidly to baseline by Day 12.

In Part 2, 23 TEAEs occurred in 13 (48.1%) subjects on evobrutinib with two TEAEs reported in two (22.2%) subjects on placebo. The most frequently reported TEAEs on evobrutinib included headache (three events in three [11.1%] of subjects versus one event [11.1%] on placebo), and skin irritation due to ECG pads, fatigue and upper respiratory tract infection (each two events in two [7.4%] subjects). Seven gastrointestinal TEAEs occurred in five (18.5%) evobrutinib-treated subjects. No relation to dose was observed for gastrointestinal or other TEAEs. All TEAEs reported were mild and no dose-limiting adverse events were reported.

There were no TEAEs leading to discontinuation and no clinically significant trends in vital signs, ECGs, laboratory values or immunoglobulin G (IgG) subclasses in either part of the study. Overall, evobrutinib appeared to be safe and well tolerated and no non-tolerated dose could be defined after single or multiple ascending dose administrations, supporting further clinical investigation of evobrutinib in forthcoming trials.

PK Assessment

Figure 2A:
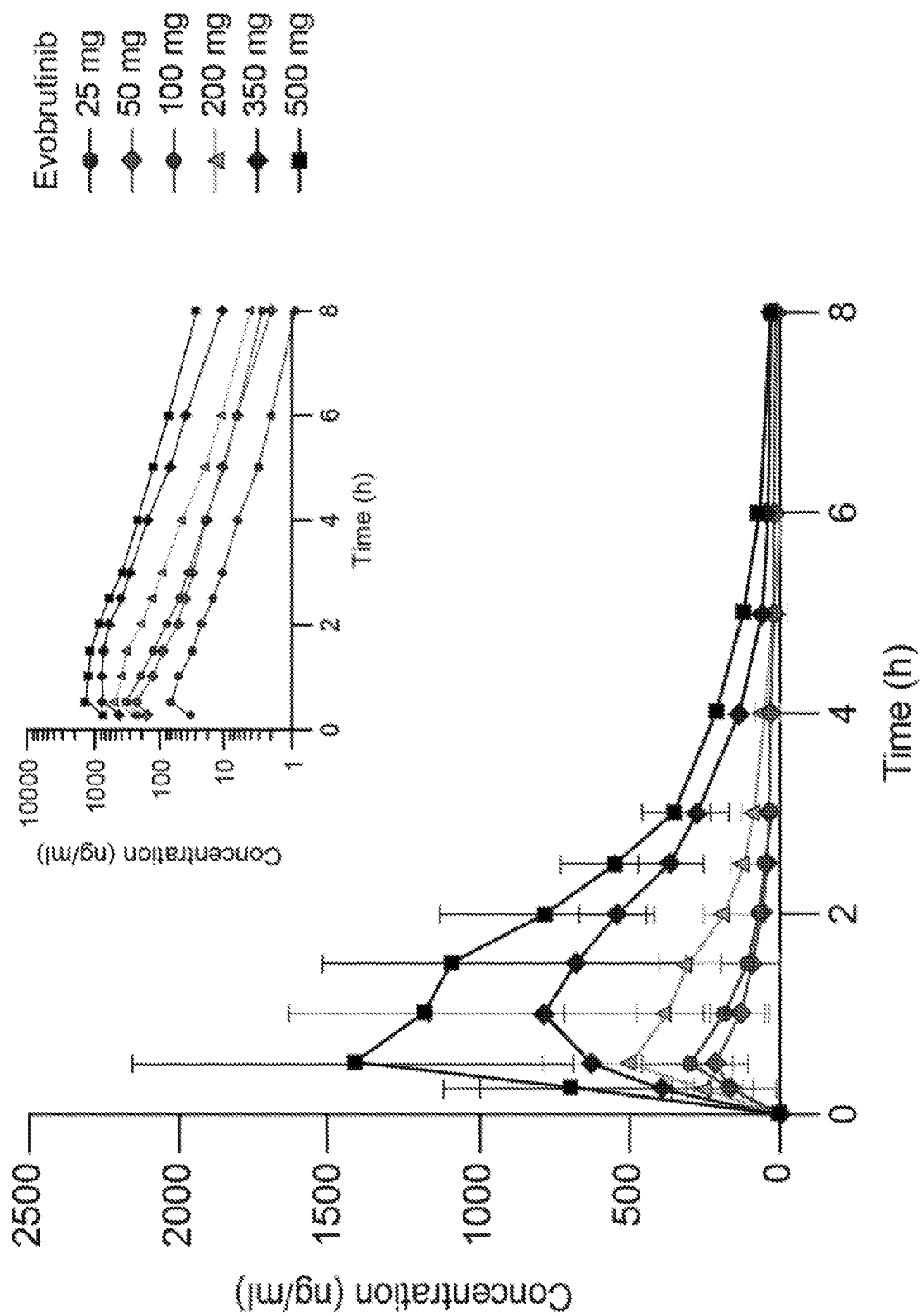
FIG. 2A provides graphs depicting pharmacokinetic data for evobrutinib in the form of arithmetic mean (SD) evobrutinib serum exposure versus time after single dosing on Day 1 of Part 1 (single ascending dose study), as further described in Example 1.

Following single dosing in Part 1, evobrutinib was rapidly absorbed with a median $T_{max}$ (time to maximum observed concentration [$C_{max}$]) of 0.5 to 1.0 h across all dose cohorts, 25-500 mg, as shown in Table 4. After reaching $C_{max}$, the plasma concentration of evobrutinib declined rapidly and dose-independently in a mono-exponential fashion to less than 1% of $C_{max}$ within 8 h, as shown in FIG. 2A. At the two higher single doses (350 and 500 mg), evobrutinib concentrations above the lower limit of quantification (LLOQ) were still measurable up to 48 h after dosing in some (n=3) subjects, revealing an additional terminal phase in the elimination of evobrutinib.

For this reason, the estimated apparent geometric mean terminal half-life ($t_{1/2}$) was smaller with lower doses of evobrutinib (25-200 mg) compared with the two higher doses (1.8-2.6 vs 6.6-6.8 h, respectively). As a consequence of the longer terminal t½ at 350 mg and 500 mg, geometric mean apparent volume of distribution during the terminal phase ($V_z/F$) was 1,796 and 1,485 L, respectively. Nevertheless, the increase in $t_{1/2}$ was not reflected in changes in mean residence time, MRT, as shown in Table 4, and all concentration-time profiles declined at the same rate within the first 8 h, with a relevant $t_{1/2}$ of ~2 h and a relevant $V_z/F$ of approximately 650 L for all doses. Apparent clearance (CL/F) was high (2,553-3,995 mL/min) and independent of dose.

Figure 2B:
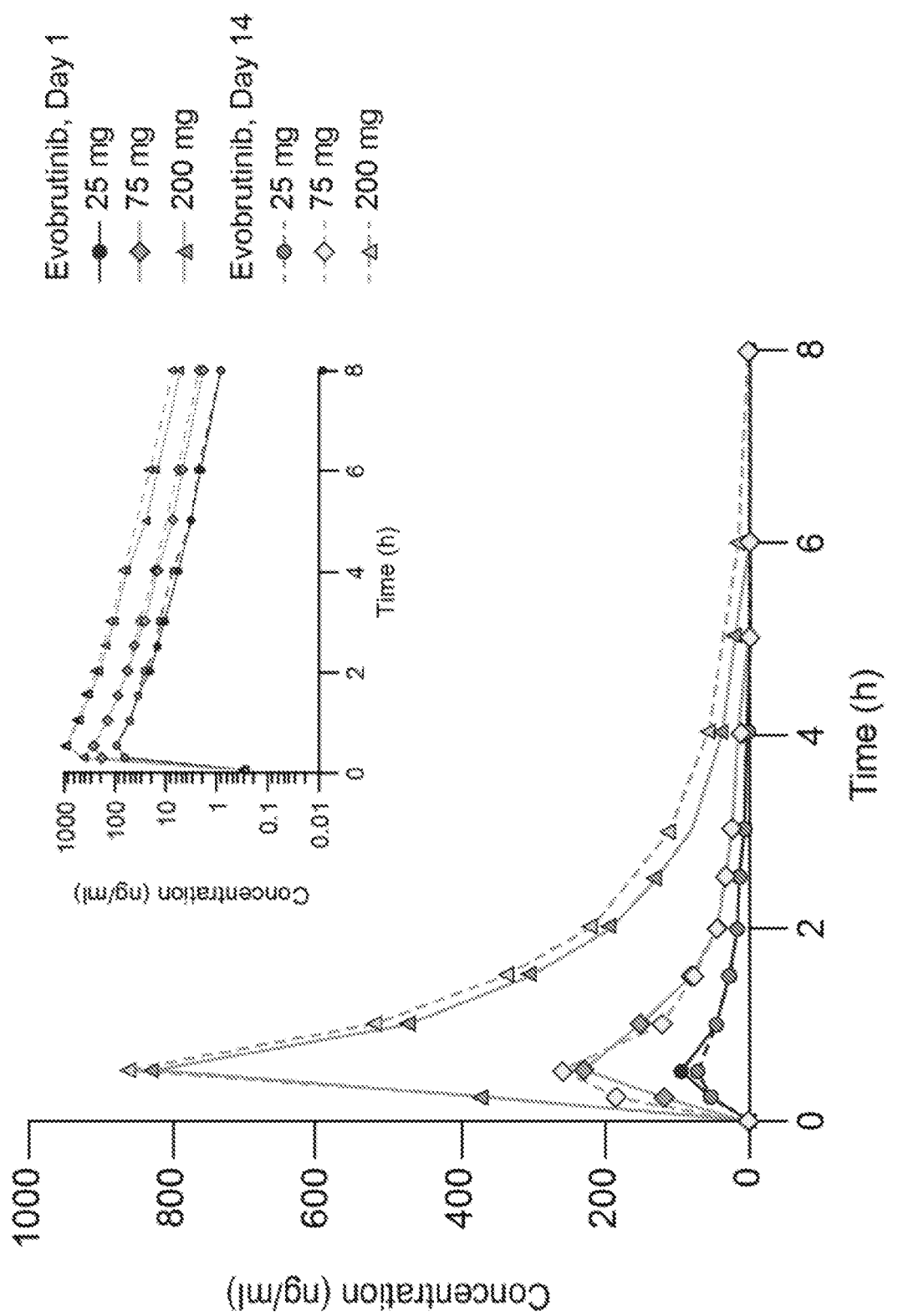
FIG. 2B provides graphs depicting pharmacokinetic data for evobrutinib in the form of mean evobrutinib serum exposure versus time on Day 1 and Day 14 of Part 2 (multiple ascending dose study), as further described in Example 1.

In Part 2, concentration-time profiles were similar between Day 1 and Day 14 indicating no accumulation with multiple dosing, as shown in FIG. 2B. This was confirmed by accumulation ratios for area under the concentration curve (AUC) ($R_{acc(AUC0-24h)}$ 1.03-1.09) and $C_{max}$ ($R_{acc(Cmax)}$ 0.81-1.00) and was in agreement with the observed short t½ (1.6-3.6 h) after multiple dosing. In general, PK parameters determined on Day 1 and Day 14 of the multiple dose study agreed with those obtained after single dosing in Part 1, as shown in Table 4.

Figure 3A:
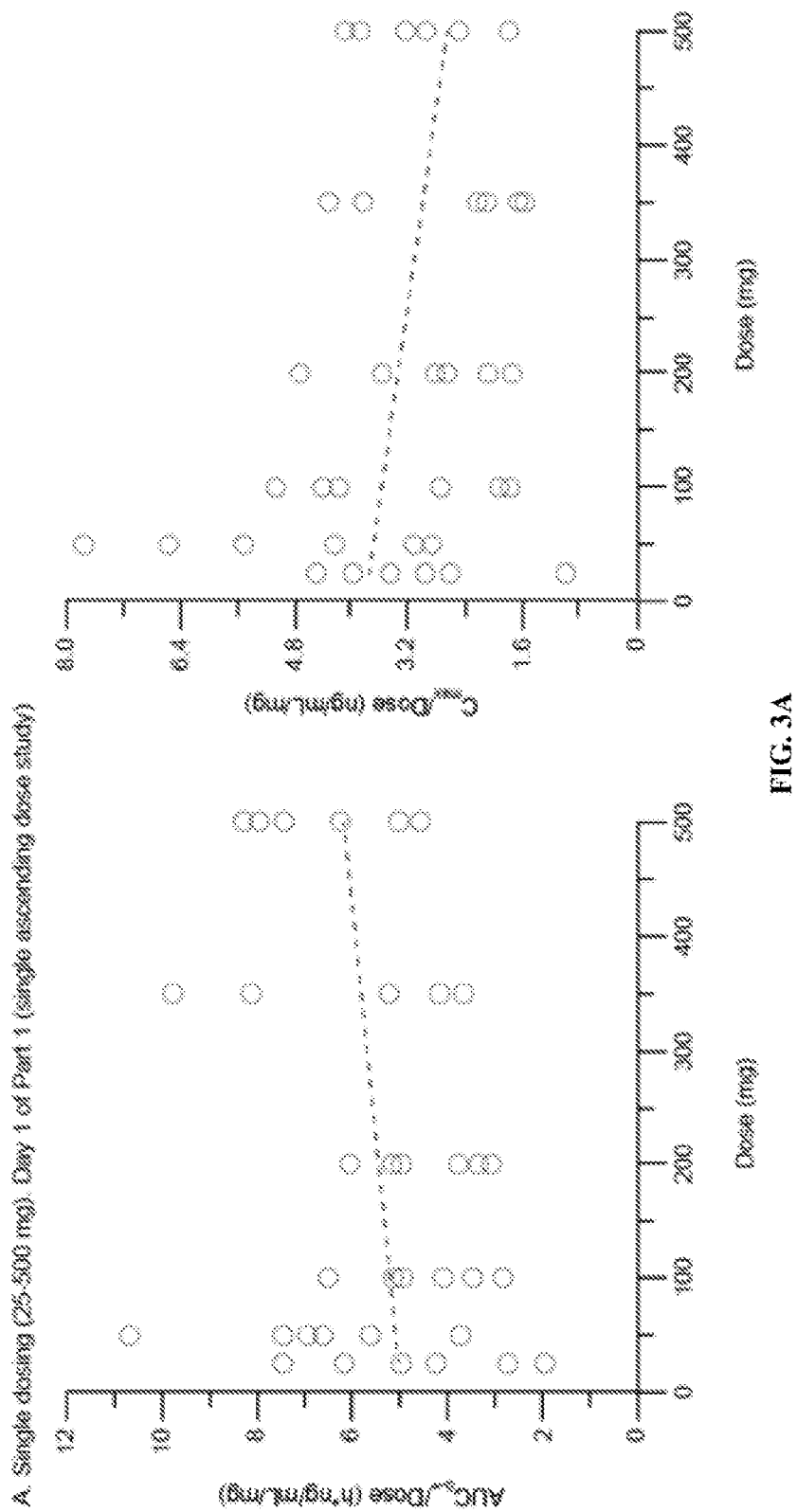
FIG. 3A provides graphs depicting individual dose-normalized evobrutinib exposure (AUC and $C_{max}$) after single dosing on Day 1 of Part 1 (single ascending dose study), as further described in Example 1.
Figure 3B:
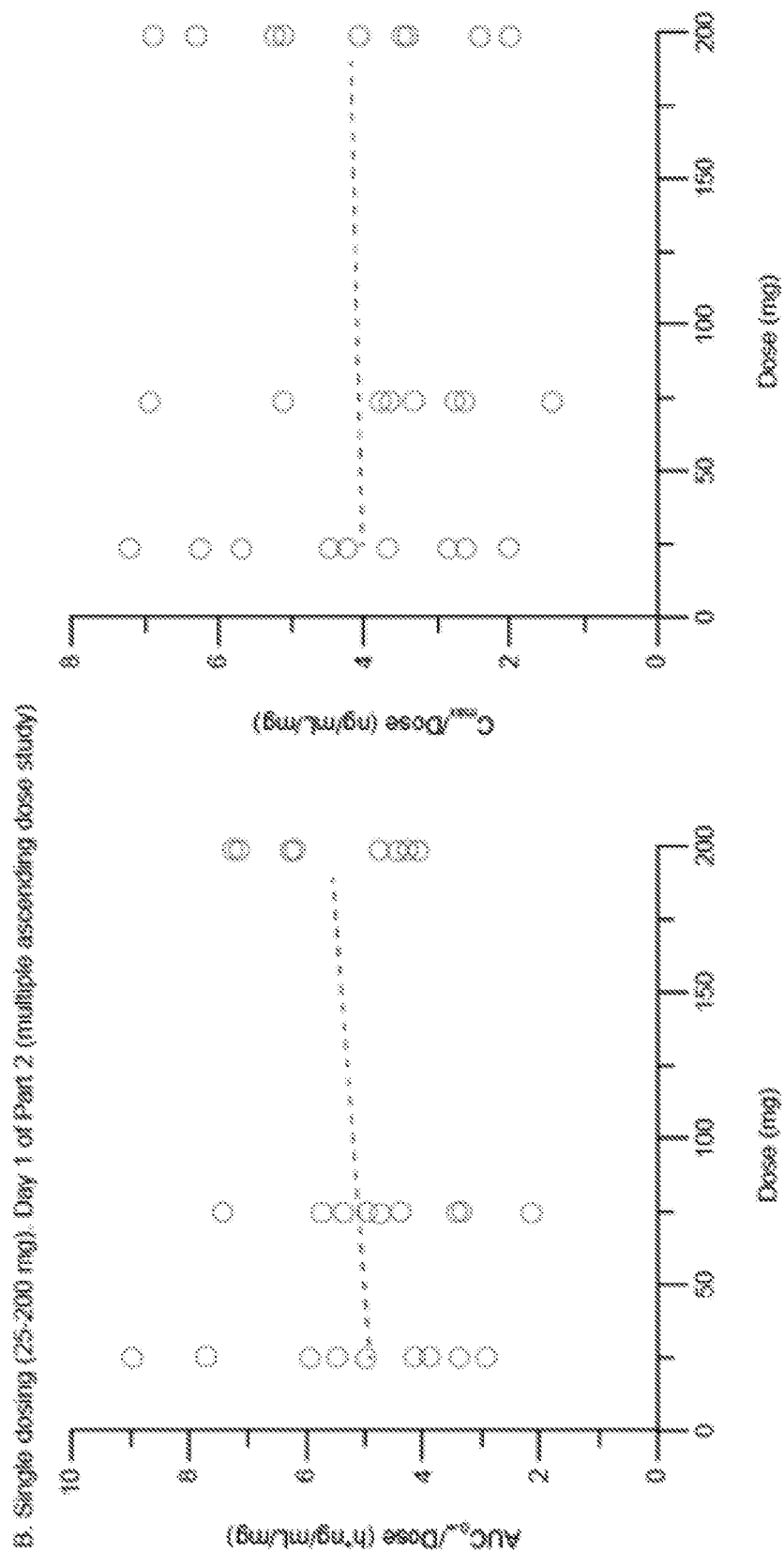
FIG. 3B provides graphs depicting individual dose-normalized evobrutinib exposure (AUC and $C_{max}$) after single dosing on Day 1 of Part 2 (multiple ascending dose study), as further described in Example 1.
Figure 3C:
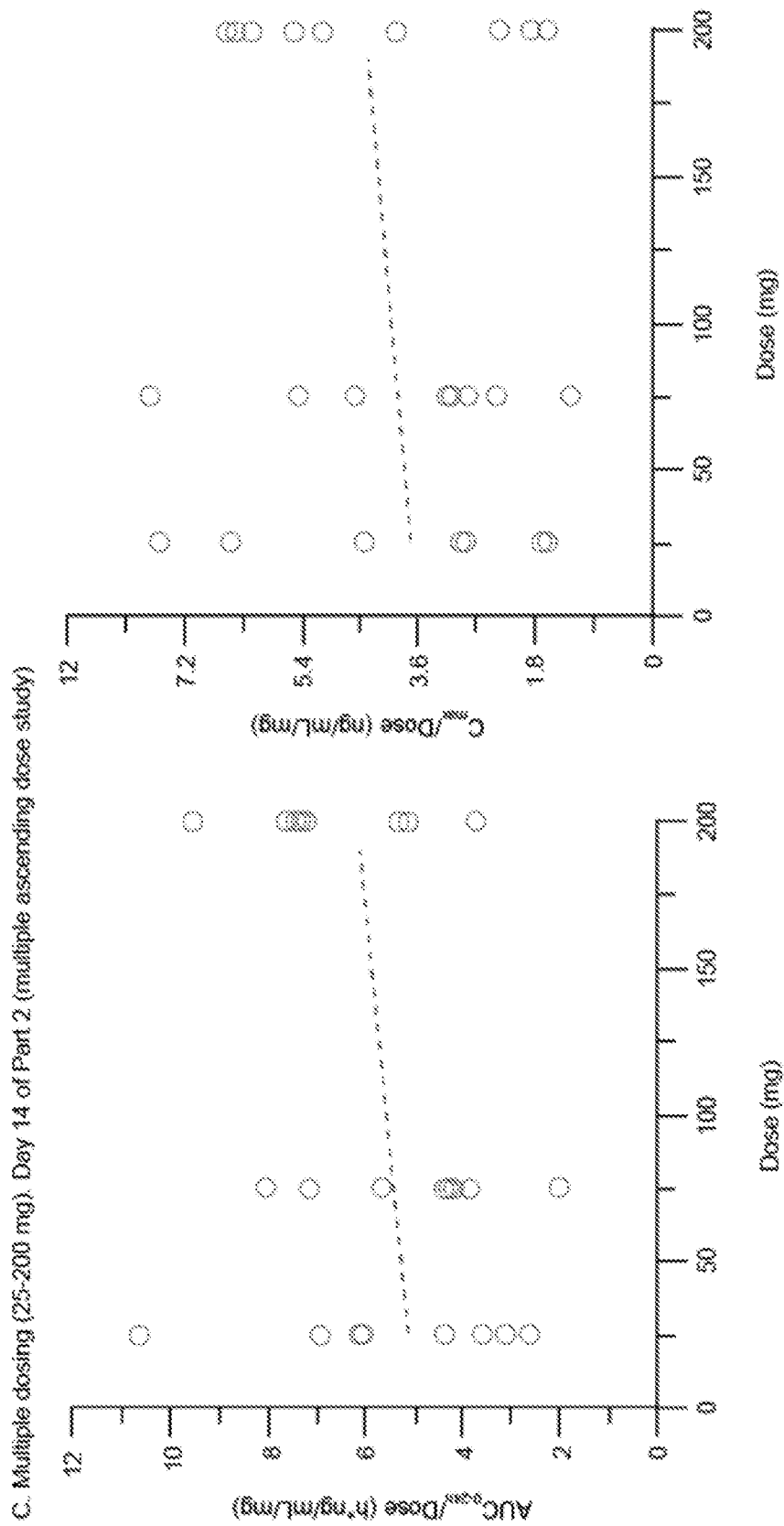
FIG. 3C provides graphs depicting individual dose-normalized evobrutinib exposure (AUC and $C_{max}$) after multiple dosing on Day 14 of Part 2 (multiple ascending dose study), as further described in Example 1.

An apparent increase in $t_{1/2}$ with dose was not aligned with MRT, and was not deemed clinically relevant. Dose proportionality of AUC from time 0 to 24 h ($AUC_{0-24h}$) and $C_{max}$ was demonstrated following multiple dosing of 25-200 mg, as shown in FIG. 3B, and confirmed by the power model. Furthermore, no time dependency of the evobrutinib PK was noted based on the comparison of concentration-time profiles. This was confirmed by $AUC_{0-24h}$ on Day 14 to AUC from time 0 extrapolated to infinity ($AUC_{0-\infty}$) on Day 1, with 90% confidence interval (CI) including 100% across all comparisons.

TABLE 4

Geometric Mean (CV % GM) PK Parameters of Evobrutinib.

| Following single-dose administration | | | | | | | | |
|---|---|---|---|---|---|---|---|---|
| Dose [mg] | N | $AUC_{0-\infty}$ [ng * h/mL] | $C_{max}$ [ng/mL] | $T_{max}$* [h] | $T_{1/2}$ [h] | MRT [h] | CL/F [mL/min] | $V_z/F$ [L] |
| 25 | 6 | 104 (53.6) | 69.9 (58.1) | 0.8 (0.5-1.0) | 1.80 (12.8) | 1.82 (0.41) | 4,000 (53.6) | 621 (60.2) |

TABLE 4-continued

Geometric Mean (CV % GM) PK Parameters of Evobrutinib.

| | | | | | | | | |
|---|---|---|---|---|---|---|---|---|
| 50 | 6 | 326 | 234 | 0.5 | 2.06 | 1.82 | 2,550 | 455 |
| | | (35.7) | (42.1) | (0.3-1.0) | (36.8) | (0.37) | (35.7) | (24.5) |
| 100 | 6 | 434 | 309 | 0.5 | 2.56 | 1.70 | 3,840 | 850 |
| | | (30.3) | (47.5) | (0.3-0.5) | (39.0) | (0.18) | (30.3) | (48.5) |
| 200 | 6 | 856 | 555 | 0.5 | 2.09 | 1.80 | 3,900 | 703 |
| | | (27.0) | (37.2) | (0.5-1) | (5.30) | (0.33) | (27.0) | (24.7) |
| 350 | 6 | 1,910 | 846 | 1.0 | 6.81 | 2.26 | 3,050 | 1800 |
| | | (41.7) | (44.7) | (0.3-2) | (95.0) | (0.58) | (41.7) | (136) |
| 500 | 6 | 3,220 | 1510 | 0.5 | 6.63 | 2.19 | 2,590 | 1490 |
| | | (25.0) | (34.7) | (0.5-2) | (69.9) | (0.28) | (25.0) | (64.6) |

On Day 1 and Day 14 of the multiple-dose study

| Dose [mg] | N | $AUC_{0-\infty}$ [ng*h/mL] | $C_{max}$ [ng/mL] | $T_{max}$* [h] | $T_{1/2}$ [h] | MRT [h] | CL/F [mL/min] | $V_z/F$ [L] |
|---|---|---|---|---|---|---|---|---|
| Day 1 | | | | | | | | |
| 25 | 9 | 123 | 99.7 | 0.5 | 1.70 | 1.66 | 3,390 | 498 |
| | | (38.7) | (44.5) | (0.3-0.5) | (19.9) | (0.24) | (38.7) | (32.9) |
| 75 | 9 | 325 | 254 | 0.5 | 1.86 | 1.67 | 3850 | 620 |
| | | (37.5) | (46.0) | (0.3-1) | (15.1) | (0.28) | (37.5) | (48.6) |
| 200 | 9 | 1110 | 797 | 0.5 | 2.49 | 1.72 | 3,000 | 647 |
| | | (24.6) | (43.9) | (0.5-1) | (34.7) | (0.21) | (24.6) | (42.3) |

| Dose [mg] | N | $AUC_{0-24h}$ [ng*h/mL] | $C_{max}$ [ng/mL] | $T_{max}$* [h] | $T_{1/2}$ [h] | MRT [h] | $R_{acc(Cmax)}$[+] | $R_{acc(AUC0-24h)}$[+] |
|---|---|---|---|---|---|---|---|---|
| Day 14 | | | | | | | | |
| 25 | 9 | 126 | 80.4 | 0.5 | 1.59 | 1.81 | 0.807 | 1.03 |
| | | (46.4) | (64.9) | (0.3-1) | (18.2) | (0.29) | (0.59-1.11) | (0.89-1.17) |
| 75 | 8 | 345 | 252 | 0.5 | 2.29 | 1.79 | 1.00 | 1.03 |
| | | (44.6) | (60.3) | (0.3-1) | (18.9) | (0.25) | (0.65-1.54) | (0.81-1.31) |
| 200 | 9 | 1,210 | 782 | 0.5 | 3.62 | 1.92 | 0.982 | 1.09 |
| | | (34.0) | (60.1) | (0.5-1) | (70.5) | (0.21) | (0.71-1.35) | (0.94-1.25) |

Geometric mean (CV % GM) values are rounded to 3 significant digits.
*Median and range; rounded to 1 significant digit.
[+]Geometric mean and 95% confidence interval.

$AUC_{0-\infty}$, area under the plasma concentration-time curve from time zero extrapolated to infinity; $AUC_{0-24h}$, area under the plasma concentration-time curve from time zero to 24 h; CL/f, apparent clearance; $C_{max}$, maximum observed plasma concentration; CV % GM, geometric coefficient of variation; MRT, mean residence time; $R_{acc(AUC0-24)}$, accumulation ratio for AUC; $R_{acc(Cmax)}$, accumulation ratio for $C_{max}$; $T_{max}$, time to reach maximum plasma concentration; $T_{1/2}$, apparent terminal half-life; $V_z/f$, apparent volume of distribution during terminal phase.

ECG Assessment

ECG assessment was based on a dataset of 83 subjects, which included two subjects with missing baseline data. (ECG data from one of the 84 randomized subjects was not evaluable due to the presence of flat T waves in all leads and this subject was excluded from the analysis.)

Concentration-QT Analysis

Visual inspection of hysteresis effect indicated markedly different profiles for evobrutinib concentration and mean change from baseline in the QT interval corrected by Fridericia's formula (ΔQTcF) over time, with the peak in mean ΔQTcF occurring later than the peak in mean evobrutinib concentration. However, a statistical test based on placebo-adjusted ΔQTcF (ΔΔQTcF) indicated no evidence of hysteresis between the plasma concentration of evobrutinib and ΔQTcF. Non-linearity was not observed on visual inspection of the ΔQTcF versus evobrutinib plasma concentration data or using a significance test of the quadratic term for concentration in a model for ΔQTcF. In the absence of hysteresis and nonlinearity, further modelling of the annualized relapse rate analysis was conducted based on a linear mixed-effects model for ΔQTcF that included concentration, treatment and time as fixed effects and subject-specific slope and intercept as random effects, based on previous publications (see, e.g., Garnett C. E., et al. in *J. Clin. Pharmacol.* 48, 13-18 (2008); Zhang J. et al. in *Therap. Innovation. Reg. Sci.* 49, 392-397 (2015); and Westerberg G., et al. in *Br. J. Clin. Pharmacol.* 79, 477-491 (2014)).

Figure 4:
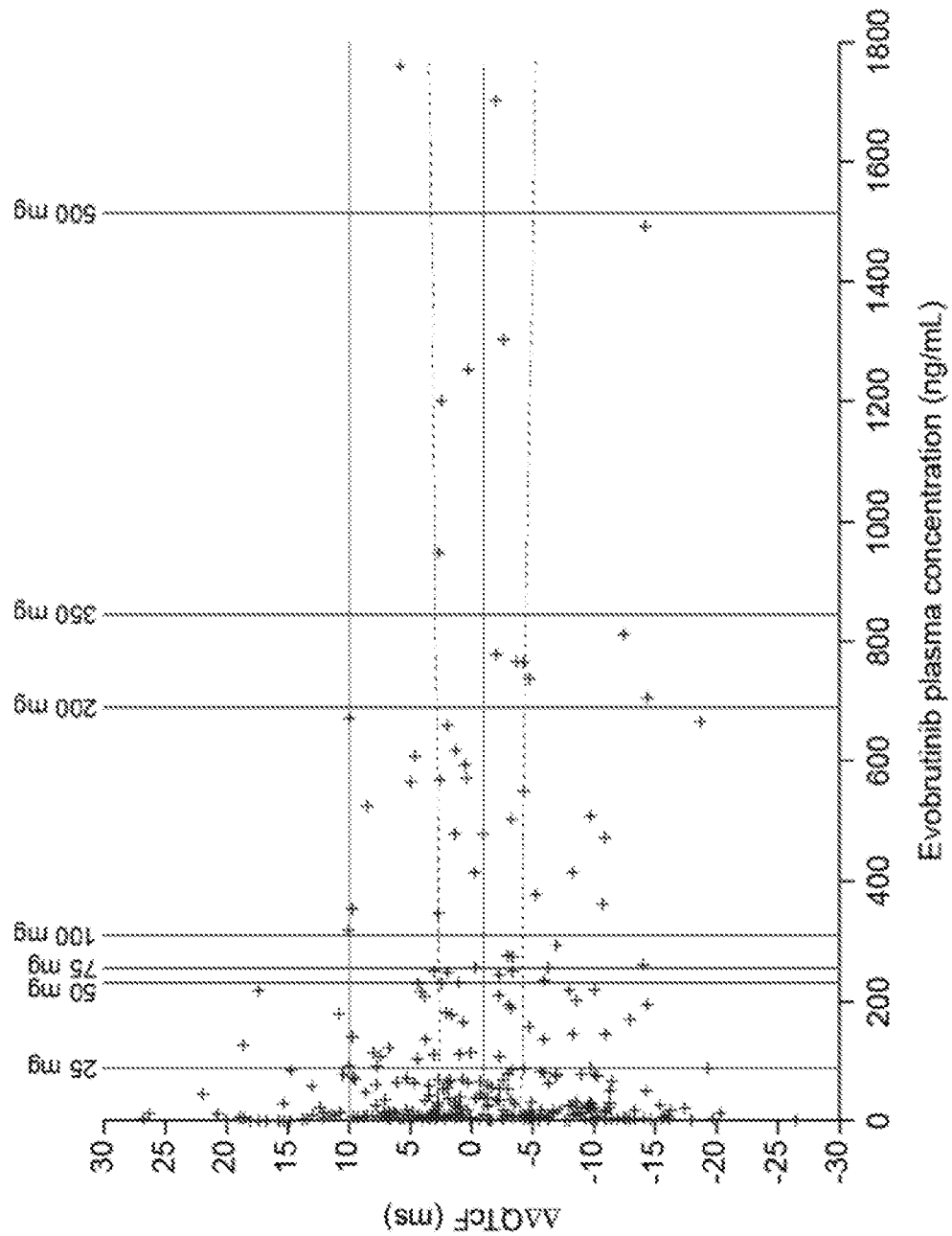
FIG. 4 is a plot depicting the relationship between evobrutinib concentration and ΔΔQTcF, as further described in Example 1.

The slope of the relationship between placebo-adjusted ΔQTcF and concentration was negative and very close to zero (−0.00027 ms/ng per mL; P=0.86), as shown in FIG. 4. The predicted population mean ΔΔQTcF at geometric mean $C_{max}$ for the 25 mg group (86.5 ng/mL) was −0.78 ms with an upper limit of 2.71 ms for the 90% two-sided bootstrapped CI, as shown in Table 5. For the 500 mg dose group, the predicted population mean ΔΔQTcF at geometric mean $C_{max}$ (1,512 ng/mL) was −1.16 ms with an upper limit of 3.26 ms for the 90% CI, which is well below the 10 ms threshold of regulatory concern (ICH-E14 guidance).

TABLE 5

Predicted Values of Mean ΔΔQTcF and Associated Two-sided 90% Cis. By evobrutinib plasma concentration

| | Geometric mean | Predicted mean | 90% CI of ΔΔQTcF [ms] (Bootstrapped) | |
|---|---|---|---|---|
| Dose [mg] | $C_{max}$ [ng/ml] | ΔΔQTcF* [ms] | Lower bound | Upper bound |
| 25 | 86.48 | −0.78 | −4.22 | 2.71 |
| 50 | 233.9 | −0.82 | −4.23 | 2.66 |

TABLE 5-continued

Predicted Values of Mean ΔΔQTcF and Associated Two-sided 90% CIs.
By evobrutinib plasma concentration

| Dose [mg] | Geometric mean $C_{max}$ [ng/ml] | Predicted mean ΔΔQTcF* [ms] | 90% CI of ΔΔQTcF [ms] (Bootstrapped) | |
|---|---|---|---|---|
| | | | Lower bound | Upper bound |
| 75 | 253.9 | −0.82 | −4.23 | 2.66 |
| 100 | 308.6 | −0.84 | −4.27 | 2.70 |
| 200 | 689.2 | −0.94 | −4.44 | 2.83 |
| 350 | 845.9 | −0.98 | −4.46 | 2.94 |
| 500 | 1512.3 | −1.16 | −5.10 | 3.26 |

Based on the linear mixed model fitted to the data, the predicted values of population mean ΔΔQTcF and the associated two-sided 90% bootstrapped CIs are reported at plasma evobrutinib concentration values corresponding to the observed geometric mean $C_{max}$ for different evobrutinib dose groups.
*Predicted population mean ΔΔQTcF was obtained from the original dataset and not from bootstrapped data.
CI, confidence interval; $C_{max}$, maximum observed plasma concentration; ΔΔQTcF, placebo-adjusted change from baseline in QT interval corrected for heart rate by Fridericia's method.

By-Time Point Analysis

By-time point analysis showed that the maximum mean ΔΔQTcF for each of the evobrutinib dose groups ranged from −0.93 ms to 3.79 ms at all time points in the 25, 50, 75, 200, 350, and 500 mg dose groups. However, in the 100 mg dose group (n=6), the mean ΔΔQTcF was 7.1 ms at the 6 h post-dose time point (90% CI: 3.8; 10.4 ms), 5.6 ms at the 8 h post-dose time point (90% CI: −0.2; 11.4 ms) and 7.2 ms at the 12 h post-dose time point (90% CI: 2.6; 11.7 ms).

Categorical Outlier Analysis

Categorical analysis of ECG parameters revealed no clinically significant change from baseline in HR, PR and QRS values post-dose.

The absolute QTcF value did not exceed 450 ms in any of the dose groups at any of the time points. There were no ECGs where the change from baseline in QTcF exceeded 60 ms. Change from baseline in QTcF between 30 ms and 60 ms was observed in 2 (2.5%) of 81 subjects (both were in the 200 mg dose group), but the absolute QTcF value was <450 ms for both subjects. The number of ECGs with outlier values was extremely small and not clinically significant.

Treatment-emergent T wave morphological abnormalities were reported in two evobrutinib-treated subjects, one in the 50 mg dose group and one in the 100 mg dose group. These abnormalities were not observed in either patient in ECGs acquired at previous and subsequent time points.

Analysis of Results

This phase I study investigated the safety/tolerability and PK of evobrutinib and showed that single doses up to 500 mg of evobrutinib and multiple doses up to 200 mg of evobrutinib for 14 days were safe and well tolerated. The PK profile of evobrutinib showed dose-proportional and time-independent exposure without accumulation after multiple dosing when administered once daily. No clinically relevant exposure-effect relationship was detected between evobrutinib concentration and QTcF; single evobrutinib doses up to 500 mg with a peak concentration of up to 1,512 ng/mL did not prolong QTcF.

TEAEs occurred in 25% of subjects after single dosing and 48.1% after multiple dosing. The most common TEAEs after single dosing were headache and contact dermatitis, with headache, skin irritation (at locations of ECG stickers), fatigue, and upper respiratory tract infection most common after multiple dosing; the majority of events were of mild severity. With higher doses of evobrutinib, there was no apparent increase in frequency or type of adverse events. During Part 1, one subject in the 200 mg treatment group experienced a dose-limiting event (DLE) of Grade 4 increased lipase in combination with Grade 3 increased amylase. While both events were considered related to treatment, they appeared to be isolated laboratory changes that resolved quickly with no accompanying clinical signs and symptoms or evidence of abnormality of the pancreas on ultrasound examination. Furthermore, the interval between the emergence of the first abnormal values on Day 8 and the single dose itself casts doubt on any causal relationship, given the observed PK of evobrutinib. There were no other clinically relevant ECG changes or relevant cardiac or cardiovascular adverse events.

The PK profile of evobrutinib in humans demonstrated rapid absorption with peak concentrations reached within ~0.5 h, moderate-to-high plasma clearance, medium $V_z/f$, and short $t_{1/2}$. PK were dose-proportional over a 25-500 mg single-dose range and a 25-200 mg once daily multiple-dose range at steady state, with no accumulation and no time dependency observed after 14 days repeated daily dosing.

No evidence of a significant exposure-effect relationship between evobrutinib concentration and QTcF was found. Over the range of doses evaluated, mean ΔΔQTcF was <5 ms and the upper limit of the 90% two-sided CI was well below the 10 ms threshold of regulatory concern specified in the ICH-E14 guidance at all time points, with the exception of the 100 mg dose group. In this group, mean ΔΔQTcF ranged from 5.6 to 7.2 ms and the upper limit of the CI ranged from 10.4 ms to 11.7 ms at three time points. These findings are likely to be a chance occurrence given the results observed in higher-dose groups. Indeed, the results are in line with those seen with other BTK inhibitors. Neither ibrutinib nor acalabrutinib have been associated with clinically relevant prolongation of the QTc interval at therapeutic or supratherapeutic doses during randomized, double-blind, placebo- and positive-controlled thorough QT studies (see, e.g., IMBRUVICA® (ibrutinib) capsules, for oral use. Highlights of prescribing information. Pharmacyclics LLC, February 2018; CALQUENCE® (acalabrutinib) capsules, for oral use. Highlights of prescribing information. AstraZeneca, November 2017; and De Jong J., et al. in *Cancer. Chemother. Pharmacol.* 80, 1227-1237 (2017).

Evaluation of the relationship between concentration and QT/QTc using data collected in early phase clinical studies is a validated and FDA-accepted alternative strategy to conducting a thorough QT study and has been widely used to reliably exclude relevant QTc effects during drug development, supporting waiver of the regulatory requirement for a thorough QT study in some cases. While the concentration-QT analysis is limited by the small number of subjects in each dose group, pooling of data from Parts 1 and 2 and the broad range of plasma concentrations obtained across dosage groups increase the reliability of the results. High-resolution monitoring of ECGs over 24 hours permitted extraction of ECG snapshots at stable heart rates and recording of ECGs in triplicate and their central analysis further reduced any potential measurement error, helping to minimize within-subject variability, and ultimately providing more robust statistical analyses.

The central role of BTK in both FcR and BCR signaling makes BTK inhibition a promising approach for treatment of autoantibody-mediated diseases. The findings in healthy subjects reported herein indicate that evobrutinib is a promising new BTK inhibitor. Evobrutinib was well tolerated when administered as single (25-500 mg) or multiple (25-200 mg) ascending doses. PK were dose-proportional after single and multiple dosing, with no time dependency or accumulation noted after 14 days' repeated once-daily administration. Concentration-response modeling of QTc data revealed no prolongation of QTcF resulting from single doses of evobrutinib up to 500 mg.

Example 2: Phase II, Randomized, Double-Blind, Placebo-Controlled Study of Treatment of Relapsing Multiple Sclerosis in Human Patients Using Evobrutinib This study was designed to examine the effects of evobrutinib in human patients suffering from relapsing multiple sclerosis (RMS) in a phase II clinical study. The study was conducted as a randomized, double-blind, placebo-controlled study in subjects with RMS, with a parallel, open-label active control group (Tecfidera) involving 5 treatment groups with 3 doses of evobrutinib, placebo, and active control (Tecfidera). The assessing Investigator and central MRI reader were treatment blinded.

Trial Design

Figure 5:
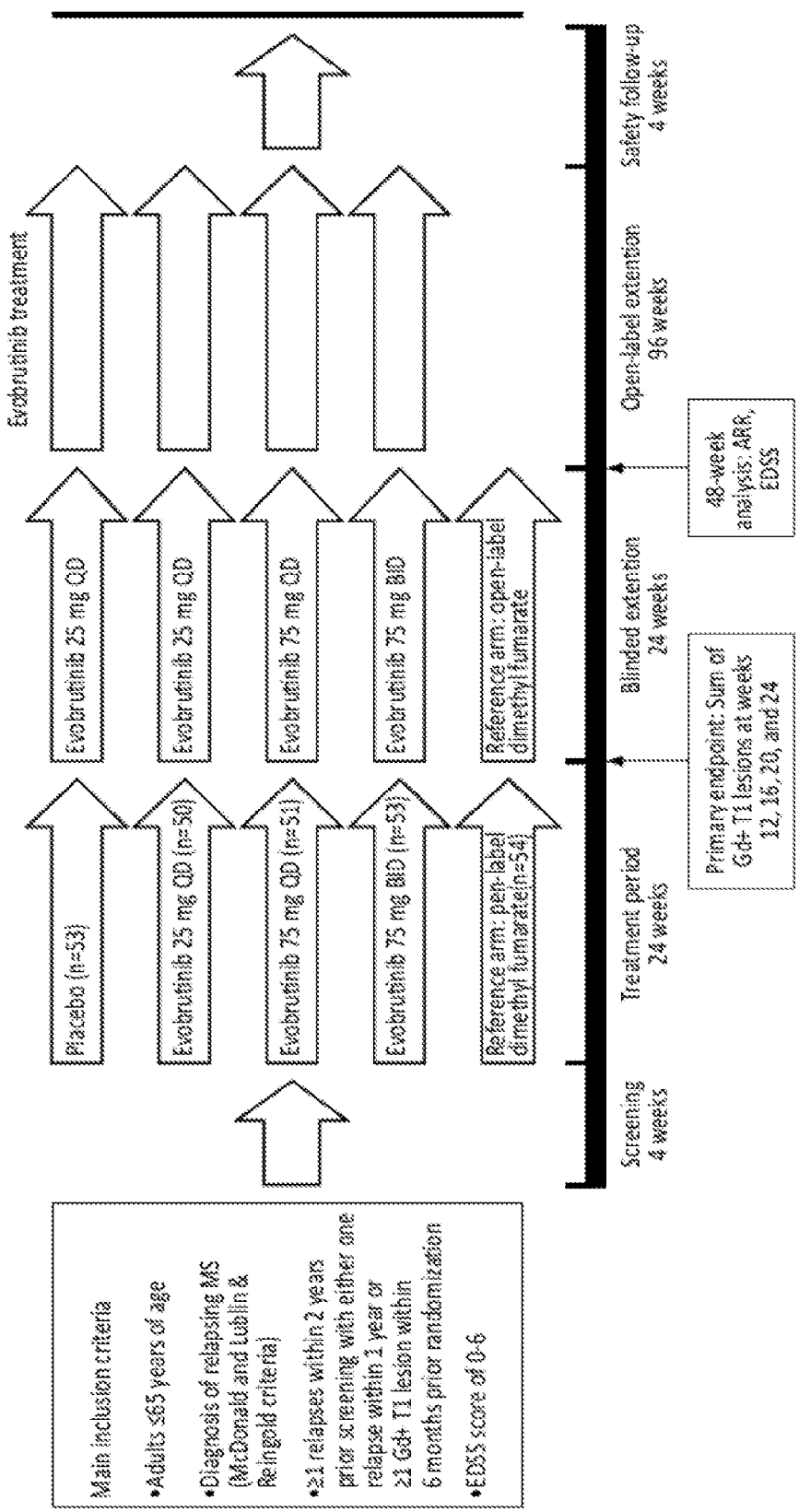
FIG. 5 depicts a flow chart of the design for examining evobrutinib in human patients suffering from relapsing multiple sclerosis (RMS) in a phase II clinical study, as further described in Example 2.

The study consisted of 4 major periods: (i) a Screening period of 4 weeks, (ii) active treatment with 3 dose groups of evobrutinib, active control (Tecfidera), or placebo for 24 weeks, (iii) a 24-week extension on active treatment with evobrutinib or active control (Tecfidera) for 24 weeks, where subjects on placebo were switched to evobrutinib, and (iv) an optional OLE Period. At the end of the 48-week main study, subjects were in 1 of 4 treatment groups (evobrutinib 25 mg daily, 75 mg once daily, or 75 mg twice daily or Tecfidera). The study protocol specified that (i) all subjects who choose to enter the OLE were to be switched to active treatment with evobrutinib at a dose of 75 mg once daily or to the eventual Phase III dose when decided, (ii) subjects transitioning from Tecfidera were to complete a washout period of at least 4 weeks prior to initiating evobrutinib treatment in the OLE Period, (iii) following completion or early termination of treatment, subjects were to return after 4 weeks for safety evaluation, and (iv) placebo subjects were to be switched to the 25 mg evobrutinib once daily dose after Week 24. The study design is shown in FIG. 5. Patients switching from the reference arm (dimethyl fumarate) to evobrutinib at week 48 were to undergo a 4-8 week washout.

Approximately 50 subjects were enrolled in each treatment group to obtain 44 evaluable subjects per group (total=approximately 250), assuming a 12% drop-out rate per year, and to compile an adequate safety database. Approximately 200 subjects were enrolled in the OLE.

Patient Selection Criteria

Only subjects meeting all inclusion criteria and no exclusion criteria were enrolled into the trial as subjects. Prior to performing any trial assessments not part of the subject's routine medical care, the Investigator ensured that the subject or the subject's legal representative has provided written informed consent.

Subjects who did not meet the inclusion/exclusion criteria within the first Screening period and were considered screen failures and could undergo rescreening once after approval by the Medical Monitor. The second Screening period was a new 28-day Screening period, and the subject would receive a new identification number. All other testing was required to be redone at rescreening.

Inclusion Criteria

1. Subjects with a diagnosis of relapsing multiple sclerosis (may include subjects with Secondary PMS [SPMS] with superimposed relapses provided they meet the other criteria) in accordance with revised McDonald criteria for MS and Lublin and Reingold.
2. Male or female aged 18 to 65 years.
3. One or more documented relapses within the 2 years before Screening with either:
   a) One relapse which occurred within the last year prior to randomization or b) the presence of at least 1 Gd+ T1 lesion within 6 months prior to randomization would make the patient eligible.
4. Expanded Disability Status Scale score of 0 to 6 at Baseline.
5. Women of childbearing potential must use a supplementary barrier method together with a highly effective method of contraception (according to ICH guidance M3[R2]) for 4 weeks prior to randomization, throughout the trial, and for 90 days after the last dose of IMP. For the purposes of this trial:
   Women were considered of childbearing potential unless they are postmenopausal. Females who are postmenopausal (age-related amenorrhea ≥12 consecutive months and increased follicle-stimulating hormone [FSH]>40 mIU/mL) or who have undergone hysterectomy or bilateral oophorectomy were exempt from pregnancy testing. If necessary to confirm postmenopausal status, an FSH was drawn at Screening.
   Highly effective contraception includes:
     Combined (estrogen and progestogen containing) hormonal contraception associated with inhibition of ovulation; oral, intravaginal or transdermal
     Progestogen-only hormonal contraception associated with inhibition of ovulation; oral, injectable or implantable
     Intrauterine device (IUD)
     Intrauterine hormone-releasing system (IUS)
     Bilateral tubal occlusion
     Vasectomized partner
     Sexual abstinence
   Supplementary barrier methods include:
     Male or female condom with or without spermicide
     Cap, diaphragm or sponge with spermicide
   Men agreed to use and have their female partners use a supplementary barrier method together with a highly effective contraceptive method as defined above for at least 90 days after the last IMP administration.
   Women of childbearing potential had a negative serum pregnancy test at the Screening Visit and a negative urine pregnancy test at randomization on Day 1 before dosing.
6. Signed and dated informed consent (subject was able to understand the informed consent) indicating that the subject has been informed of all the pertinent aspects of the trial prior to enrollment and would comply with the requirements of the protocol.

Exclusion Criteria

1. Progressive MS either Primary or Secondary if Secondary is without evidence of relapse.
2. Disease duration >15 years (subject reported adequate in absence of written medical record) in subjects with EDSS of 2 or less.
3. Treatment with rituximab, ocrelizumab, mitoxantrone, or lymphocyte-depleting therapies (e.g., alemtuzumab, anti-CD4, cladribine, cyclophosphamide, total body irradiation, bone marrow transplantation) not used within 48 weeks prior to randomization.

4. Use of lymphocyte trafficking blockers (eg, natalizumab, fingolimod) within 24 weeks prior to randomization.
5. Use of intravenous (IV) immunoglobulins (Ig), plasmapheresis, and immunosuppressive treatments within 4 weeks prior to randomization.
6. Treatment with B-interferons or glatiramer acetate within 4 weeks prior to randomization.
7. Systemic glucocorticoids within 4 weeks prior to randomization.
8. Treatment with teriflunomide within 12 weeks prior to randomization.
9. Treatment with daclizumab within 12 weeks prior to randomization.
10. Exposure to Tecfidera within 6 months prior to randomization.
11. Any allergy, contraindication, or inability to tolerate Tecfidera.
12. Treatment with dalfampridine (fampridine, Ampyra) unless on a stable dose for ≥30 days prior to randomization.
13. Inability to comply with MRI scanning, including contra-indications to MRI such as known allergy to gadolinium contrast media, claustrophobia, presence of a pacemaker, cochlear implants, ferromagnetic devices or clips, intracranial vascular clips, insulin pumps, nerve stimulators.
14. Immunologic disorder other than MS, with the exception of secondary well-controlled diabetes or thyroid disorder, or any other condition requiring oral, IV, intramuscular, or intra-articular corticosteroid therapy.
15. Vaccination with live or live-attenuated virus vaccine within 1 month prior to Screening.
16. Severe drug allergy or history of anaphylaxis, or allergy to the IMP or any of its excipients.
17. Active, clinically significant viral, bacterial, or fungal infection, or any major episode of infection requiring hospitalization or treatment with parenteral anti-infectives within 4 weeks of Screening, or completion of oral anti-infectives within 2 weeks before or during Screening, or a history of recurrent infections (i.e., 3 or more of the same type of infection in a 12-month rolling period). Vaginal candidiasis, onychomycosis, and genital or oral herpes simplex virus considered by the Investigator to be sufficiently controlled would not be exclusionary.
18. History of or positive testing for human immunodeficiency virus (HIV), hepatitis C (HCV) antibody and/or polymerase chain reaction, hepatitis B surface antigen (HBsAg) (+) and/or hepatitis B core total, and/or IgM antibody (+) at Screening. Testing for HIV will only be conducted where required as per local regulation.
19. The subject:
    Had a history of or current diagnosis of active tuberculosis (TB) or
    Was currently undergoing treatment for latent TB infection (LTBI) or
    Had an untreated LTBI as determined by documented results within 3 months of the Screening visit of a positive TB skin test with purified protein derivative with induration ≥5 mm or
    Had a positive QuantiFERON®-TB test at Screening.
    Subjects with documented completed appropriate LTBI treatment were not excluded and were not required to be tested.
20. Indeterminate QuantiFERON-TB tests could be repeated once, and were considered positive if retest results were positive or indeterminate.
21. Subjects with current household contacts with active TB were excluded.
22. History of splenectomy at any time, or any major surgery within 2 months prior to Screening.
23. History of myocardial infarction or cerebrovascular event within 6 months prior to Screening, or current active angina pectoris, symptomatic heart failure, uncontrolled seizures, untreated hypertension, GI bleeding, or any other significant active medical condition in the Investigator's opinion.
24. A history of attempted suicide within 6 months prior to Screening or a positive response to items 4 or 5 of Columbia-Suicide Severity Rating Scale (C-SSRS).
25. An episode of major depression within the last 6 months prior to Screening (clinically stable minor depression is not exclusionary).
26. On anticoagulation, fish oil supplements, or antiplatelet therapy other than daily aspirin for cardioprotection and treatment of Tecfidera induced flushing.
27. History of cancer, except adequately treated basal cell or squamous cell carcinoma of the skin (no more than 3 lesions requiring treatment in lifetime) or carcinoma in situ/cervical intraepithelial neoplasia of the uterine cervix, unless considered cured ≥5 years.
28. Breastfeeding/lactating or pregnant women.
29. Participation in any investigational drug trial within 1 month or 5 half-lives of the investigational drug, whichever is longest, prior to Screening.
30. Subjects that were currently receiving (or unable to stop using prior to receiving the first dose of investigational medicinal product (IMP)) medications or herbal supplements known to be potent inhibitors of cytochrome P450 3A (CYP3A) (must stop at least 1 week prior), potent inducers of CYP3A (must stop at least 3 weeks prior), or drugs mainly metabolized by CYP3A with a narrow therapeutic index (must stop at least 1 day prior).
31. History of or current alcohol or substance abuse
    Excessive alcohol use was defined as alcohol and/or substance abuse or dependence (as defined by the Diagnostic and Statistical Manual of Mental Disorders, $5^{th}$ edition) in the past year or a history of alcohol or substance abuse, as determined by the Investigator.
32. Clinically significant abnormality on electrocardiogram (ECG), or an active infective process or any other clinically significant abnormality on Screening chest X-ray (CXR) taken within 4 weeks of the first dose, per Investigator opinion. If a CXR had been taken within the previous 3 months and results are available and normal, the CXR did not need to be carried out.
33. Estimated glomerular filtration rate (eGFR) by the 4-variable Modification of Diet in Renal Disease equation of <45 mL/min/1.73 $m^2$ or any renal condition that would preclude the administration of gadolinium (eg, acute renal insufficiency).
34. Alanine aminotransferase (ALT), aspartate aminotransferase (AST), amylase, or lipase >2× above upper limit of normal (ULN) of laboratory reference range, total bilirubin >1.5×ULN, any other clinically significant laboratory abnormality.
35. B cell (CD19) count <50% of the lower limit of normal at Screening 36. Significant cytopenia, including neutrophil count <1,500/mm$^3$, platelet count <75,000/mm$^3$, absolute lymphocyte count <800/mm$^3$, or a white blood cell count <3500/mm$^3$.

For subjects participating in the OLE Period after receiving Tecfidera during the 48-week main study, absolute lymphocyte count <800/mm$^3$ was considered an exclusion criterion.

Drug Substance, Dose and Administration

The drug substance evobrutinib, chemical name 1-(4-{[6-amino-5-(4-phenoxy-phenyl)-pyrimidin-4-ylamino]-methyl}-piperidin-1-yl)-propenone, is a white to yellow powder. Evobrutinib was administered as white tablets ready for oral administration containing 25 mg of drug substance formulated with excipients. The placebo was administered as white tablets ready for oral administration matching the active both in color and in size.

The active control group received Tecfidera. For the first 7 days, Tecfidera was given 120 mg twice daily orally. Following this, and for the duration of treatment, it was given 240 mg twice daily orally. For sites in the European Union (EU), Tecfidera was centrally sourced and provided by the Sponsor. For sites in the USA, Tecfidera was locally sourced at each trial site according to local regulations. Tecfidera was to be administered according to the local label and applicable regulations.

The protocol specified that subjects received 25 mg once daily, 75 mg once daily, or 75 mg twice daily evobrutinib or placebo administered as tablets for 168 days. To maintain blinding for placebo and evobrutinib, subjects self-administered study medication at a schedule similar to the 75 mg evobrutinib twice daily dosing schedule (i.e., 3 tablets twice daily). At the end of the 24-week treatment period, the placebo group was to be switched to evobrutinib at a dose of 25 mg once daily; however, flexibility was maintained to allow adjusting this dose based on data from the primary analysis.

The protocol specified that subjects who choose to participate in the OLE Period received open-label evobrutinib 75 mg once daily or the eventual Phase III dose when decided. Subjects who do not participate in the OLE Period were to no longer receive evobrutinib or Tecfidera.

The protocol specified that subjects self-administered the IMP at a set time each day (every 12 hours ±2 hours). Subjects were to take their daily dose more than 1 hour prior to a meal or snack and more than 2 hours after a meal or snack. Clear fluids were allowed at any time. On trial visit days, the IMP was to be administered during the trial visit after the scheduled trial visit procedures (other than post-treatment PK/PD sampling) are completed.

The protocol specified that if a dose was missed, the subject could take the missed dose up to 6 hours after the scheduled time. If more than 6 hours elapsed since the dose was missed, the subject was to skip the dose for that period, make note of the missed dose, and take the next dose at the regularly scheduled time.

The protocol specified that when PK visits were scheduled to occur, the subject was to refrain from taking their scheduled morning dose and take their dose of IMP when instructed at the visit. Subjects were asked to record the date and time of dosing and food intake around dosing in a subject diary. Subjects who developed GI or flushing disturbances while receiving Tecfidera could reduce their study treatment dose by taking 120 mg twice daily for 1 month at the Investigator's discretion. After 1 month at the reduced dose, subjects resumed the 240 mg twice daily dosing. If the subject was still unable to tolerate the study treatment, the subject was to permanently discontinue study treatment.

Assignment to Treatment Groups

Eligible subjects were randomized 1:1:1:1:1 to treatment with placebo, low-dose evobrutinib (25 mg once daily), mid-dose evobrutinib (75 mg once daily), high-dose evobrutinib (75 mg twice daily), or Tecfidera (administered twice daily at a final dose of 240 mg), through a central randomization process by an IWRS prior to dosing on Day 1. Stratification occurred by region (USA or Western Europe, Eastern Europe and BTKO capable, Eastern Europe and not BTKO capable, and RoW). For the first 7 days, Tecfidera was administered orally at 120 mg twice daily. Following this and for the duration of treatment, Tecfidera was administered orally at 240 mg twice daily. All subjects who choose to enter the OLE Period were to receive open-label evobrutinib 75 mg once daily or the eventual Phase III dose.

Efficacy Assessment

Efficacy assessments were undertaken. During treatment, i.e., Day 1 to Week 48 (or Week 96 for the OLE Period), all assessments were to be completed prior to the administration of study medication.

Brain Magnetic Resonance Imaging Scans

The protocol specified that MRI scans were to be performed at Screening, at 4-week intervals from Week 12 to 24, and at the End of Treatment Visit at Week 48 (including for subjects receiving Tecfidera who choose to enter the OLE Period). For subjects in the OLE Period, an MRI was also performed at Day 1 (except for subjects who received Tecfidera during the 48-week parent study and had an MRI at the End of Treatment Visit at Week 48), Week 48, and the OLE End of Treatment Visit at Week 96. If a subject discontinued the study more than 4 weeks after his or her most recent MRI, the protocol specified that an MRI may be obtained at the 4-week Safety Follow-up Visit. The Screening MRI scan was to be acquired before randomization and dosing to allow for the readouts to be read by the central MRI reader (approximately 7 days).

Gadolinium was used to enhance T1-weighted lesions and to optimize clarity and accuracy of reporting. As gadolinium is excreted renally, subjects with acute renal insufficiency (eGFR <45 mL/min/1.73 m$^2$) will be excluded from the trial.

The protocol specified that brain MRI scans were performed according to a standardized imaging protocol before and after the administration of single-dose gadolinium. Images were assessed and reported by an independent, blinded, centralized MRI reading service, provided by NeuroRx Research. The assessment was performed in the absence of clinical information. Further details, including the scans required and the optimal MRI workflow, were provided in a separate Imaging Manual provided to each trial site by NeuroRx Research. All MRI images were reviewed and reported locally by a radiologist for safety. The local report was to contain only non-MS pathology and was to be provided to the Treating Investigator.

The protocol specified that, where possible, the use of high dose corticosteroids should be avoided in the 3-week period prior to a scheduled MRI scan. In subjects receiving corticosteroids for an MS relapse, there was a 3-week interval between the last dose of corticosteroids and the scheduled MRI scan.

In addition, if a scheduled MRI scan was delayed or an unscheduled MRI scan was indicated, care was taken to avoid the subject being exposed to gadolinium more than once in a 4-week period, i.e., the protocol specified it may be necessary to cancel the MRI scan at the next scheduled visit (all other assessments should be completed at the visit as normal). If the next scheduled visit was the End of Treatment Visit (Week 48), the Week 48 MRI scan was performed as soon as the 4-week period since previous exposure to gadolinium has elapsed.

Expanded Disability Status Scale

The protocol specified that a standard neurological examination was to be performed by an Assessing Neurologist and the subject's level of disability was to be assessed using the EDSS. The EDSS is an ordinal clinical rating scale ranging from 0 (normal neurological examination) to 10 (death due to MS) in half-point increments and should be administered in person by a neurologist trained in its use. The EDSS score was calculated after neurologic testing and examination of the following eight functional systems, areas of the central nervous system that control bodily functions:

Pyramidal (ability to walk)
Cerebellar (coordination)
Brain stem (speech and swallowing)
Sensory (touch and pain)
Bowel and bladder functions
Visual
Mental
Other (includes any other neurological findings due to MS).

Steps were taken to eliminate inter- and intra-rater variability in the administration and assessment of the EDSS in the trial. The protocol specified that EDSS was to be administered by an Assessing Neurologist who has undergone trial-specific EDSS training prior to the start of the trial and the same individual evaluated a given subject throughout the course of the trial. The EDSS assessment was to take place at approximately the same time of day and a standardized protocol was to be followed for the neurologic examination.

Relapse Assessment

Subjects were assessed for MS relapse at visits beginning at Week 4. Relapse was also assessed at any Unscheduled Visit for Neurological Worsening and Relapse Assessment. For subjects in the OLE Period, MS relapse was assessed at all visits. A qualifying relapse was defined as new, worsening or recurrent neurological symptoms attributed to MS that last for at least 24 hours without fever or infection, or adverse reaction to prescribed medication, preceded by a stable or improving neurological status of at least 30 days. The relapse must have been accompanied by new clinical signs (i.e., changes in the neurological examination or an increase in EDSS score).

The protocol specified that all cases of potential relapse were to be objectively confirmed by the Investigator regardless of whether they were identified during a scheduled or unscheduled visit. Any assessments needed to confirm the relapse were to be performed, and details of the relapse were to be documented within the relevant section(s) of the eCRF. The criteria for a protocol-defined relapse was to be clear and there was to be documentation of how each potential relapse did or did not meet the criteria. Subjects who had a documented relapse during treatment were not required to discontinue treatment unless they meet any of the criteria for withdrawal from the trial therapy or withdrawal from the trial, including the need for treatment with a non-permitted medication.

A non-qualifying relapse was any other relapse as defined by the Investigator that does not meet the qualifying relapse definition.

Safety Assessment

Safety profile of the IMP was assessed through the recording, reporting and analysis of baseline medical conditions; AEs; physical examination findings including vital signs, ECGs, and laboratory tests (including Ig and subclass concentration and B, NK, and T cell counts). Comprehensive assessment of any apparent toxicity experienced by each subject was performed from the time of giving informed consent and throughout the trial. The Investigator was to report any AEs, whether observed by the Investigator or reported by the subject.

Adverse Events

Adverse Event Definitions

Adverse Event: An AE was any untoward medical occurrence in a subject or clinical investigation subject administered a pharmaceutical product, regardless of causal relationship with this treatment. An AE could therefore be any unfavorable and unintended sign (including an abnormal laboratory finding), symptom, or disease temporally associated with the use of a medicinal product, whether or not considered related to the medicinal product.

For surgical or diagnostic procedures, the condition/illness leading to such a procedure was considered as the AE rather than the procedure itself.

The Investigator was required to grade the severity or toxicity of each AE. Investigators referenced the National Cancer Institute-Common Terminology Criteria for AEs (NCI-CTCAE), Version 4.03 (publication date: 14 Jun. 2010) a descriptive terminology provided in the Manual of Procedures that can be used for AE reporting.

A general grading (severity/intensity; hereafter referred to as severity) scale was provided at the beginning of the above referenced document, and specific event grades were also provided. Only if a particular AE's severity was not specifically graded by the guidance document, then the Investigator was to use the general NCI-CTCAE definitions of Grade 1 through Grade 5 following his or her best medical judgment. The 5 general grades are:

Grade 1 or Mild
Grade 2 or Moderate
Grade 3 or Severe
Grade 4 or Life-threatening
Grade 5 or Death.

According to Sponsor convention, any clinical AE with severity of Grade 4 or Grade 5 was to be reported as an SAE. However, a laboratory abnormality of Grade 4, such as anemia or neutropenia, was considered serious only if the condition meets 1 of the serious criteria described below.

The protocol specified that if death occurs, the primary cause of death or event leading to death was to be recorded and reported as an SAE. "Fatal" was recorded as the outcome of this specific event and death was not recorded as a separate event. Only, if no cause of death could be reported (eg, sudden death, unexplained death), then the death per se might be reported as an SAE.

Investigators were to systematically assess the causal relationship of AEs to IMP using the following definitions. Decisive factors for the assessment of causal relationship of an AE to the IMP include, but may not be limited to, temporal relationship between the AE and the IMP, known side effects of IMP, medical history, concomitant medication, course of the underlying disease, trial procedures.

Unrelated: Not reasonably related to the IMP. AE could not medically (pharmacologically/clinically) be attributed to the IMP under study in this clinical trial protocol. A reasonable alternative explanation must be available.

Related: Reasonably related to the IMP. AE could medically (pharmacologically/clinically) be attributed to the IMP under study in this clinical trial protocol.

Abnormal Laboratory Findings and Other Abnormal Investigational Findings: The protocol specified that abnormal laboratory findings and other abnormal investigational findings (eg, on an ECG trace) should not be reported as AEs unless they are associated with clinical signs and symptoms, lead to treatment discontinuation or are considered otherwise medically important by the Investigator. If a laboratory abnormality fulfilled these criteria, the identified medical condition (eg, anemia, increased ALT) was to be reported as the AE rather than the abnormal value itself.

Serious Adverse Events: An SAE is any untoward medical occurrence that at any dose:
  Results in death.
  Is life-threatening. (Note: The term "life-threatening" refers to an event in which the subject is at risk of death at the time of the event, not an event that hypothetically might have caused death if it was more severe)
  Requires inpatient hospitalization or prolongs an existing hospitalization, except in the case of hospitalizations due to protocol-defined relapses.
  Results in persistent or significant disability or incapacity.
  Is a congenital anomaly or birth defect.
  Is otherwise considered to be medically important. (Note: Important medical events that may not result in death, be life-threatening, or require hospitalization may be considered as SAEs when, based upon appropriate medical judgment, they may jeopardize the subject or may require medical or surgical intervention to prevent one of the outcomes listed above. Examples of such events include allergic bronchospasm requiring intensive treatment in an emergency room or at home, blood dyscrasias or convulsions that do not result in inpatient hospitalization, or the development of drug dependency or drug abuse.)

For the purposes of reporting, any suspected transmission of an infectious agent via an IMP was also considered an SAE.

Events that do not Meet the Definition of an SAE

Elective hospitalizations to administer, or to simplify trial treatment or trial procedures (eg, an overnight stay to facilitate intravenous therapy) were not considered SAEs. However, all events leading to unplanned hospitalizations or unplanned prolongation of an elective hospitalization (eg, undesirable effects of any administered treatment) were to be documented and reported as SAEs, except for unplanned hospitalizations due to relapse of MS.

Events not to be Considered as AEs/SAEs

Medical conditions present at the initial trial visit that did not worsen in severity or frequency during the trial were defined as Baseline medical conditions and were not to be considered AEs.

Worsening of the underlying disease was not routinely to be considered an AE or SAE, but was rather an efficacy endpoint, unless deemed to be causally related to the IMP. However, if significant adverse signs or symptoms occurred in association with complications or a prolonging of a hospitalization originally due to relapse or disease progression, then these specific complications or hospital prolongation events were to be recorded as AEs.

Methods of Recording and Assessing Adverse Events

The protocol specified that, at each trial visit, the subject was queried on changes in his or her condition. During the reporting period, any unfavorable changes in the subject's condition were to be recorded as AEs, whether reported by the subject or observed by the Investigator.

Complete, accurate and consistent data on all AEs experienced for the duration of the reporting period (defined below) were to be reported on an ongoing basis in the appropriate section of the eCRF. All SAEs were to be additionally documented and reported using the appropriate Report Form.

The protocol specified that it is important that each AE report include a description of the event, its duration (onset and resolution dates and times when it is important to assess the time of AE onset relative to the recorded treatment administration time), its severity, its causal relationship with the trial treatment, any other potential causal factors, any treatment given or other action taken, including dose modification or discontinuation of the IMP, and its outcome. In addition, serious cases were to be identified and the appropriate seriousness criteria documented.

Definition of the Adverse Event Reporting Period

The protocol specified that the AE reporting period for safety surveillance begins when the subject was initially included in the trial (date of first signature of informed consent/date of first signature of first informed consent) and continued until the 4-week Safety Follow-up/End of Trial Visit. Any SAE assessed as related to IMP was to be reported whenever it occurs, irrespective of the time elapsed since the last administration of IMP.

Procedure for Reporting Serious Adverse Events

The protocol specified that in the event of any new SAE occurring during the reporting period, the Investigator must immediately (within a maximum of 24 hours after becoming aware of the event) inform the Sponsor or its designee using the SAE Report Form, which must be completed by the Investigator following specific completion instructions.

For names, addresses, telephone and fax numbers for SAE reporting, this was handled according to information in the Adverse Event Safety Report Form. In exceptional circumstances, the protocol specified that an SAE (or follow-up information) could be reported by telephone; in these cases, the eCRF must be completed.

Relevant pages from the eCRF were permitted to be provided in parallel (e.g., medical history, concomitant drugs). Additional documents could be provided by the Investigator, if available (e.g., laboratory results, hospital report, autopsy report). In all cases, the information provided on the SAE Report Form was to be consistent with the data about the event recorded in the eCRF.

The Investigator was required to respond to any request for follow-up information (e.g., additional information, outcome, final evaluation, other records where needed) or to any question the Sponsor/designee had on the AE within the same timelines as those noted above for initial reports. This was necessary to ensure prompt assessment of the event by the Sponsor or designee and (as applicable) to allow the Sponsor to meet strict regulatory timelines associated with expedited safety reporting obligations.

Requests for follow-up were to be made via the responsible Medical Monitor, although in exceptional circumstances the Global Drug Safety department was permitted to contact the Investigator directly to obtain further information or to discuss the event.

EndPoints

Primary Endpoints

The primary endpoint was the total number of gadolinium-enhancing T1 lesions at Week 12, 16, 20, and 24. The primary analysis was a comparison of each evobrutinib dose arm versus placebo based on this endpoint, with a supportive test for dose-response. Secondary Endpoints Key secondary endpoints to evaluate the efficacy and safety of evobrutinib compared to placebo were:
  Annualized relapse rate (ARR), based on protocol-defined qualified relapses, at Week 24
  Qualified relapse-free status at Week 24
  Change from Baseline in EDSS at Week 24
  Safety as assessed by the nature, severity, and occurrence of AEs; vital signs; ECGs; absolute concentrations and change from Baseline in Ig levels; absolute numbers and change from Baseline in B cells; and clinical laboratory safety parameters (duration of placebo treatment group limited to 24 weeks).

Additional Secondary Endpoints

To evaluate the efficacy of evobrutinib compared to placebo, the following were evaluated:
  Total number of new Gd+ T1 lesions at Week 12, 16, 20, and 24
  Mean per-scan number of Gd+ T1 lesions at Week 12, 16, 20, and 24
  Total number of new or enlarging T2 lesions at Week 12, 16, 20, and 24
  Change from Baseline in the volume of Gd+ T1 lesions at Week 24
  Change from Baseline in the volume of T2 lesions at Week 24.

To evaluate efficacy within evobrutinib dose groups, the following were evaluated:
  Number of Gd+ T1 lesions at Week 48
  Number of new Gd+ T1 lesions at Week 48
  Annualized relapse rate, based on protocol-defined qualified relapses, at Week 48
  Qualified relapse-free status at Week 48
  Change from Baseline in EDSS at Week 48
  Number of new or enlarging T2 lesions at Week 48
  Change from Baseline in the volume of Gd+ T1 lesions at Week 48
  Change from Baseline in the volume of T2 lesions at Week 48.

To evaluate the efficacy and safety of Tecfidera, the following were evaluated:
  Total number of gadolinium-enhancing T1 lesions at Week 12, 16, 20, and 24
  Annualized relapse rate, based on protocol-defined qualified relapses, at Week 24
  Qualified relapse-free status at Week 24
  Change from Baseline in EDSS at Week 24
  Safety as assessed by the nature, severity, and occurrence of AEs; vital signs; ECGs; absolute concentrations and change from Baseline in Ig levels; absolute numbers and change from Baseline in B cells; and clinical laboratory safety parameters
  Total number of new Gd+ T1 lesions at Week 12, 16, 20, and 24
  Mean per-scan number of Gd+ T1 lesions at Week 12, 16, 20, and 24
  Total number of new or enlarging T2 lesions at Week 12, 16, 20, and 24
  Change from Baseline in the volume of Gd+ T1 lesions at Week 24
  Change from Baseline in the volume of T2 lesions at Week 24
  Number of Gd+ T1 lesions at Week 48
  Number of new Gd+ T1 lesions at Week 48
  Annualized relapse rate, based on protocol-defined qualified relapses, by Week 48
  Qualified relapse-free status at Week 48
  Change from Baseline in EDSS at Week 48
  Number of new or enlarging T2 lesions at Week 48
  Change from Baseline in the volume of Gd+ T1 lesions at Week 48
  Change from Baseline in the volume of T2 lesions at Week 48.

Exploratory Endpoints

Exploratory endpoints were:
  Absolute number and change from Baseline for B cells and B cell subsets, T cells and T cell subsets, and NK cells in peripheral blood
  Gene expression analysis in subjects treated with evobrutinib or placebo
  Absolute values and change from Baseline of soluble factors in the plasma if measured
  Pharmacokinetic/pharmacodynamic modeling and simulation of evobrutinib.
  Change in HRQoL as measured with SF-36v2 (physical component summary [PCS]/mental component summary [MCS] and sub-domains) over time (area under the curve) in all subjects
  Change in HRQoL as measured with SF-36v2 (PCS/MCS and sub-domains) from Baseline to Week 24 and from Baseline to Week 48 in all subjects
  Drug metabolizing enzyme, drug transporter genotypes, and other variants associated with safety and/or efficacy, if measured, from consenting subjects receiving evobrutinib or placebo.

Analysis of Primary Endpoint

The protocol specified that the primary analysis of total number of Gd+ T1 lesions, at Week 12, 16, 20, and 24, was to be an estimate of lesion rate ratio, together with associated 95% CI and p-value, comparing each evobrutinib dose group to placebo, based on a negative binomial (NB) model, where the offset is based on the log of number of scans, with evobrutinib dose or placebo group as a factor and adjustment for covariates based on randomization strata and baseline MRI activity. Other covariates were permitted to be considered. Protocol specified that if the model failed to converge, the primary analysis would be an estimate of the shift in location of the distribution of the Gd+ T1 lesion count via the Hodges-Lehman estimate, together with associated 95% CI and p-value based on the stratified Wilcoxon rank-sum test, comparing each evobrutinib dose group to placebo. Descriptive statistics for the total number of Gd+ T1 lesions, at Week 12, 16, 20, and 24, are provided for each treatment group.

The protocol specified that the primary analysis of the primary endpoint was to be based on the mITT analysis set, with supportive analyses based on the ITT and PP analysis sets. If the primary analysis was comprised of negative binomial modelling, the computed p-value testing the null hypothesis $H_0$: RR=1.0 for each evobrutinib dose group was reported, where RR denotes lesion rate ratio comparing a given evobrutinib dose group to placebo. If the primary analysis must be nonparametric due to model non-convergence, then the computed p-value testing the null hypothesis_$H_0$: $P(X<Y)+0.5 \times P(X=Y)=0.5$, via the stratified Wilcoxon rank-sum test, for each evobrutinib treatment group was reported, where X denotes the primary endpoint evaluated for a subject in a given evobrutinib treatment group, and Y denotes the primary endpoint evaluated for a subject in the placebo group. The FWER, i.e., overall type I error rate for the primary analysis, was controlled at the 0.05 level by testing the 3 evobrutinib hypotheses for the low, mid, and high dose groups using the Hochberg procedure. A test for a monotonic dose-response relationship, between ordered evobrutinib dose (low, mid, high) and the primary efficacy endpoint, was performed as a supportive analysis.

No formal comparisons between the Tecfidera arm and any other treatment group were performed for the primary endpoint.

Analysis of Secondary Endpoints

Analysis of secondary endpoints was based on the mITT analysis set. Descriptive statistics for MRI and clinical secondary endpoints, was provided for the evobrutinib dose arms, the placebo arm (limited to 24 week endpoints), and the Tecfidera arm. For 48 week endpoints, descriptive statistics are provided for the placebo/evobrutinib arm. Descriptive statistics for ARR were calculated for each treatment group as the total number of qualified relapses divided by the number of subject-years of observation.

The multiple-comparison procedure for testing the key secondary efficacy endpoints was provided in the IAP. Other secondary efficacy endpoints were analyzed for exploratory purposes. No formal comparisons between the Tecfidera arm and any other treatment group was performed for the secondary efficacy endpoints.

Secondary Efficacy Endpoints: Baseline to 24 Weeks

Comparison of an evobrutinib treatment group to the placebo group using ARR at Week 24 was based on the rate ratio estimated from an NB model for qualified relapse count, with offset equal to the log of years on study, with evobrutinib dose group or placebo group as a factor and adjustment for covariates based on randomization strata and pre-baseline relapse activity. The comparison of an evobrutinib treatment group to the placebo group using proportion qualified relapse-free at Week 24, was based on the odds ratio estimated from a logistic model for the odds of a subject being qualified relapse-free at Week 24, where subjects who discontinued study prior to Week 24 without having a qualified relapse were counted as not being qualified relapse-free at Week 24, with evobrutinib dose group or placebo group as a factor and adjustment for covariates based on randomization strata.

The comparison of an evobrutinib treatment group to placebo group using change from Baseline in EDSS at Week 24 was based on a stratified Wilcoxon rank-sum test, with strata defined by baseline EDSS and randomization strata and pre-baseline relapse activity. The analysis of change from Baseline in volume of Gd+ T1 lesions at Week 24, and change from Baseline in volume of T2 lesions at Week 24, was based on an analysis of covariance (ANCOVA) model of the appropriately transformed variable, with evobrutinib dose group or placebo group as a factor, randomization strata as a factor and baseline MRI activity as a covariate. The comparison of an evobrutinib treatment group to placebo using total number of new Gd+ T1 lesions, or total number of new or enlarging T2 lesions, at Week 12, 16, 20, and 24, was based on an NB model, similar to that used for the primary analysis. Estimation of mean per-scan number of Gd+ T1 lesions at Weeks 12, 16, 20, and 24, for each treatment group, was based on the NB model. In the analysis of each secondary endpoint, other covariates were permitted to be included in the model.

A test for a monotonic dose-response relationship, between ordered evobrutinib dose (low, mid, high) and each of the key secondary efficacy endpoints, was performed as supportive analyses.

Secondary Efficacy Endpoints: Baseline to 48 Weeks

Descriptive statistics for MRI and clinical endpoints, Baseline to Week 48, are provided for the evobrutinib dose arms, the placebo/evobrutinib arm, and the Tecfidera arm.

The number of Gd+ T1 lesions, number of new Gd+ T1 lesions, number of new and enlarging T2 lesions, the observed and change from Baseline values of Gd+ T1 lesion volume, and observed and change from Baseline values of T2 lesion volume, have been summarized by treatment group (placebo, 3 evobrutinib dose groups, and Tecfidera) and time point over the treatment period.

Annualized relapse rate from Baseline to Week 24, from Week 24 to Week 48, and from Baseline to Week 48 was summarized by treatment group. Qualifying relapse-free status at Week 24 and at Week 48 was summarized by treatment group. Observed and change from Baseline values of EDSS was summarized by treatment group and time point over the treatment period.

Statistical Analysis

A per-group sample size of 44 evaluable patients was estimated to provide 85% power to detect a decrease of 90% in the total number of Gd+ T1 lesions (over MRI assessments at Week 12, 16, 20, and 24) between a given evobrutinib group and placebo using the Wilcoxon rank-sum test, at a two-sided significance level of 5%, assuming a negative binomial (NB) distribution for total lesion count in each arm. Assumptions on mean lesion count over four scans (5.5 for the placebo arm) and the NB shape parameters were based on results from recent phase 2 studies of MS. Assuming a 12% drop-out rate over one year, the target enrolment per arm was 50 patients.

Primary and secondary efficacy endpoints were analysed based on the modified intention-to-treat (mITT) analysis set, consisting of all randomized patients with at least one available baseline and one post-baseline MRI assessment. Each evobrutinib dose group was compared to placebo based on Gd+ T1 lesion rate ratio (primary endpoint) or qualified relapse rate ratio (key secondary endpoint), as estimated from an NB model for lesion count over Weeks 12-24 (offset log number of scans), or qualified relapse count during the first 24 weeks (offset log of years on study). For each endpoint, rate ratio (RR; null-hypothesis RR=1.0) adjusted for baseline disease activity was reported together with associated 95% CI and p-value. The T2 lesion endpoint was analysed similarly. Dose-response relationships between evobrutinib treatment dose and primary and key secondary endpoints were assessed for linear and monotonic trend. The analysis of CFB in cube root of volume of T2 lesions at Week 24 was based on a mixed-effect model for repeated measures, with fixed effects for treatment, week of visit, and treatment-by-week interaction, random effect for subject, and adjustment for baseline cube root of lesion volume. CFB in SF-36 score at Week 24 was analysed similarly. Descriptive statistics were used to further describe the study outcomes.

Results

Patients

A total of 267 patients were randomised to treatment and 261 were included in the mITT population (6 patients were excluded from analysis due to a lack of post-baseline MRI assessments). Overall, 243 (91%) patients completed 24 weeks of treatment. Baseline characteristics were balanced across groups, as shown in Table 6, all patients were white (100%), most were female (69%) and had RMS (87%), and the mean (standard deviation [SD]) age was 42 (±10.7) years. Median time since MS onset was 8.5 years across treatments.

TABLE 6

Baseline demographics and disease characteristics.

| | Placebo<br>N = 53 | Evobrutinib<br>25 mg QD<br>N = 50 | Evobrutinib<br>75 mg QD<br>N = 51 | Evobrutinib<br>75 mg BID<br>N = 53 | Dimethyl<br>fumarate<br>N = 54 | Total<br>N = 261 |
|---|---|---|---|---|---|---|
| Age (years), mean ± SD | 41.6 ± 10.77 | 42.4 ± 9.37 | 42.9 ± 10.07 | 42.2 ± 11.50 | 42.8 ± 11.70 | 42.4 ± 10.67 |
| Female, n (%) | 39 (73.6) | 32 (64.0) | 35 (68.6) | 36 (67.9) | 39 (72.2) | 181 (69.3) |
| White, n (%)* | 53 (100.0) | 50 (100.0) | 51 (100.0) | 53 (100.0) | 54 (100.0) | 261 (100.0) |
| Type of MS, n (%) | | | | | | |
| RRMS | 47 (88.7) | 42 (84.0) | 43 (84.3) | 47 (88.7) | 49 (90.7) | 228 (87.4) |
| SPMS | 6 (11.3) | 8 (16.0) | 8 (15.7) | 6 (11.3) | 5 (9.3) | 33 (12.6) |
| Time since MS onset (years), median (min-max) | 7.5 (0.1-39.4) | 8.4 (0.2-26.4) | 11.4 (0.4-24.6) | 10.1 (0.2-39.4) | 7.3 (0.3-32.5) | 8.5 (0.1-39.4) |
| Relapses in the last 2 years, n (%) | | | | | | |
| ≤1 relapse | 26 (49.1) | 27 (54.0) | 18 (35.3) | 25 (47.2) | 20 (37.0) | 116 (44.4) |
| >1 relapse | 27 (40.9) | 23 (46.0) | 33 (64.7) | 28 (52.8) | 34 (53.0) | 145 (45.6) |
| EDSS score, mean ± SD | 3.2 ± 1.66 | 3.3 ± 1.50 | 3.5 ± 1.36 | 3.4 ± 1.63 | 3.0 ± 1.67 | 3.3 ± 1.57 |
| EDSS score, median (min-max) | 3.0 (0-6.0) | 3.0 (0-6.0) | 3.5 (1.5-6.0) | 3.0 (1.0-6.0) | 2.5 (0-6.0) | 3.0 (0.0-6.0) |
| Presence of Gd+ T1 lesions[†], n (%) | 25 (47.2) | 19 (38.0) | 17 (33.3) | 23 (43.4) | 19 (35.2) | 103 (39.5) |
| Number of Gd+ T1 lesions, mean ± SD | 1.3 ± 1.94 | 0.9 ± 2.02 | 1.6 ± 5.43 | 1.7 ± 3.40 | 2.2 ± 6.79 | 1.5 ± 4.37 |
| Volume of T2 lesions (cc), mean ± SD | 16.5 ± 13.41 | 13.8 ± 11.67 | 13.4 ± 11.20 | 19.0 ± 13.54 | 18.8 ± 17.66 | 16.37 ± 13.85 |
| SF-36 PCS score, median (min-max) | 45.8 (30.2-70.8) | 42.3 (27.1-64.6) | 41.2 (30.2-64.6) | 42.5 (20.9-61.5) | 42.7 (20.9-70.8) | 42.5 (20.9-70.8) |

BID, Twice daily; EDSS, Expanded Disability Status Scale; Gd+, gadolinium-positive; MS, Multiple sclerosis; QD, Once daily; RRMS, Relapsing-remitting multiple sclerosis; SD, Standard deviation; SPMS, Secondary progressive multiple sclerosis.
*>96% were not Hispanic or Latino; >98% of patients were from Eastern Europe (<2% from Western Europe).
[†]Used as covariate in the Negative Binomial model for Gd+ T1 lesion count.

Efficacy Outcomes

Figure 6:
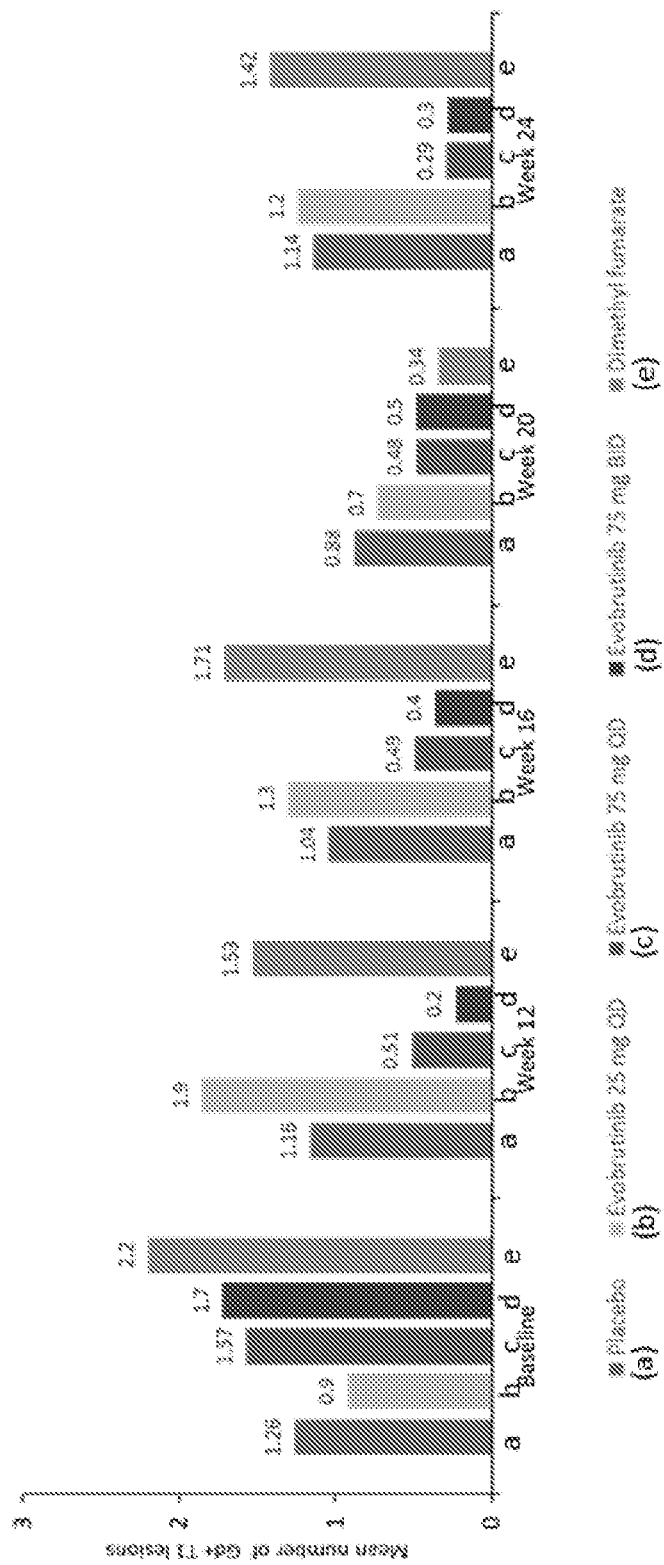
FIG. 6 is a bar graph depicting the mean number of gadolinium-enhancing lesions by week in each treatment arm of the clinical study, as further described in Example 2.

The mean (SD) Gd+ T1 lesion count per scan (weeks 12-24) was significantly reduced with evobrutinib 75 mg QD (0.42±1.17; p=0.01) and 75 mg BID (0.35±0.96; p=0.05), but not with evobrutinib 25 mg QD (1.31±3.13; p=0.22) versus placebo (1.02±1.44; p-value for lesion rate ratio adjusted for baseline lesion activity), as shown in Table 7. A significant dose response was observed (p<0.01). The mean (±SD) total Gd+ T1 lesion count (Weeks 12-24) with dimethyl fumarate was 5.78 (±29.17). The mean number of Gd+ T1 lesions by visit (baseline to Week 24) is shown in FIG. 6. Data collected on the total number of new or enlarging T2 lesions at week 24 is presented in Table 7A.

TABLE 7

MRI (Gd+ T1 lesions), clinical outcomes (ARR), and HRQOL outcomes at Week 24.

| | Placebo<br>(n = 53) | Evobrutinib 25<br>mg QD<br>(n = 50) | Evobrutinib 75<br>mg QD<br>(n = 51) | Evobrutinib 75<br>mg BID<br>(n = 53) | Dimethyl<br>fumarate<br>(n = 54) |
|---|---|---|---|---|---|
| Total number of Gd+ T1 lesions at Weeks 12, 16, 20, 24 (a) | | | | | |
| n (%) | 53 (100.0) | 50 (100.0) | 51 (100.0) | 53 (100.0) | 54 (100.00) |
| Mean ± SD | 4.07 ± 5.76 | 5.23 ± 12.52 | 1.69 ± 4.69 | 1.39 ± 3.85 | 5.78 ± 29.17 |
| Median (min-max) | 2 (0-24) | 1 (0-76) | 0 (0-27) | 0 (0-25) | 0 (0-213) |
| Gd+ T1 lesion rate (subject level) | | | | | |
| n (%) | 53 (100.0) | 50 (100.0) | 51 (100.0) | 53 (100.0) | 54 (100.00) |
| Mean ± SD | 1.02 ± 1.44 | 1.31 ± 3.13 | 0.42 ± 1.17 | 0.35 ± 0.96 | 1.45 ± 7.29 |
| Median (min-max) | 0.50<br>(0.00-6.00) | 0.25<br>(0.00-19.00) | 0.0<br>(0.00-6.75) | 0.0<br>(0.00-6.25) | 0.0<br>(0.00, 53.33) |
| Lesion Rate Ratio (b) [95% CI] | — | 1.54<br>[0.77, 3.08] | 0.38<br>[0.19, 0.79] | 0.48<br>[0.23, 1.00] | — |
| P-value (evobrutinib vs placebo) (b) | — | 0.2205 | 0.0096 | 0.0499 | — |
| Lesion rate, adjusted (b) [95% CI] | 0.71<br>[0.44, 1.15] | 1.09<br>[0.67, 1.79] | 0.27<br>[0.16, 0.47] | 0.34<br>[0.20, 0.59] | — |
| Linear trend test P-value (c) | 0.003 | | | | |

TABLE 7-continued

MRI (Gd+ T1 lesions), clinical outcomes (ARR), and HRQOL outcomes at Week 24.

| | Placebo (n = 53) | Evobrutinib 25 mg QD (n = 50) | Evobrutinib 75 mg QD (n = 51) | Evobrutinib 75 mg BID (n = 53) | Dimethyl fumarate (n = 54) |
|---|---|---|---|---|---|
| *Change in volume of T2 lesions from baseline to week 24* | | | | | |
| n (%) | 44 (83.0) | 46 (92.0) | 48 (94.1) | 47 (88.7) | 50 (92.6) |
| Mean ± SD (cc) | 0.39 ± 1.02 | 0.93 ± 1.85 | 0.01 ± 0.57 | 0.06 ± 0.50 | 0.46 ± 2.97 |
| Median (IQR) (cc) | 0.09 (−0.05, 1.02) | 0.05 (−0.05, 0.94) | −0.01 (−0.09, 0.06) | −0.02 (−0.12, 0.13) | −0.02 (−0.08, 0.18) |
| Difference in LS means of CFB in cube root of volume (cm) (d) [95% CI] | — | 0.05 [−0.21, 0.31] | −0.35 [−0.61, −0.09] | −0.35 [−0.61, −0.09] | — |
| P-value (Evobrutinib vs placebo) | — | 0.7118 | 0.0087 | 0.0085 | — |
| *New or enlarging T2 lesion rate (subject level)* | | | | | |
| n (%) | 53 (100.0) | 50 (100.0) | 51 (100.0) | 53 (100.0) | 54 (100.0) |
| Mean ± SD | 1.58 ± 1.88 | 2.08 ± 4.19 | 0.89 ± 2.71 | 0.73 ± 1.57 | 1.54 ± 5.46 |
| P-value (evobrutinib vs placebo) (b) | — | 0.4430 | 0.0863 | 0.0251 | — |
| *Qualified relapses* | | | | | |
| Number of relapses, n | 8 | 12 | 3 | 2 | — |
| Unadjusted ARR [95% CI] | 0.33 [0.14, 0.64] | 0.52 [0.27, 0.91] | 0.13 [0.03, 0.38] | 0.08 [0.01, 0.30] | — |
| P value (evobrutinib vs placebo) | — | 0.264 | 0.149 | 0.099 | — |
| Qualified relapse rate ratio based on NB model (c) [95% CI] | — | 1.75 [0.66, 4.64] | 0.36 [0.09, 1.44] | 0.26 [0.05, 1.29] | — |
| Qualified relapse rate, adjusted [95% CI] | 0.27 [0.12, 0.59] | 0.47 [0.24, 0.90] | 0.10 [0.03, 0.32] | 0.07 [0.02, 0.29] | — |
| Linear trend test P-value (d) | 0.027 | — | — | — | — |
| Proportion relapse-free, % [95% CI] | 79.2 [65.9, 89.2] | 76.0 [61.8, 86.9] | 88.2 [76.1, 95.6] | 86.8 [74.7, 94.5] | — |
| Odds ratio based on logistic model [95% CI] | — | 0.76 [0.29, 2.00] | 2.43 [0.80, 7.38] | 1.83 [0.63, 5.31] | — |
| Linear trend test p-value (e) | 0.082 | — | — | — | — |
| *Change in SF-36 Physical Component Summary (PCS) score from baseline to week 24* | | | | | |
| n (%) | 49 (92.5) | 47 (94.0) | 48 (94.1) | 48 (90.6) | 52 (96.3) |
| Mean ± SD | −1.0 ± 6.43 | 0.8 ± 5.93 | 1.5 ± 7.09 | 1.1 ± 5.22 | 1.6 ± 5.17 |
| Median (IQR) | 0.3 (−4.4, 2.5) | 0.3 (−3.4, 3.5) | 0.6 (−2.1, 3.5) | 1.3 (−2.4, 5.3) | 1.7 (−0.4, 3.9) |
| Difference in LS means of CFB in PCS score (f) [95% CI] | — | 1.73 [−0.48, 3.95] | 1.95 [−0.26, 4.16] | 1.93 [−0.27, 4.13] | — |
| P-value (Evobrutinib vs placebo) | | 0.124 | 0.084 | 0.086 | |

(a) After discounting scans affected by high dose corticosteroid use, a subject missing 1-3 scans has missing lesion counts replaced by average number of lesions detected on available scans during the first 24 weeks.
(b) Negative binomial model for total lesion count (summed over available scans through week 24) includes treatment and covariate presence/absence of Gd+ T1 lesions at baseline (or ≤13 cc, >13 cc for volume of T2 lesions at baseline), with offset equal to the log of number of scans performed. Scans collected within 3 weeks of high dose corticosteroid use considered missing. P-values unadjusted for multiplicity.
(c) Negative binomial model for relapse count includes treatment and covariate number of relapses in the 2 years before study entry (≤1, >1), with offset equal to the log of years of follow-up.
(d) Linear trend test assesses linearly decreasing trend of log lesion (or relapse) rate with increasing dose order.
(e) Linear trend test assesses linearly increasing trend of log odds of being qualified relapse-free with increasing dose.
(f) MMRM model for CFB in cube root of lesion volume (or CFB in SF-36 PCS score) includes fixed effects for treatment, visit (weeks 12, 16, 20, 24), treatment by visit interaction, covariate cube root of lesion volume at baseline (or PCS score at baseline), and AR(1) covariance structure for repeated measures. The cube root transformation was applied to T2 lesion volume data to address positive skewness. The SF-36 PCS score ranges from 0 to 100, with a higher score indicating better health.

TABLE 7A

Total Number of New or Enlarging T2 Lesions at Week 24.

|  | Placebo (n = 53) | Evobrutinib 25 mg QD (n = 50) | Evobrutinib 75 mg QD (n = 51) | Evobrutinib 75 mg BID (n = 53) | Dimethyl fumarate (n = 54) |
|---|---|---|---|---|---|
| Mean ± SD | 5.81 ± 6.95 | 6.52 ± 11.57 | 3.57 ± 10.82 | 2.26 ± 4.72 | 5.35 ± 16.67 |
| Lesion Rate Ratio (a) [95% CI] | — | 1.32 [0.65, 2.70] | 0.53 [0.26, 1.09] | 0.44 [0.21, 0.90] | — |
| P-value (evobrutinib vs placebo) (a) | — | 0.443 | 0.086 | 0.025 | — |

(a) Based on negative binomial model for total lesion count (summed over available scans through week 24).

A trend towards a reduction in ARR (unadjusted [95% confidence interval (CI)] was seen with evobrutinib 75 mg QD (0.13 [0.03-0.38]; p=0.149) and evobrutinib 75 mg BID (0.08 [95% CI 0.01-0.30]; p=0.099) versus placebo (0.33 [0.14-0.64]), with evidence of a dose response (p=0.027; NB model). Adjusted qualified relapse rates are shown in Table 7. Unadjusted ARR [95% CI] for dimethyl fumarate was 0.20 [0.07, 0.47].

The proportion of patients who qualified as relapse-free at Week 24 was 76% with evobrutinib 25 mg QD, 88% with 75 mg QD, 87% with 75 mg BID, 79% with placebo and 89% with dimethyl fumarate; the odds ratios [95% CI] versus placebo of patients being relapse-free at week 24 were 0.76 [0.29-2.00] (p=0.577) with evobrutinib 25 mg QD, 2.43 [0.80-7.38](p=0.118) with evobrutinib 75 mg QD and 1.83 [0.63-5.31] (p=0.269) with evobrutinib 75 mg BID.

Volume of T2 lesions at Week 24 decreased with evobrutinib 75 mg QD and BID (median CFB, −0.01 cc [interquartile range (IQR): −0.09, 0.06], p=0.009, and −0.02 cc [−0.12, 0.13], p=0.009, respectively) as well as dimethyl fumarate (−0.02 cc [−0.08, 0.18]) but increased with placebo and evobrutinib 25 mg, as shown in Table 7. Mean (±SD) T2 lesion rate (Weeks 12-24) was significantly reduced with evobrutinib 75 mg BID (0.73±1.57; p=0.025), but not 75 mg QD or 25 mg QD, versus placebo (1.58±1.88).

HRQoL

The SF-36 PCS score at Week 24 increased in all treatment arms versus baseline (median change), reflecting a trend for improvement. Mean CFB in SF-36 PCS score (±SD) was largest with evobrutinib 75 mg QD (1.5±7.09) and dimethyl fumarate (1.6±5.17) but no nominally significant difference between evobrutinib and placebo were observed, as shown in Table 7.

Safety Outcomes

Safety findings over 24 weeks of treatment are presented in Tables 8 through 10. Rates of treatment-emergent AEs (TEAEs) and serious TEAEs were comparable with evobrutinib 25 mg QD, 75 mg QD and placebo (46% and 4%, 44% and 2%, and 42% and 2%, respectively), but higher with evobrutinib 75 mg BID (57% and 7%; driven by asymptomatic increases in liver transaminases and lipase). TEAE and serious TEAE rates with dimethyl fumarate were 57% and 4%, respectively. The most common TEAEs (preferred term) among subjects treated with evobrutinib were nasopharyngitis, increases in alanine aminotransferase, and increases in lipase, as shown in Table 8. Grade 3 TEAEs were more frequent in the evobrutinib 75 mg BID group versus placebo (14.8% versus 11.1%) but less frequent with evobrutinib 25 mg and 75 mg QD. Most were asymptomatic, reversible transaminase elevations with no Hy's Law cases. Grade 3 alanine aminotransferase (ALT) elevations were more common with evobrutinib 75 mg BID (5.6%) versus the other evobrutinib and placebo arms (1.9% each). There were no TEAEs of grade 4 or 5. Infections and infestations and nervous system disorders occurred less frequently with evobrutinib 75 mg QD (7.5% and 9.6%) and 75 mg BID (14.8% and 7.4%) than with placebo (20.4% and 18.5%); most common infections included nasopharyngitis and urinary tract infections, as shown in Table 8.

Few subjects discontinued treatment overall; discontinuation rates due to AEs were highest with placebo (7.4% [n=4]) and evobrutinib 75 mg BID (13.0% [n=7]). Most common reasons for TEAE-related treatment discontinuation were ALT and amylase elevations with placebo, and ALT and aspartate aminotransferase (AST) elevations in all three evobrutinib arms, as shown in Table 8. There were no deaths or additional emerging safety signals.

TABLE 8

Safety outcomes at 24 weeks.

| n (%) | Placebo N = 54 (100%) | Evobrutinib 25 mg QD N = 52 (100%) | Evobrutinib 75 mg QD N = 53 (100%) | Evobrutinib 75 mg BID N = 54 (100%) | Dimethyl fumarate N = 54 (100%) |
|---|---|---|---|---|---|
| Any TEAE | 25 (46.3) | 23 (44.2) | 22 (41.5) | 31 (57.4) | 31 (57.4) |
| Any Grade 3 TEAEs* | 6 (11.1) | 2 (3.8) | 2 (3.8) | 8 (14.8) | 4 (7.4) |
| Serious TEAE | 2 (3.7) | 1 (1.9) | 1 (1.9) | 4 (7.4) | 2 (3.7) |
| TEAE leading to withdrawal | 4 (7.4) | 2 (3.8) | 2 (3.8) | 7 (13.0) | 2 (3.7) |
| TEAE related to study treatment | 10 (18.5) | 7 (13.5) | 11 (20.8) | 17 (31.5) | 24 (44.4) |
| Most common TEAEs (≥5% in any arm) by primary SOC | | | | | |
| Gastrointestinal disorders | 2 (3.7) | 4 (7.7) | 2 (3.8) | 4 (7.4) | 9 (16.7) |
| Nausea | 0 (0.0) | 2 (3.8) | 0 (0.0) | 1 (1.9) | 3 (5.6) |
| Diarrhea | 1 (1.9) | 1 (1.9) | 0 (0.0) | 0 (0.0) | 4 (7.4) |

TABLE 8-continued

Safety outcomes at 24 weeks.

| n (%) | Placebo N = 54 (100%) | Evobrutinib 25 mg QD N = 52 (100%) | Evobrutinib 75 mg QD N = 53 (100%) | Evobrutinib 75 mg BID N = 54 (100%) | Dimethyl fumarate N = 54 (100%) |
|---|---|---|---|---|---|
| General disorders and administration site conditions | 0 (0.0) | 2 (3.8) | 0 (0.0) | 1 (1.9) | 3 (5.6) |
| Infections and infestations | 11 (20.4) | 11 (21.2) | 4 (7.5) | 8 (14.8) | 7 (13.0) |
| Nasopharyngitis | 5 (9.3) | 5 (9.6) | 0 (0.0) | 4 (7.4) | 1 (1.9) |
| Urinary tract infection | 3 (5.6) | 2 (3.8) | 1 (1.9) | 0 (0.0) | 0 (0.0) |
| Injury, poisoning and procedural complications | 3 (5.6) | 1 (1.9) | 2 (3.8) | 1 (1.9) | 1 (1.9) |
| Investigations | 12 (22.2) | 5 (9.6) | 9 (17.0) | 14 (25.9) | 7 (13.0) |
| Alanine aminotransferase increased | 3 (5.6) | 1 (1.9) | 2 (3.8) | 5 (9.3) | 3 (5.6) |
| Lipase increased | 2 (3.7) | 1 (1.9) | 1 (1.9) | 5 (9.3) | 2 (3.7) |
| Aspartate aminotransferase increased | 1 (1.9) | 1 (1.9) | 2 (3.8) | 3 (5.6) | 2 (3.7) |
| Amylase increased | 3 (5.6) | 1 (1.9) | 1 (1.9) | 2 (3.7) | 1 (1.9) |
| Musculoskeletal and connective tissue disorders | 6 (11.1) | 5 (9.6) | 3 (5.7) | 4 (7.4) | 6 (11.1) |
| Arthralgia | 1 (1.9) | 1 (1.9) | 2 (3.8) | 0 (0.0) | 4 (7.4) |
| Nervous system disorders | 10 (18.5) | 5 (9.6) | 2 (3.8) | 4 (7.4) | 6 (11.1) |
| Headache | 1 (1.9) | 3 (5.8) | 2 (3.8) | 1 (1.9) | 1 (1.9) |
| Multiple sclerosis relapse | 3 (5.6) | 1 (1.9) | 0 (0.0) | 0 (0.0) | 0 (0.0) |
| Respiratory, thoracic and mediastinal disorders | 0 (0.0) | 1 (1.9) | 2 (3.8) | 0 (0.0) | 3 (5.6) |
| Skin and subcutaneous tissue disorders | 0 (0.0) | 0 (0.0) | 2 (3.8) | 3 (5.6) | 7 (13.0) |
| Erythema | 0 (0.0) | 0 (0.0) | 0 (0.0) | 0 (0.0) | 7 (13.0) |
| Vascular disorders | 1 (1.9) | 0 (0.0) | 0 (0.0) | 0 (0.0) | 13 (24.1) |
| Flushing | 0 (0.0) | 0 (0.0) | 0 (0.0) | 0 (0.0) | 12 (22.2) |
| Most common TEAEs leading to withdrawal (≥2% in any arm) by primary SOC | | | | | |
| Any withdrawal | 4 (7.4) | 2 (3.8) | 2 (3.8) | 7 (13.0) | 2 (3.7) |
| Investigations | 2 (3.7) | 1 (1.9) | 1 (1.9) | 6 (11.1) | 0 (0.0) |
| Alanine aminotransferase increased | 1 (1.9) | 1 (1.9) | 1 (1.9) | 4 (7.4) | 0 (0.0) |
| Aspartate aminotransferase increased | 0 (0.0) | 1 (1.9) | 1 (1.9) | 2 (3.7) | 0 (0.0) |

SOC, System organ class; TEAE, Treatment-emergent adverse event.
*There were no Grade 4 TEAEs, cases of benign tumors, malignancy or deaths.

TABLE 9

Additional safety outcomes at 24 weeks.

| Safety Outcome | Placebo N = 54 (100%) | Evobrutinib 25 mg QD N = 52 (100%) | Evobrutinib 75 mg QD N = 53 (100%) | Evobrutinib 75 mg BID N = 54 (100%) | Dimethyl fumarate N = 54 (100%) |
|---|---|---|---|---|---|
| Infections and infestations that qualify as serious | 1 (1.9) | 0 (0.0) | 0 (0.0) | 0 (0.0) | 1 (1.9) |
| Neoplasms (benign/malignant/unspecified) | 1 (1.9)* | 0 (0.0) | 0 (0.0) | 0 (0.0) | 1 (1.9)** |
| Lymphocyte count decreased | 0 (0.0) | 0 (0.0) | 0 (0.0) | 1 (1.9) | 2 (3.7) |

*Lung neoplasm;
**gastric cancer and gastric neoplasm

TABLE 10

Lymphopaenia at week 24 (laboratory evaluation).
Shifts from normal (grade 0) to highest grade lymphopaenia
(weeks 0-24)

| Worst Grate, n (%) | Placebo N = 52 | Evobrutinib 25 mg QD N = 49 | Evobrutinib 75 mg QD N = 52 | Evobrutinib 75 mg BID N = 53 | Dimethyl fumarate N = 51 |
|---|---|---|---|---|---|
| Grade 1 | 3 (5.8) | 1 (2.0) | 2 (3.8) | 3 (5.7) | 10 (19.6) |
| Grade 2 | 0 (0.0) | 0 (0.0) | 0 (0.0) | 1 (1.9) | 7 (13.7) |
| Grade 3 | 0 (0.0) | 0 (0.0) | 0 (0.0) | 0 (0.0) | 0 (0.0) |
| Grade 4 | 0 (0.0) | 0 (0.0) | 0 (0.0) | 0 (0.0) | 0 (0.0) |

Analysis of Results

After 24 weeks of treatment, the total number of Gd+ T1 lesions, measured at Weeks 12, 16, 20 and 24, was significantly reduced with evobrutinib 75 mg QD and 75 mg BID, compared with placebo. At both doses, a trend for a reduced ARR over 24 weeks versus placebo was also observed, and a nominally significant evobrutinib dose-response was shown for both endpoints. Evobrutinib 75 mg BID was associated with greater overall occurrences of TEAEs (including Grade 3) and serious TEAEs compared to the placebo and lower-dose evobrutinib arms, but was well-tolerated overall. Improvements in SF-36 PCS score from baseline over 24 weeks were observed for all evobrutinib arms and the dimethyl fumarate arm, but a comparison between evobrutinib and placebo was not nominally significant.

B- and T-cells are well-established targets in MS treatment and, given the key role of aberrant B- and T-cell functions and interactions in autoimmune pathologies including MS, BTK inhibition is a promising therapeutic regimen in these conditions. Pre-clinical studies have shown that evobrutinib inhibits B-cell activation and maturation from naïve to antigen-activated B cells in vitro and ex vivo and has potential to reduce CNS inflammation and demyelination and ameliorate disease severity (based on clinical scoring) in B- and T-cell-mediated EAE mouse models (Torke 2018; Boschert 2017). In addition, evobrutinib was shown to potently inhibit BCR- and FcR-mediated signalling in a variety of human cellular assays and to prevent B cell activation in vivo, with robust activity in RA and SLE models (Haselmayer 2018). Preclinical EAE models have shown that depletion of un-activated B-cells involved in the regulation of antigen-presenting cells (APCs) may translate into exacerbations associated with reduced frequency of regulatory T-cells and a pronounced pro-inflammatory differentiation of myeloid CD11b+ APCs (Lehmann-Horn et al. 2011). Thus, prevention of B-cell activation without depletion of naïve B cells may be of particular interest for MS therapies. Importantly, evobrutinib's mechanism of action (MoA) does not only target B-cells and thereby B-T-cell interactions (adaptive immune system) but has also demonstrated effects on the innate immune system by inhibiting the activation, differentiation and polarisation of M1 macrophages and by promoting the M2 macrophage-phenotype in vitro (Alankus 2018). Macrophages are the most abundant cell type in inflammatory, demyelinating MS lesions and M1 macrophages are a key mediator of inflammation while M2 macrophages have anti-inflammatory properties (Vogel et al. 2013; Mikita et al. 2011). The findings of this Phase II study indicate that evobrutinib's MoA affecting the adaptive as well as the innate immune system may translate into efficacy in patients with RMS or SPMS with superimposed relapses.

The safety profile of evobrutinib within this Phase II study, was overall comparable to that observed within Phase II studies of other B cell-targeting and immunomodulatory agents (Kappos et al. 2008; Cohen et al. 2016; Olsson et al. 2014; Sorensen et al. 2014; Selmaj et al. 2013; Kappos et al. 2011; Coles et al. 2008; Comi et al. 2008; Hauser et al. 2008; O'Connor et al. 2006), some of which are approved treatments for relapsing MS (Guarnera, Bramanti, and Mazzon 2017; O'Connor et al. 2016; Bomprezzi 2015). Infection rates with evobrutinib were lower than those with placebo as well as those observed with B-cell depleting agents in comparable MS Phase II studies (Sorensen et al. 2014; Kappos et al. 2011; Hauser et al. 2008).

The highest (75 mg BID) dose of evobrutinib used in the study led to an increased frequency of Grade 3 ALT elevation, in the absence of Hy's law or liver failure cases. While no statistical comparisons to evobrutinib or placebo were made, the open-label dimethyl fumarate treatment arm was included as a high-efficacy oral compound reference arm and outcomes will provide valuable insights into the design of future MS trials.

There were some limitations to this study. For instance, this study included patients with SPMS with relapses in addition to those with RRMS, the implications of which are not yet known. Overall, the trial population was older, with longer disease duration and fewer relapses than in other Phase 2 trials in MS (Kappos 2011) which could lead to underestimating the treatment effect on radiological and clinical measures of disease activity. Further, patient numbers within each treatment arm were low and there were two patients who were considered T1 Gd+ outliers, which may have had a substantial impact on analyses, despite the application of robust statistical methods: one patient treated with dimethyl fumarate had a total of 230 Gd+ T1 lesions over 4 scans and a second patient treated with evobrutinib 25 mg QD had 76 Gd+ T1 lesions over 4 scans (all other patients had <29 total Gd+ T1 lesions over 4 scans). An additional limitation to the study was that it was powered for MRI as an outcome measure. These limitations can be further evaluated in post-hoc analyses and future larger studies.

In summary, it has been demonstrated that two of the assessed evobrutinib doses significantly reduced Gd+ T1 lesions versus placebo and that treatment with evobrutinib was overall well-tolerated. None of the three evobrutinib doses were associated with hematological abnormalities, such as lymphopenia.

REFERENCES

Alankus, Y. B. 2018. 'BTK inhibition prevents inflammatory macrophage differentiation: a potential role in MS', ECTRIMS.

Bomprezzi, R. 2015. 'Dimethyl fumarate in the treatment of relapsing-remitting multiple sclerosis: an overview', Ther Adv Neurol Disord, 8: 20-30.

Boschert, U.; Crandall, T.; Pereira, A.; Higginbotham, G.; Wu, Y.; Grenningloh, R.; Savinainen, A.; Bender, A. 2017. 'T cell mediated experimental CNS autoimmunity induced by PLP in SJL mice is modulated by Evobrutinib (M2951) a novel Bruton's tyrosine kinase inhibitor', ECTRIMS Online Library.

Cohen, J. A., D. L. Arnold, G. Comi, A. Bar-Or, S. Gujrathi, J. P. Hartung, M. Cravets, A. Olson, P. A. Frohna, K. W. Selmaj, and Radiance Study Group. 2016. 'Safety and efficacy of the selective sphingosine 1-phosphate receptor modulator ozanimod in relapsing multiple sclerosis (RADIANCE): a randomised, placebo-controlled, phase 2 trial', Lancet Neurol, 15: 373-81.

Coles, A. J., D. A. Compston, K. W. Selmaj, S. L. Lake, S. Moran, D. H. Margolin, K. Norris, and P. K. Tandon. 2008. 'Alemtuzumab vs. interferon beta-1a in early multiple sclerosis', N Engl J Med, 359: 1786-801.

Comi, G., A. Pulizzi, M. Rovaris, O. Abramsky, T. Arbizu, A. Boiko, R. Gold, E. Havrdova, S. Komoly, K. Selmaj, B. Sharrack, M. Filippi, and L. A. Q. Study Group. 2008. 'Effect of laquinimod on MRI-monitored disease activity in patients with relapsing-remitting multiple sclerosis: a multicentre, randomised, double-blind, placebo-controlled phase IIb study', Lancet, 371: 2085-92.

Haselmayer, P. 2018. 'Efficacy and Pharmacodynamic Modeling of the BTK Inhibitor Evobrutinib in Autoimmune Disease Models', The Journal of Immunology.

Hauser, S. L., E. Waubant, D. L. Arnold, T. Vollmer, J. Antel, R. J. Fox, A. Bar-Or, M. Panzara, N. Sarkar, S. Agarwal, A. Langer-Gould, C. H. Smith, and Hermes Trial Group. 2008. 'B-cell depletion with rituximab in relapsing-remitting multiple sclerosis', N Engl J Med, 358: 676-88.

Kappos, L., R. Gold, D. H. Miller, D. G. Macmanus, E. Havrdova, V. Limmroth, C. H. Polman, K. Schmierer, T. A. Yousry, M. Yang, M. Eraksoy, E. Meluzinova, I. Rektor, K. T. Dawson, A. W. Sandrock, G. N. O'Neill, and B. G. Phase IIb Study Investigators. 2008. 'Efficacy and safety of oral fumarate in patients with relapsing-remitting multiple sclerosis: a multicentre, randomised, double-blind, placebo-controlled phase IIb study', Lancet, 372: 1463-72.

Lehmann-Horn, K., E. Schleich, D. Hertzenberg, A. Hapfelmeier, T. Kumpfel, N. von Bubnoff, R. Hohlfeld, A. Berthele, B. Hemmer, and M. S. Weber. 2011. 'Anti-CD20 B-cell depletion enhances monocyte reactivity in neuroimmunological disorders', J Neuroinflammation, 8: 146.

Mikita, J., N. Dubourdieu-Cassagno, M. S. Deloire, A. Vekris, M. Biran, G. Raffard, B. Brochet, M. H. Canron, J. M. Franconi, C. Boiziau, and K. G. Petry. 2011. 'Altered M1/M2 activation patterns of monocytes in severe relapsing experimental rat model of multiple sclerosis. Amelioration of clinical status by M2 activated monocyte administration', Mult Scler, 17: 2-15.

O'Connor, P., G. Comi, M. S. Freedman, A. E. Miller, L. Kappos, J. P. Bouchard, C. Lebrun-Frenay, J. Mares, M. Benamor, K. Thangavelu, J. Liang, P. Truffinet, V. J. Lawson, J. S. Wolinsky, Group Teriflunomide Multiple Sclerosis Oral Trial, and Texas the Mri-Ac in Houston. 2016. 'Long-term safety and efficacy of teriflunomide: Nine-year follow-up of the randomized TEMSO study', Neurology, 86: 920-30.

Olsson, T., A. Boster, O. Fernandez, M. S. Freedman, C. Pozzilli, D. Bach, O. Berkani, M. S. Mueller, T. Sidorenko, E. W. Radue, and M. Melanson. 2014. 'Oral ponesimod in relapsing-remitting multiple sclerosis: a randomised phase II trial', J Neurol Neurosurg Psychiatry, 85: 1198-208.

Selmaj, K., D. K. Li, H. P. Hartung, B. Hemmer, L. Kappos, M. S. Freedman, O. Stuve, P. Rieckmann, X. Montalban, T. Ziemssen, L. Z. Auberson, H. Pohlmann, F. Mercier, F. Dahlke, and E. Wallstrom. 2013. 'Siponimod for patients with relapsing-remitting multiple sclerosis (BOLD): an adaptive, dose-ranging, randomised, phase 2 study', Lancet Neurol, 12: 756-67.

Sorensen, P. S., S. Lisby, R. Grove, F. Derosier, S. Shackelford, E. Havrdova, J. Drulovic, and M. Filippi. 2014. 'Safety and efficacy of ofatumumab in relapsing-remitting multiple sclerosis: a phase 2 study', Neurology, 82: 573-81.

Torke, S. 2018. 'Inhibition of Bruton's tyrosine kinase selectively prevents antigen-activation of B cells and ameliorates B cell-mediated experimental autoimmune encephalomyelitis', ECTRIMS.

Vogel, D. Y., E. J. Vereyken, J. E. Glim, P. D. Heijnen, M. Moeton, P. van der Valk, S. Amor, C. E. Teunissen, J. van Horssen, and C. D. Dijkstra. 2013. 'Macrophages in inflammatory multiple sclerosis lesions have an intermediate activation status', J Neuroinflammation, 10: 35.

Example 3: Pharmacokinetic Parameters Determined by Computer Simulation for Orally Administered Evobrutinib to a Human Patient with Multiple Sclerosis Computer simulations were performed to determine pharmacokinetic parameters for orally administered evobrutinib in a human patient. A range of dosing amounts of evobrutinib were evaluated according to a once daily oral administration (QD) protocol for evobrutinib and a twice daily oral administration (BID) protocol for evobrutinib. The computer simulations included analysis for evobrutinib administered under fasted conditions and under fed conditions. Pharmacokinetic parameters of one thousand patients per dosing regimen were simulated. Pharmacokinetic parameters analysed included $C_{max}$, AUC, and Cave over 24 hours at steady state. The exposure response model relating evobrutinib AUC over 24 hours at steady state and annualized relapse rate (ARR) was used to simulate the ARR under alternative evobrutinib dosing regimens. The simulated ARR distribution (displayed graphically as a smoothed density) corresponded to 100 means (i.e., 100 clinical trials) each corresponding to 650 patients. The simulation assumes one-year follow-up for all patients. Results are provided below.

Figure 7:
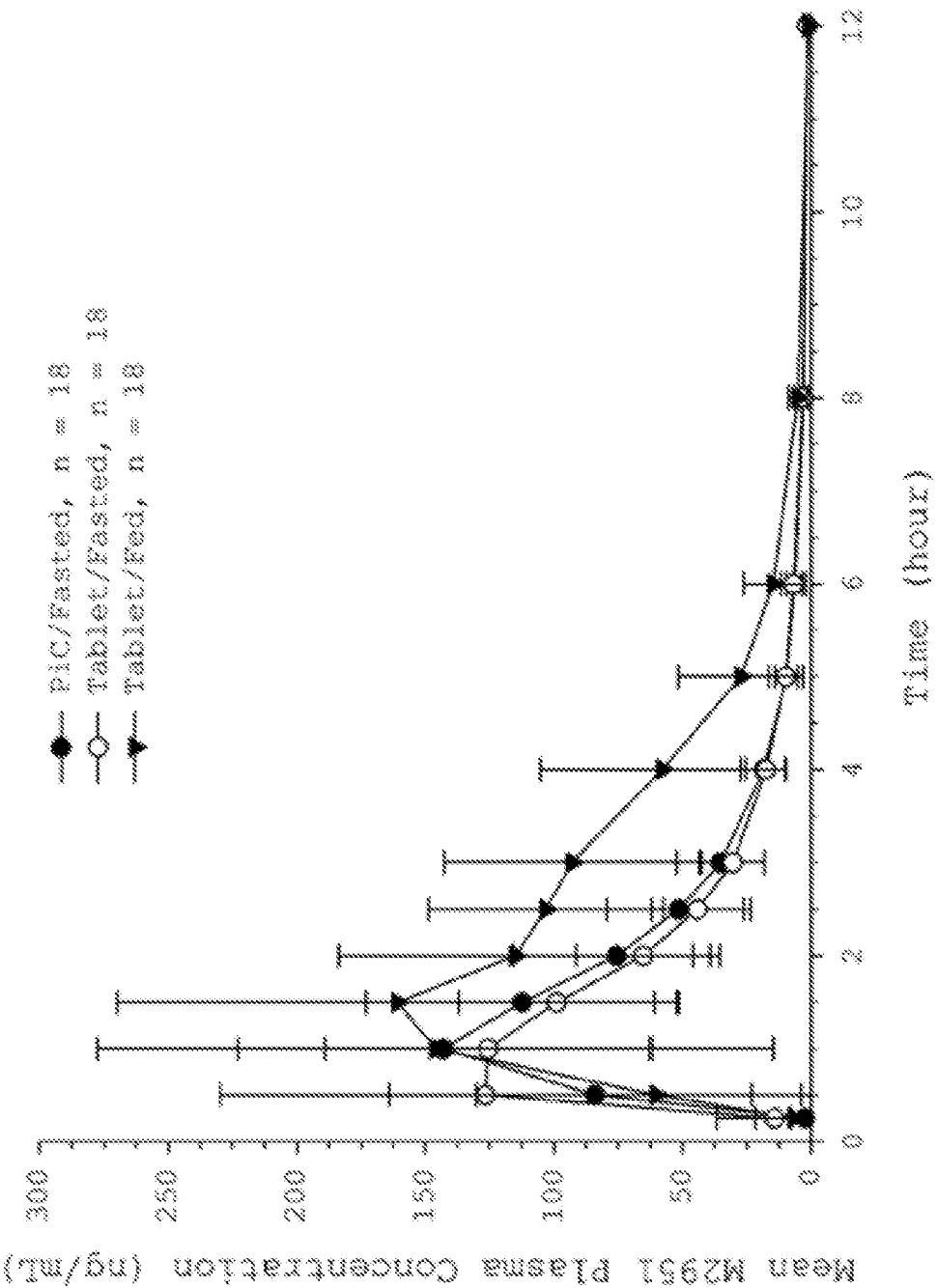
FIG. 7 is a graph depicting mean plasma concentrations for evobrutinib (ng/mL) for when administered as (i) a powder-in-capsule to a human patient under fasted conditions, (ii) a tablet to a human patient under fasted conditions, and (iii) a tablet to a human patient under fed conditions, as further described in Example 3.

The simulations of this example are based on the results of a clinical trial to investigate the relative bioavailability of a tablet formulation compared to powder-in-capsule of evobrutinib, including a food effect evaluation in healthy volunteers. The determined mean plasma concentrations for evobrutinib (ng/mL) are provided in the graph of FIG. 7 for administration of evobrutinib as (i) a powder-in-capsule to a human patient under fasted conditions, (ii) a tablet to a human patient under fasted conditions, and (iii) a tablet to a human patient under fed conditions. Table 11 below provides AUC and $C_{max}$ results determined for oral administration of evobrutinib as (i) a powder-in-capsule to a human patient under fasted conditions, (ii) tablet to a human patient under fasted conditions, and (iii) a tablet to a human patient under fed conditions.

TABLE 11

Pharmacokinetic Parameters

| Treatment[b]/Statistic | $AUC_{0-\infty}{}^{a}$ (ng * h/mL) | $AUC_{0-t}$ (ng * h/mL) | $C_{max}$ (ng/mL) | $AUC_{0-24\,h}$ (ng * h/mL) |
|---|---|---|---|---|
| PiC/Fasted | | | | |
| n | 16 | 18 | 18 | 18 |
| Geo Mean | 297.2 | 281.8 | 149.44 | 282.1 |
| Geo CV % | 40.8 | 40.2 | 48.5 | 40.2 |
| Tablet/Fasted | | | | |
| n | 15 | 18 | 18 | 18 |
| Geo Mean | 252.9 | 269.8 | 160.53 | 274.3 |
| Geo CV % | 39.9 | 41.5 | 44.5 | 41.1 |

TABLE 11-continued

| | Pharmacokinetic Parameters | | | | |
|---|---|---|---|---|---|
| Treatment[b]/ Statistic | $AUC_{0-\infty}$[a] (ng * h/mL) | $AUC_{0-t}$ (ng * h/mL) | $C_{max}$ (ng/mL) | $AUC_{0-24\,h}$ (ng * h/mL) | |
| Tablet/Fed | | | | | |
| n | 17 | 18 | 18 | 18 | |
| Geo Mean | 438.7 | 449.2 | 203.64 | 454.3 | |
| Geo CV % | 31.2 | 33.1 | 46.4 | 33.0 | |

Tables 12 and 13 below provide AUC, $C_{max}$, and Cave results computed for oral administration of evobrutinib to a human patient under conditions specified in the table.

TABLE 12

Pharmacokinetic Profile Summary at Steady State

| | Evobrutinib Dose (mg) Regimen | | | | |
|---|---|---|---|---|---|
| Summary Statistic | 10 mg BID Fed | 20 mg QD Fed | 45 mg BID Fed | 100 mg BID Fed | 200 mg QD Fed |
| | $C_{max}$ (ng/mL) at Steady State | | | | |
| Mean (SD) | 33 (16.7) | 63 (32.7) | 147 (75.2) | 327 (167) | 632 (326.9) |
| Median | 30 | 57 | 133 | 295 | 573 |
| CV% | 51 | 52 | 51 | 51 | 52 |
| Geo Mean | 29 | 55 | 128 | 285 | 550 |
| Geo CV % | 58 | 59 | 58 | 58 | 59 |
| Q1; Q3 | 21; 42 | 40; 81 | 94; 187 | 209; 416 | 401; 806 |
| Min; Max | 3; 124 | 6; 246 | 13; 558 | 28; 1240 | 57; 2456 |
| | $AUC_{0-24\,h}$ (ng/mL · hr) at Steady State | | | | |
| Mean (SD) | 213 (116.6) | 213 (116.6) | 959 (524.6) | 2132 (1165.9) | 2132 (1165.9) |
| Median | 186 | 186 | 836 | 1858 | 1858 |
| CV % | 55 | 55 | 55 | 55 | 55 |
| Geo Mean | 187 | 187 | 840 | 1867 | 1867 |
| Geo CV % | 55 | 55 | 55 | 55 | 55 |
| Q1; Q3 | 134; 267 | 134; 267 | 603; 1200 | 1340; 2666 | 1340; 2666 |
| Min; Max | 35; 998 | 35; 998 | 156; 4492 | 346; 9982 | 346; 9982 |
| | $C_{ave}$ (ng/mL) over 24 hr at Steady State | | | | |
| Mean (SD) | 9 (4.9) | 9 (4.9) | 40 (21.9) | 89 (48.6) | 89 (48.6) |
| Median | 8 | 8 | 35 | 77 | 77 |
| CV% | 55 | 55 | 55 | 55 | 55 |
| Geo Mean | 8 | 8 | 35 | 78 | 78 |
| Geo CV % | 55 | 55 | 55 | 55 | 55 |
| Q1; Q3 | 6; 11 | 6; 11 | 25; 50 | 56; 111 | 56; 111 |
| Min; Max | 1; 42 | 1; 42 | 6; 187 | 14; 416 | 14; 416 |

TABLE 13

Pharmacokinetic Profile Summary at Steady State

| | Evobrutinib Dose (mg) Regimen | | | | |
|---|---|---|---|---|---|
| Summary Statistic | 15 mg BID Fasted | 30 mg QD Fasted | 45 mg BID Fed | 150 mg BID Fasted | 300 mg QD Fasted |
| | $C_{max}$ (ng/mL) at Steady State | | | | |
| Mean (SD) | 41 (17.5) | 79 (34.3) | 147 (75.2) | 405 (175.3) | 789 (343.1) |
| Median | 37 | 73 | 133 | 374 | 729 |
| CV % | 43 | 43 | 51 | 43 | 43 |
| Geo Mean | 37 | 72 | 128 | 371 | 720 |
| Geo CV % | 45 | 45 | 58 | 45 | 45 |
| Q1; Q3 | 28; 49 | 54; 97 | 94; 187 | 280; 493 | 542; 967 |
| Min; Max | 7; 133 | 13; 263 | 13; 558 | 67; 1325 | 131; 2627 |
| | $AUC_{0-24\,h}$ (ng/mL · hr) at Steady State | | | | |
| Mean (SD) | 215 (117.4) | 215 (117.4) | 959 (524.6) | 2146 (1173.7) | 2146 (1173.7) |
| Median | 187 | 187 | 836 | 1870 | 1870 |
| CV % | 55 | 55 | 55 | 55 | 55 |
| Geo Mean | 188 | 188 | 840 | 1879 | 1879 |

TABLE 13-continued

Pharmacokinetic Profile Summary at Steady State

| Summary Statistic | Evobrutinib Dose (mg) Regimen | | | | |
|---|---|---|---|---|---|
| | 15 mg BID Fasted | 30 mg QD Fasted | 45 mg BID Fed | 150 mg BID Fasted | 300 mg QD Fasted |
| Geo CV % | 55 | 55 | 55 | 55 | 55 |
| Q1; Q3 | 135; 268 | 135; 268 | 603; 1200 | 1349; 2684 | 1349; 2684 |
| Min; Max | 35; 1005 | 35; 1005 | 156; 4492 | 348; 10049 | 348; 10049 |
| $C_{ave}$ (ng/mL) at Steady State | | | | | |
| Mean (SD) | 9 (4.9) | 9 (4.9) | 40 (21.9) | 89 (48.9) | 89 (48.9) |
| Median | 8 | 8 | 35 | 78 | 78 |
| CV % | 55 | 55 | 55 | 55 | 55 |
| Geo Mean | 8 | 8 | 35 | 78 | 78 |
| Geo CV % | 55 | 55 | 55 | 55 | 55 |
| Q1; Q3 | 6; 11 | 6; 11 | 25; 50 | 56; 112 | 56; 112 |
| Min; Max | 9 (4.9) | 9 (4.9) | 40 (21.9) | 89 (48.9) | 89 (48.9) |

Figure 8:
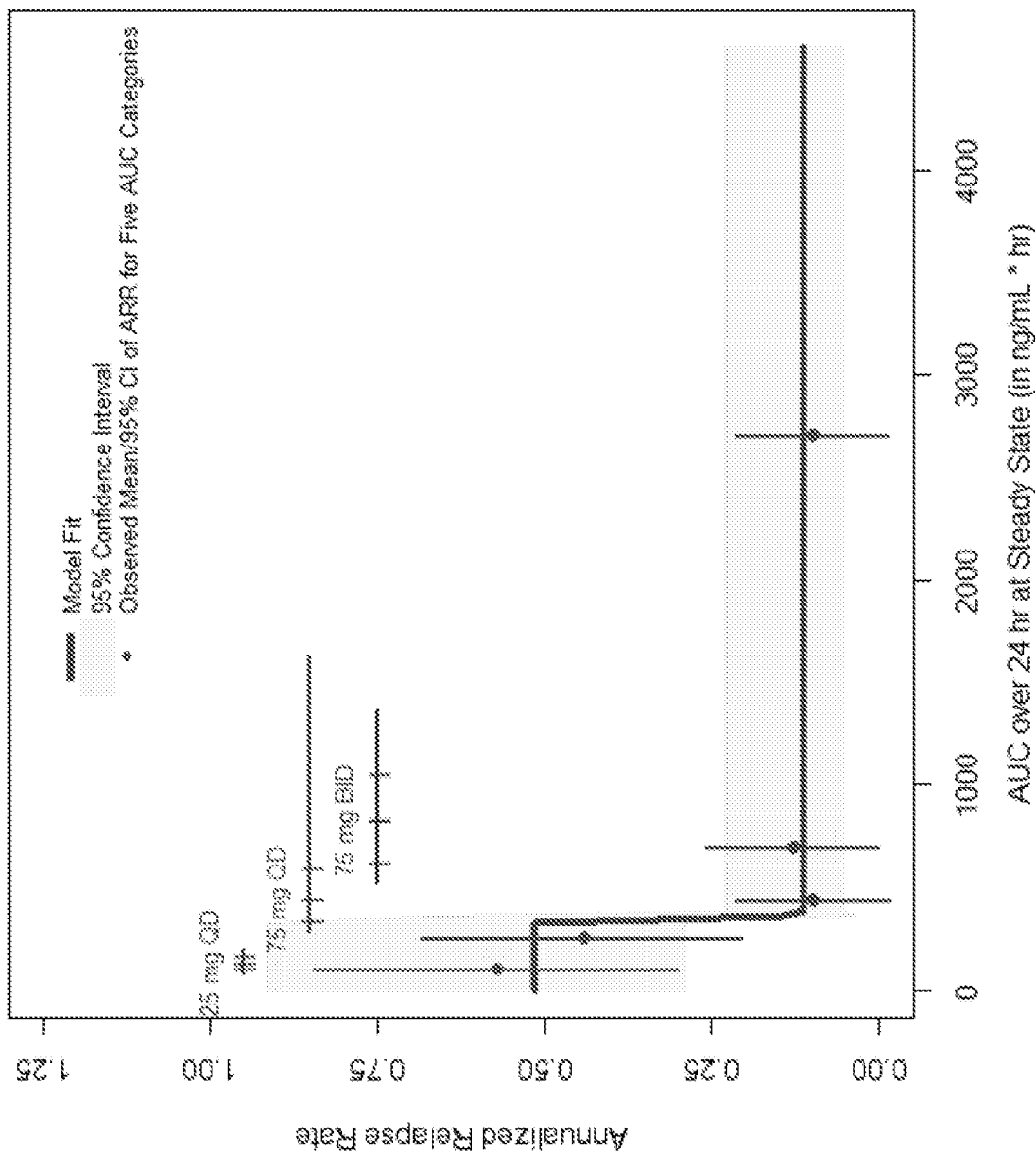
FIG. 8 is a graph depicting annualized relapse rate results generated from the simulation described in Example 3. Horizontal lines in the graph correspond to the middle 80% of the distribution of AUC by dose/regimen. The three ticks are the 1st, 2nd (median), and 3rd quartiles. Exposure categories correspond to quintiles of the AUC distribution for patients on evobrutinib. Observed means (points) are plotted at the mid-point of the corresponding AUC exposure group. Data shown correspond to a total sample size of 154 patients.

Annualized relapse rate (ARR) generated from the simulation is displayed graphically in FIG. 8. Results shown in FIG. 8 correspond to a total sample size of 154 patients.

Figure 10:
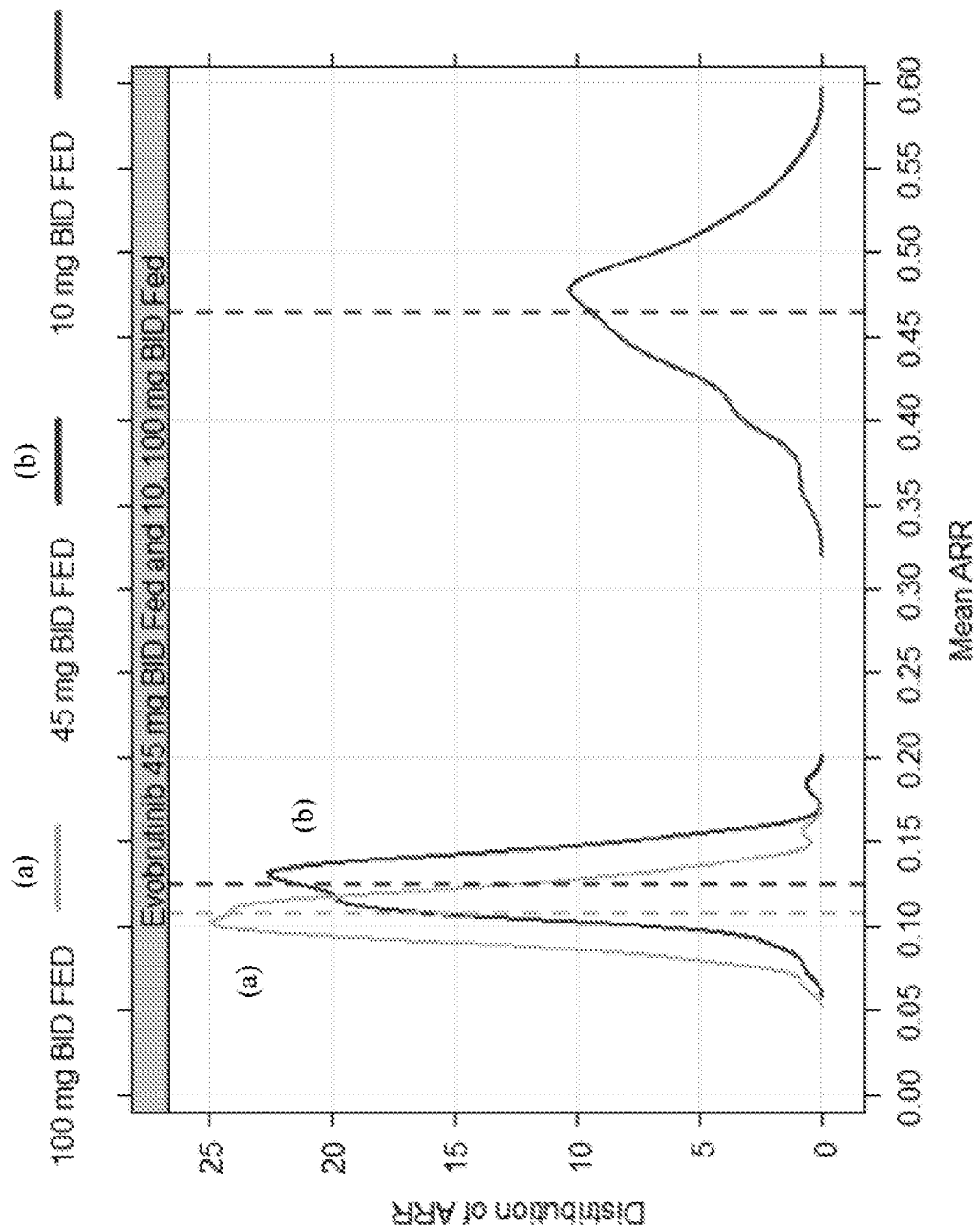
FIG. 10 is a graph depicting simulated distribution of annualized relapse rate for evobrutinib administered at (i) 10 mg BID under fed state, (ii) 45 mg BID under fed state, or (iii) 100 mg BID under fed state, as further described in Example 3.
Figure 11:
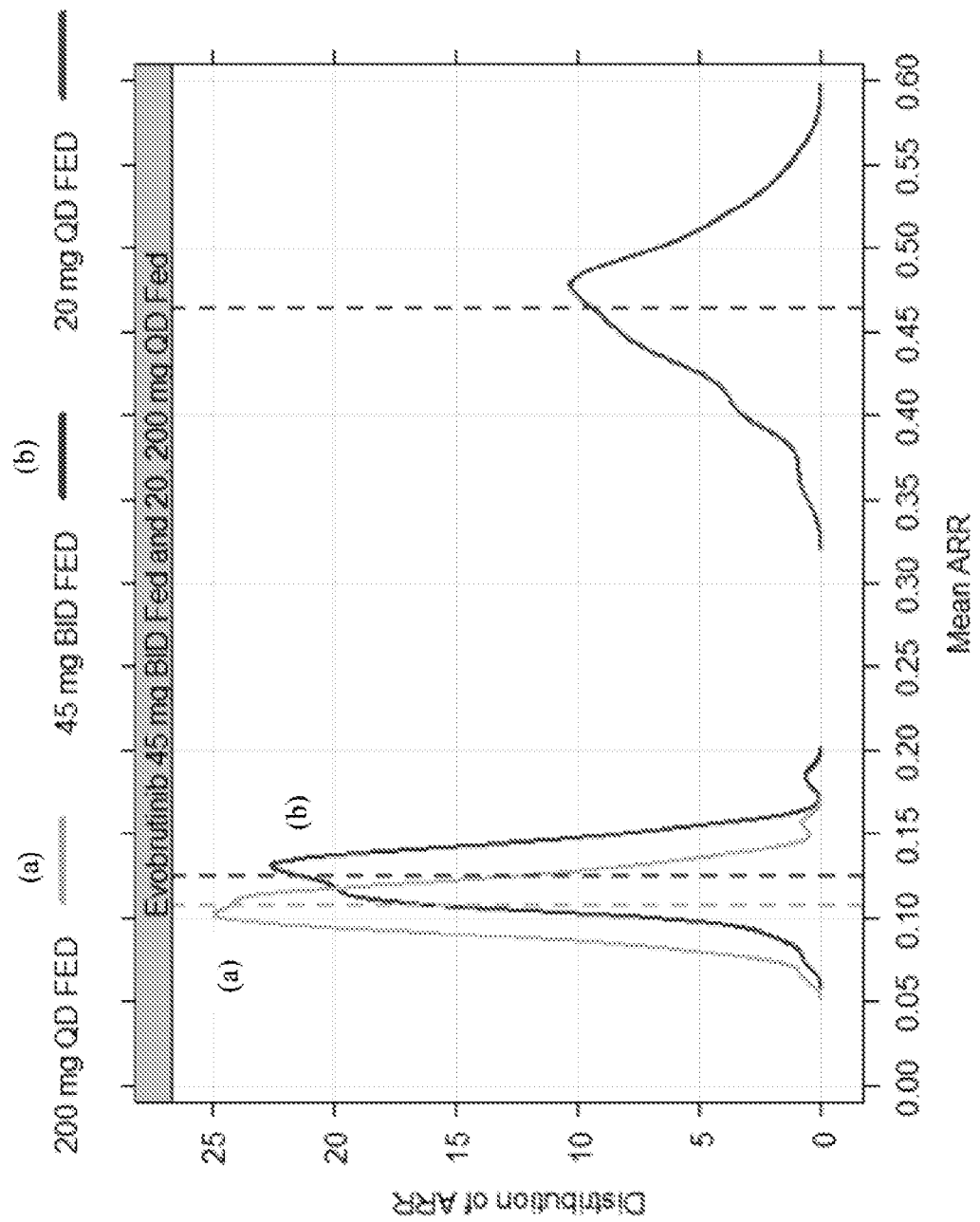
FIG. 11 is a graph depicting simulated distribution of annualized relapse rate for evobrutinib administered at (i) 45 mg BID under fed state, (ii) 20 mg QD under fed state, or (iii) 200 mg QD under fed state, as further described in Example 3.
Figure 12:
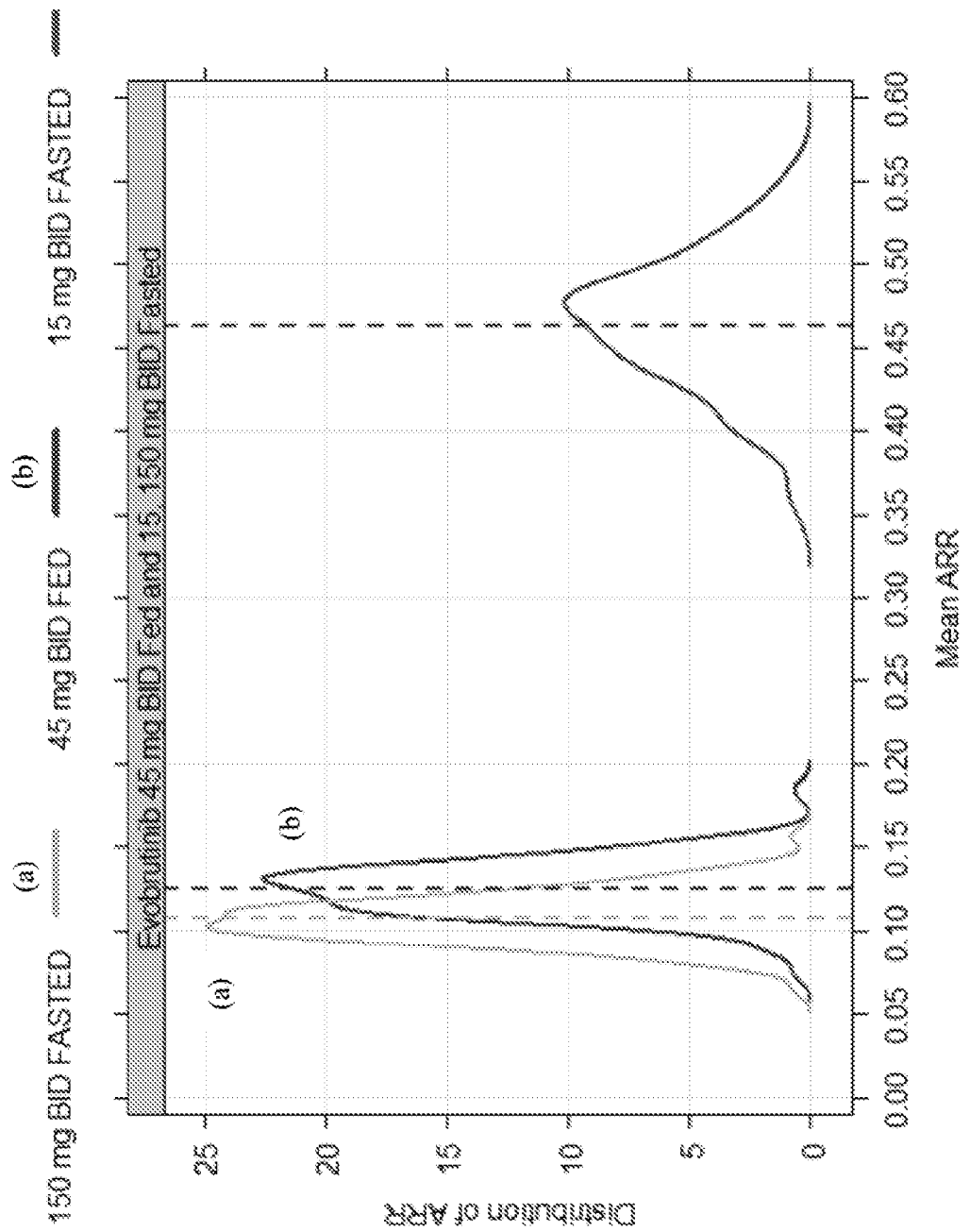
FIG. 12 is a graph depicting simulated distribution of annualized relapse rate for evobrutinib administered at (i) 45 mg BID under fed state, (ii) 15 mg BID under fasted state, or (iii) 150 mg BID under fasted state, as further described in Example 3.
Figure 13:
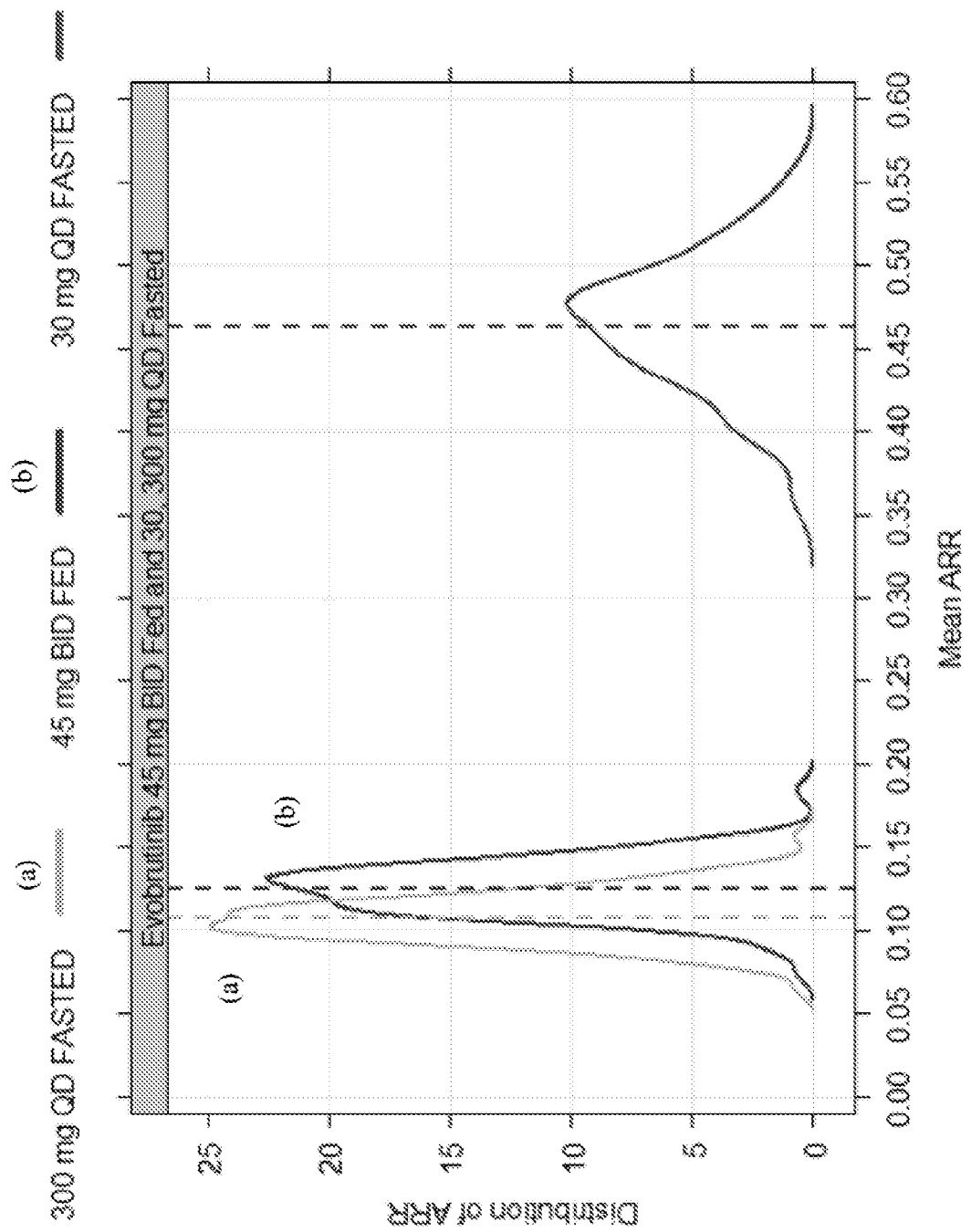
FIG. 13 is a graph depicting simulated distribution of annualized relapse rate for evobrutinib administered at (i) 45 mg BID under fed state, (ii) 30 mg QD under fasted state, or (iii) 300 mg QD under fasted state, as further described in Example 3.

Results of simulated distribution of annualized relapse rate for evobrutinib administered under various conditions are displayed graphically in FIGS. 9-13. In particular, FIG. 9 provides a graph depicting simulated distribution of annualized relapse rate for evobrutinib administered at (i) 75 mg BID under fasted state or (ii) 45 mg BID under fed state. FIG. 10 provides a graph depicting simulated distribution of annualized relapse rate for evobrutinib administered at (i) 10 mg BID under fed state, (ii) 45 mg BID under fed state, or (iii) 100 mg BID under fed state. FIG. 11 provides a graph depicting simulated distribution of annualized relapse rate for evobrutinib administered at (i) 45 mg BID under fed state, (ii) 20 mg QD under fed state, or (iii) 200 mg QD under fed state. FIG. 12 provides a graph depicting simulated distribution of annualized relapse rate for evobrutinib administered at (i) 45 mg BID under fed state, (ii) 15 mg BID under fasted state, or (iii) 150 mg BID under fasted state. FIG. 13 provides a graph depicting simulated distribution of annualized relapse rate for evobrutinib administered at (i) 45 mg BID under fed state, (ii) 30 mg QD under fasted state, or (iii) 300 mg QD under fasted state. For the results in each of FIGS. 9-13, the data is a distribution (displayed graphically as a smoothed density) of 100 means each corresponding to 650 subjects, where overall mean (vertical dashed line) corresponds to 100×650 patients and the simulation that generated the results assumes one year follow-up for all patients.

Example 4: Phase III, Randomized, Parallel Group, Double-Blind, Double Dummy, Active-Controlled Study of Treatment of Relapsing Multiple Sclerosis in Human Patients Using Evobrutinib This study has been designed to examine the effects of evobrutinib in human patients suffering from relapsing multiple sclerosis (RMS) in a phase III clinical study. The study is configured as a randomized, parallel group, double-blind, double dummy, active-controlled study in subjects with RMS to evaluate evobrutinib in comparison to an active control group that receives interferon beta-1a (marketed under the brand name AVONEX®).

Trial Design

Human subjects meeting all inclusion criteria and no exclusion criteria are to be enrolled into the trial as eligible participants. Eligible participants will be randomized 1:1 to treatment with evobrutinib, or interferon beta-1a (AVONEX®), stratified by region and Baseline EDSS. For patients receiving evobrutinib, a 45 mg dose of evobrutinib will be orally administered twice per day with a meal. For patients receiving interferon beta-1a, the interferon beta-1a (AVONEX®) will be administered intramuscularly at the highest approved dose of 30 μg once a week. Blinding will be accomplished using a double dummy design.

A 96 week Treatment Period will be preceded by a 4 week Screening Period and followed by a 4 week Safety Follow Up after treatment discontinuation, unless the participant continues into a planned optional open label, long term extension. At the end of the 96 week main study, participants who choose to enter the planned open label extension (OLE) will be switched to treatment with evobrutinib. The long-term open label extension study may be conducted under a separate protocol (or be incorporated with a protocol amendment) for those completing 96 weeks of treatment. Participants experiencing initial clinical progression between week 84-96 will be assigned an additional 12 weeks of treatment to allow confirmation of the disability progression.

An optional interim analysis for sample size re-estimation, based on 12 week CDP data pooled from the present study and its twin, may occur, triggered when 50% of planned 12 week CDP events have been observed. The IA will evaluate conditional power (CP; probability of rejecting the null hypothesis at the final analysis conditional on observed data) associated with the 12 week CDP endpoint based on pooled data. The IDMC will use a pre-specified rule, specified in the IDMC Charter or related document, to determine whether CP is in the promising zone $CP_{min} \leq CP < CP_{max}$, and if so, by how much to increase enrollment up to a maximum of 35%. (Here $CP < CP_m$ in represents the unfavorable/futility zone, while $CP \geq CP_{max}$ represents the favorable/efficacy zone.)

Patient selection criteria are described in more detail below, along with exemplary study objectives, outcome measures, and assessments and procedures for evaluating efficacy and safety.

Patient Selection Criteria

Only subjects meeting all inclusion criteria and no exclusion criteria are to be enrolled into the trial.

Inclusion Criteria
1. Are about 18 to 55 years of age, at the time of signing the informed consent
2. Diagnosed with RMS (relapsing-remitting multiple sclerosis [RRMS] or secondary progressive multiple sclerosis [SPMS] with relapses) in accordance with 2017 Revised McDonald criteria.
3. With clinical activity defined as:
   a. At least 2 documented clinical attacks within the last 2 years prior to Screening, or
   b. One documented clinical attack in the year prior to Screening, or
   c. One gadolinium-enhancing lesion or 2 new T2 lesions in the year prior to Screening
4. Have an EDSS score of 0 to 5.5 at Baseline
   a. Participants with an EDSS score ≤2 at Screening are only eligible for participation if their disease duration (time since onset of symptoms) is no more than 10 years
5. Are neurologically stable for ≥30 days prior to both Screening and Baseline
6. If the Participant is Female, then:
   Is not pregnant or breastfeeding, and at least one of the following conditions applies:
   Not a WOCBP
   or
   If a WOCBP, use a highly effective contraceptive method (i.e., with a failure rate of <1% per year), preferably with low user dependency, for the following time periods:
   Before the first dose of the study intervention(s), if using hormonal contraception:
   Has completed at least one 4-week cycle of an oral contraception pill and either had or has begun her menses
   or
   Has used a depot contraceptive or extended-cycle oral contraceptive for at least 28 days and has a documented negative pregnancy test using a highly sensitive assay.
   During the intervention period
      After the study intervention period (i.e., after the last dose of study intervention is administered) for at least after the last dose of study intervention
      For teratogenic drugs when there is chance of drug-drug interaction with hormonal contraceptive such that the contraception may not be reliable, then an alternate method with <1% failure rate per year must be used.
      The investigator evaluates the effectiveness of the contraceptive method in relationship to the first dose of study intervention.
   Have a negative pregnancy test, as required by local regulations, before the first dose of study intervention.
7. Can give signed informed consent.

Exclusion Criteria
1. Participants diagnosed with Progressive MS, in accordance with the 2017 Revised McDonald criteria, as follows:
   a. Participants with Primary Progressive MS, or
   b. Participants with Secondary Progressive MS without evidence of relapse.
2. Disease duration >10 years in participants with an EDSS ≤2.0 at Screening.
3. Immunologic disorder other than MS, or any other condition requiring oral, IV, intramuscular, or intra-articular corticosteroid therapy, with the exception of well-controlled Type 2 diabetes mellitus or well controlled thyroid disease.
4. History or current diagnosis of other neurological disorders that may mimic MS, including but not limited to: neuromyelitis optica, transverse myelitis, bilateral optic neuritis of simultaneous onset, Lyme disease, HTLV-1-associated myelopathy, untreated vitamin B12 deficiency, neurosarcoidosis, and cerebrovascular disorders.
5. History or current diagnosis of progressive multifocal leukoencephalopathy (PML).
6. Active, clinically significant viral, bacterial, or fungal infection, or any major episode of infection requiring hospitalization or treatment with parenteral anti-infectives within 4 weeks of Screening, or completion of oral anti-infectives within 2 weeks before or during Screening, or a history of recurrent infections (i.e., 3 or more of the same type of infection in a 12 month rolling period). Vaginal candidiasis, onychomycosis, and genital or oral herpes simplex virus considered by the Investigator to be sufficiently controlled would not be exclusionary.
7. The participant:
   Has a history of or current diagnosis of active tuberculosis (TB), or
   Is currently undergoing treatment for latent TB infection (LTBI), or
   Has an untreated LTBI as determined by documented results within 3 months of the Screening visit of a positive TB skin or T.SPOT test with purified protein derivative with induration ≥5 mm, or
   Has current household contacts with active TB, or
   Has a positive QuantiFERON®-TB test at Screening. Participants with documented completed appropriate LTBI treatment would not be excluded and are not required to be tested.
8. Individuals with indeterminate or positive QuantiFERON®-TB test results felt to represent a false positive result by the Investigator, with no clinical features consistent with active TB, will be evaluated with T-SPOT.TB at the request of the Investigator. In this case, if the T-SPOT.TB is negative, the individual may be enrolled after approval by the medical monitor.
9. Individuals with a diagnosis of hemochromatosis, Wilson's disease, alpha-1-antitrypsin deficiency, or any other chronic liver disease including Gilbert's disease will be a contraindication for participation in the study
10. Individuals who meet laboratory criteria for suspected hemochromatosis using ferritin and transferrin saturation values would always be exclusionary. Elevated ferritin (>300 ug/L ferritin and >50% transferrin saturation in males; >200 ug/L ferritin and >40% transferrin saturation in females) OR transferrin saturation per the diagnostic criteria would be excluded from the study. If ferritin is elevated without transferrin saturation, then the individuals will be excluded if the levels are >500 ug/L
11. Individuals with sickle cell anemia, thalassemia and/or any chronic blood disorder requiring blood transfusions will be excluded from the study.
12. History of splenectomy at any time, or any major surgery within 2 months prior to Screening
13. History of myocardial infarction or cerebrovascular event within 6 months prior to Screening, or current active angina pectoris, history of or current congestive heart failure New York Heart Association (NYHA) Class III or Class IV, seizures (remote infantile febrile seizures are not exclusionary), untreated hypertension, GI bleeding, or any other significant active medical condition in the Investigator's opinion.
14. A history of attempted suicide within 6 months prior to Screening or a positive response to items 4 or 5 of Columbia-Suicide Severity Rating Scale (C-SSRS).
15. An episode of major depression within the last 6 months prior to Screening (clinically stable minor depression is not exclusionary).
16. History of cancer with the following exceptions:
    a. A history of non-melanoma skin cancer Stage 0 (in situ) or Stage 1, considered cured >five years is not exclusionary.
    b. A history of in situ cervical cancer, considered cured >five years, is not exclusionary.
17. Clinically significant abnormality on ECG.
18. An active infective process or any other clinically significant abnormality on Screening Chest X-ray (CXR) taken within 4 weeks of the first dose, per Investigator opinion. If a CXR has been taken within the previous 3 months and results are available and normal, the CXR does not need to be carried out.
19. Contraindication to interferon beta-1a (AVONEX®) or incompatibility with interferon beta-1a (AVONEX®) use, including;
    a. Hypersensitivity to natural or recombinant interferon-0, or to any excipients;
    b. Cessation of interferon therapy due to poor tolerability or suboptimal response.
20. IV or oral glucocorticoids within 4 weeks prior to randomization (inhaled corticosteroids are allowed).
21. Treatment with monthly IV methylprednisolone.
22. Treatment with p-interferons or glatiramer acetate within 4 weeks prior to randomization
23. Treatment with dimethyl fumarate within 4 weeks provided lymphocyte count is >1000 cells/L prior to randomization
24. Treatment with teriflunomide within 12 weeks or after the accelerated elimination procedure prior to randomization
25. Use of lymphocyte trafficking blockers (natalizumab or fingolimod) within 48 weeks prior to randomization.
26. Use of intravenous (IV) Ig or plasmapheresis within 12 weeks prior to randomization.
27. Treatment with rituximab, ocrelizumab, and any other B cell depleting therapy, BTK inhibitors (including evobrutinib), mitoxantrone, or lymphocyte-depleting therapies (e.g., alemtuzumab, anti-CD4, cladribine, cyclophosphamide, total body irradiation, bone marrow transplantation).
28. Treatment with dalfampridine (fampridine, Ampyra) unless on a stable dose for >30 days prior to randomization
29. On anticoagulation, fish oil supplements, or antiplatelet therapy other than daily aspirin for cardioprotection
30. Participants currently receiving (or unable to stop using prior to receiving the first dose of study intervention) potent (strong to moderate) inducers of CYP3A (must stop at least 3 weeks prior), medications or herbal supplements known to be potent (strong to moderate) inhibitors of cytochrome P450 3A (CYP3A) (must stop at least 1 week prior), or drugs mainly metabolized by CYP3A with a narrow therapeutic index (must stop at least 1 day prior)
31. Participation in any investigational drug study within 6 month or 5 half-lives of the investigational drug, whichever is longest, prior to Screening.
32. Any of the following:
    a. History of or positive for human immunodeficiency virus (HIV) at Screening
    b. History of or positive for hepatitis C antibody and/or hepatitis C RNA by polymerase chain reaction (PCR) at Screening
    c. Positive for hepatitis B surface antigen (HBsAg) at Screening
    d. For participants who are negative for HBsAg at Screening but are anti-hepatitis B surface antibody positive and/or anti-hepatitis B core antibody positive at Screening, reflex testing for hepatitis B virus DNA (HBV DNA) by PCR will be performed:
        1. Hepatitis B antibody positive participants who have detectable HBV DNA >20 IU/mL are excluded.
        2. Hepatitis B antibody positive participants who are HBV DNA negative OR have detectable HBV DNA <20 IU/mL are not excluded from the study. However, these participants will have HBV DNA measured by PCR at visits.
    Participants who have previously been vaccinated for Hepatitis B will not be tested for anti-hepatitis B surface antibody, as they will be positive for anti-hepatitis B surface antibody as the protective consequence of vaccination.
33. Estimated glomerular filtration rate (eGFR) by the 4-variable Modification of Diet in Renal Disease equation of <45 mL/min/1.73 $m^2$ or any renal condition that would preclude the administration of gadolinium (e.g., acute kidney injury).
34. ALT, AST, amylase, or lipase >2× above upper limit of normal (ULN) of laboratory reference range, total bilirubin >1.5×ULN, any other clinically significant laboratory abnormality.
35. Significant cytopenia, including neutrophil count <1,500/$mm^3$, platelet count <75,000/$mm^3$, absolute lymphocyte count <1,000/$mm^3$, or a white blood cell count <3500/$mm^3$.
36. Any allergy, contraindication, or inability to tolerate Avonex or evobrutinib or any of their excipients
37. Inability to comply with MRI scanning, including contraindications to MRI such as known allergy or other contraindications to gadolinium contrast media, claustrophobia, presence of a pacemaker, cochlear implants, ferromagnetic devices or clips, intracranial vascular clips, insulin pumps, nerve stimulators
38. Vaccination with live or live-attenuated virus vaccine within 1 month prior to Screening
39. Regular alcohol consumption within about 6 months prior to the study defined as: For an average weekly intake of >about 14 units for males or >about 7 units for females. One unit is equivalent to 8 g of alcohol: a half pint (~240 mL) of beer, 1 glass (125 mL) of wine or 1 (25 mL) measure of spirits.

Exemplary Study Objectives & Outcome Measures

Exemplary study objectives and outcome measures are provided in Table 14 below.

TABLE 14

| Objectives | Endpoints (Outcome Measures) |
| --- | --- |
| Primary | |
| To demonstrate superior efficacy with evobrutinib compared to interferon beta-1a (AVONEX ®) | Annualized relapse rate (ARR) based on qualified relapses at Week 96 in participants with RMS |
| Secondary | |
| To evaluate the efficacy of evobrutinib relative to that of interferon beta-1a (AVONEX ®) on disability progression | Time to first occurrence of 12 week confirmed EDSS progression over 96 weeks |
| To evaluate the efficacy of evobrutinib relative to that of interferon beta-1a (AVONEX ®) on MRI lesion parameters | Total number of new and/or enlarging T2 lesions based on assessments at Week 24, Week 48, and Week 96 |
| To evaluate the efficacy of evobrutinib relative to that of interferon beta-1a (AVONEX ®) on MRI lesion parameters | Total number of T1 Gd+ lesions based on assessments at Week 24, Week 48, and Week 96. |
| To evaluate the efficacy of evobrutinib relative to that of interferon beta-1a (AVONEX ®) on disability progression | Time to first occurrence of 24 week confirmed EDSS progression over 96 weeks |
| To characterize the safety and tolerability of evobrutinib. | Safety as assessed by the nature, severity, and occurrence of adverse events (AEs); vital signs; electrocardiograms (ECGs); absolute concentrations and change from Baseline in immunoglobulin (Ig) levels; absolute numbers of B cells; and clinical laboratory safety parameters up to Week 100 |
| Additional Potential Objectives | Additional Potential Endpoints (Outcome Measures) |
| To demonstrate the effect of evobrutinib compared to interferon beta-1a (AVONEX ®) on clinical parameters | 24 week confirmed disability improvement status during 96 weeks assessed at Baseline, every 12 weeks up to Week 96<br>12 week confirmed disability improvement status during 96 weeks assessed at Baseline, every 12 weeks up to Week 96 |
| To demonstrate additional clinical efficacy with evobrutinib compared to interferon beta-1a (AVONEX ®) | ARR based on qualified relapses from first treatment to Week 48. |
| To evaluate the efficacy of evobrutinib relative to that of interferon beta-1a (AVONEX ®) on relapse activity. | Time to first qualified relapse up to Week 96<br>Relapse free status at Week 96 |
| To evaluate the efficacy of evobrutinib relative to that of interferon beta-1a (AVONEX ®) on disease activity | Disease activity free status at Week 96 as measured by:<br>Qualifying relapse-free status<br>12 and 24 week confirmed EDSS progression free status |
| To evaluate the efficacy of evobrutinib relative to that of interferon beta-1a (AVONEX ®) on MRI parameters | Mean number of T1 Gd+ lesions per scan based on assessments up to Week 96<br>Change in volume of T1 Gd+ lesions from Baseline to Week 96 based on assessments at Baseline, Weeks 24, 48, and 96<br>Mean number of active T2 lesions per scan based on assessments up to Week 96<br>Change in volume of T2 lesions from Baseline to Week 96 based on assessments at Baseline, Weeks 24, 48, and 96<br>New or enlarging T2 lesions free status<br>New Gd+ T1 lesions free status<br>Percentage change in brain volume (BV) from Week 24 to Week 96 assessed at Baseline, Weeks 24, 48, and 96<br>Mean number of combined unique active (CUA) lesions per scan based on assessments at up to Week 96<br>Total number of CUA lesions based on assessments at Week 24, Week 48, and Week 96<br>Total number of new T1 hypo-intense lesions based on assessments at Week 24, Week 48, and Week 96<br>CUA lesion free status at Week 96 based on assessments at Baseline, Week 24, Week 48, and Week 96 |

TABLE 14-continued

| Objectives | Endpoints (Outcome Measures) |
|---|---|
| To evaluate the efficacy of evobrutinib relative to that of interferon beta-1a (AVONEX ®) on patient reported symptoms and functional status | Change from Baseline in PROMIS physical function score at Week 48 and at Week 96 based on assessments at Baseline, every 12 weeks up to Week 96<br>Change from Baseline in PROMIS fatigue score at Week 48 and at Week 96 based on assessments at Baseline, every 12 weeks up to Week 96<br>Change in Patient Reported Outcomes based on assessments at Baseline, every 24 weeks up to Week 96:<br>Medical Outcomes Study 36 Item Short Form Health Survey (SF-36v2)<br>EuroQoL 5 Dimension 5 Levels (EQ 5D-5L) |
| To evaluate the efficacy of evobrutinib relative to that of interferon beta-1a (AVONEX ®) on cognitive function | Change from Baseline in Symbol Digit Modalities Test (SDMT) score at Week 48 and at Week 96 based on assessments up to Week 96 |
| To demonstrate the effect of evobrutinib compared to interferon beta-1a (AVONEX ®) on functional and cognitive measures | Time to ≥20% sustained increase in T25-FW during 96 weeks assessed at Baseline, every 12 weeks up to Week 96<br>Time to ≥20% sustained increase in 9-HPT during 96 weeks assessed at Baseline, every 12 weeks up to Week 96<br>Change in SDMT from Baseline to Week 96 based on assessments at Baseline, every 12 weeks up to Week 96<br>Time to first occurrence of 12 week confirmed disability progression based on a composite score defined by:<br>A 12 week confirmed EDSS progression (at least 0.5- or 1.0- point change, depending on the Baseline EDSS) or;<br>A 12 week confirmed worsening (≥20%) in Timed 25-Foot Walk (T25-FW) versus Baseline or;<br>A 12 week confirmed worsening (≥20%) in 9 Hole Peg Test (9-HPT) versus Baseline. |
| To characterize the PK profile of evobrutinib in participants with MS | PK parameters: $CL_{/F}$, $V_{z/F}$, $C_{max}$, AUC at Day 1, Week 2, 4, 8, 12, 24, 48, and 72 |
| To describe the exposure-response relationship between evobrutinib and efficacy endpoints cross-sectionally or longitudinally | Evobrutinib PK parameters<br>Efficacy endpoints: ARR, EDSS, MRI lesions (T1 Gd+ lesions and active T2 lesion count), and other efficacy endpoints |
| To describe the exposure-response relationship between evobrutinib and safety endpoints | Evobrutinib PK parameters at Baseline, Week 4, 8, 12, 24, 48, and 72<br>Safety endpoints: alanine aminotransferase (ALT) and aspartate aminotransferase (AST) at Baseline, Week 4, 8, 12, 24, 48, and 72 |
| To describe the exposure-response relationship between evobrutinib and biomarkers | Evobrutinib PK parameters and Biomarker endpoints:<br>BTK occupancy at Baseline, Week 4, 8, 12, and 24<br>B, T, and NK cells and subsets at Baseline, Week 4, 24, and 48 |
| To assess relationship between candidate disease biomarker and disease activity or treatment response | Level of biomarkers of disease with disease activity/treatment response at Baseline, Week 12, 24, 48, 72, 96; and upon relapse/disease progression (unscheduled) |
| To evaluate the relationship of the novel biomarkers of hepatic function compared to standard clinical chemistry endpoints (ALT). | Levels of novel biomarkers of hepatic function compared to ALT at Baseline, Week 2, 4, 6, 8, 10, 12, 14, 16, 20, 24, 28, 32, 36, 40, 44, 48, 52, 56, 60, 64, 68, 72, 76, 80, 84, 88, 92, and 96 |
| To assess the effect of evobrutinib on gene expression in whole blood | Gene expression at Baseline, Week 4, 8, 12, 24, 48, and 96 |

Exemplary Assessments and Procedures for Evaluating Efficacy

Exemplary assessments and procedures for evaluating efficacy include the following:

Neurological Assessment

The Examining Investigator will perform the neurological examination, document the functional system scores (FSS) scores, and assess EDSS scores. The examining Investigator will also be responsible for performing and documenting results.

Qualified Relapse

A qualifying relapse is the occurrence of new or worsening neurological symptoms attributable to MS (for >24 hours, no fever, infection, injury, AEs, and preceded by a stable or improving neurological state for ≥30 days). The relapse should be accompanied by an increase of ≥0.5

EDSS, or 2 points increase on 1 of the FSS, or 1 point increase on ≥2 of the FSS. The change must affect the selected FSS (i.e., pyramidal, ambulation, cerebellar, brainstem, sensory, or visual, excluding bladder or bowel).

Episodic spasms, sexual dysfunction, fatigue, and mood change will not suffice to establish a relapse.

Adjudication of qualified relapses (regardless of whether they are identified during a scheduled or unscheduled visit) will be performed by the Adjudication Committee based on pre-specified criteria, applied to data collected by Investigator, in a blinded fashion. Any assessments needed to confirm the relapse should be performed, and details of the relapse should be documented within the relevant section(s) of the eCRF. The criteria for a qualified relapse should be clear and there should be documentation of how each potential relapse did or did not meet the criteria. Participants who have a documented relapse during treatment are not required to discontinue study intervention unless they meet any of the criteria for discontinuation from the study intervention.

The annualized relapse rates over 96 weeks will be calculated based on qualified relapses.

Disability progression and Expanded Disability Status Scale

Disability progression is defined as an increase of ≥1.0 point from the Baseline EDSS score that is not attributable to another etiology (e.g., fever, concurrent illness, or concomitant medication) when the Baseline score is less than 5.5, and ≥0.5 when the Baseline score is 5.5. Disability progression is considered sustained when the initial increase in the EDSS is confirmed at a regularly scheduled visit at least 12 weeks or 24 weeks, after the initial documentation of neurological worsening.

Sustained disability progression, confirmed for both 12 and 24 weeks, after the initial documentation of neurological worsening, will be analyzed as secondary endpoints.

Timed Twenty-Five Foot Walk

The Timed Twenty-Five Foot Walk (T25-FW) is a quantitative mobility and leg function performance test based on a timed 25-foot walk. The participant is directed to one end of a clearly marked 25-foot course and is instructed to walk 25 feet as quickly as possible, but safely. The time is calculated from the initiation of the instruction to start and ends when the participant has reached the 25-foot mark. The task is immediately administered again by having the participant walk back the same distance. Participants may use assistive devices when doing this task. T25-FW will be administered by the Investigator or qualified designee.

A worsening of ≥20% is considered to have occurred in this task, when the time it takes to complete the task is longer by equal to or more than 20% than the time it took at Baseline. The worsening is considered confirmed at 12 weeks if the following assessment (at a scheduled visit of 12 weeks or more after the initial observed worsening) confirms it.

Nine Hole Peg Test

The 9-HPT is a brief, standardized, quantitative test of upper extremity function. Both the dominant and non-dominant hands are tested twice. The participant is seated at a table with a small, shallow container holding nine pegs and a wood or plastic block containing nine empty holes. On a start command when a stopwatch is started, the participant picks up the nine pegs one at a time as quickly as possible, puts them in the nine holes, and, once they are in the holes, removes them again as quickly as possible one at a time, replacing them into the shallow container. The total time to complete the task is recorded. Two consecutive studies with the dominant hand are immediately followed by two consecutive studies with the non-dominant hand. 9-HPT will be administered by the Investigator or qualified designee.

A worsening of >20% is considered to have occurred in this task, when the time it takes to complete the task is longer by equal to or more than 20% than the time it took at Baseline. The worsening is considered confirmed at 12 weeks if the following assessment (at a scheduled visit of 12 weeks or more after the initial observed worsening) confirms it.

Brain Magnetic Resonance Imaging Scans

If a participant discontinues the study more than 4 weeks after his or her most recent MRI, during the double-blind phase of treatment period, an MRI may be obtained at the Discontinuation Visit. The Screening MRI scan should be acquired before randomization and dosing to allow for the readouts to be read by the central MRI reader (approximately 14 days).

Magnetic resonance imaging is a useful tool for monitoring central nervous system (CNS) lesions in MS.

Different MRI derived parameters have been related to clinical activity and T1 weighted gadolinium-enhancing (T1 Gd+) lesions or new and/or enlarging hyperintense T2 (active T2) lesions have been related to relapses. Other MRI readout such as T1 hypo-intense lesions are reflective of long-term brain damage (black holes). Combined unique active lesions are defined as new T1 Gd+ lesions or active T2 lesions (without double counting). It is hypothesized that changes in brain volume may reflect brain atrophy as a result of MS-related tissue loss and may thereby correlate with long-term clinical outcome in these participants.

Brain MRI scans will be performed according to a standardized imaging protocol before and after the administration of single-dose gadolinium.

Images will be assessed and reported by an independent, blinded, centralized MRI reading service. The assessment will be performed in the absence of clinical information. All MRI images will be reviewed and reported locally by a radiologist for safety. If a scheduled MRI scan is delayed or an unscheduled MRI scan is indicated, care should be taken to avoid the participant being exposed to gadolinium more than once in a 4 week period, i.e., it may be necessary to cancel the MRI scan at the next scheduled visit (all other assessments should be completed at the visit as normal). If the next scheduled visit is the Week 96, the Week 96 MRI scan should be performed as soon as the 4 week period since previous exposure to gadolinium has elapsed.

Gadolinium will be used to enhance T1-weighted lesions and to optimize clarity and accuracy of reporting. As gadolinium is excreted renally, participants with acute renal insufficiency (eGFR <45 mL/min/1.73 m$^2$) will be excluded from the study.

Patient Reported Outcomes (PRO)

PRO data will be collected at the study visit with an electronic tablet device. The tablet with the PRO instruments will be distributed by the Investigator staff and completed in their entirety by the participant.

PROs will be administered prior to administration of study intervention and prior to any other study assessment(s) to ensure the validity of the instruments is not compromised, and data quality meet requirements of the Guidance for Industry Patient-Reported Outcome Measures: Use in Medical Product Development to Support Labeling Claims.

PRO data will be elicited from participants in this study to better characterize the clinical profile of evobrutinib.

Patient Reported Outcomes Measurement Information System

The National Institute of Health Patient Reported Outcomes Measurement Information System (NIH PROMIS) comprises an extensive set of item banks and short-form measures created from the item banks that assess physical, mental, and social aspects of health in adults and children, including symptoms such as pain, fatigue, and sleep disturbance, and health domains such as physical function.

The PROMIS PF item bank was identified as having great potential for the evobrutinib program due to several factors, despite limited previous use in MS, and lack of an MS-specific short form. First, the content includes all key aspects of physical function domain, such as IADL, lower extremity (mobility), back and neck (central), and upper extremity functioning domains. Second, the development process of PROMIS items included a rigorous development and calibration process, ensuring the technical quality of items. Further, items capture the full continuum of PF, from low to high levels, which is a useful characteristic for capturing changes over time.

The PROMIS Fatigue item bank includes 95 items assessing the experience (frequency, duration and intensity) as well as the impacts of fatigue on physical, mental and social activities. Psychometric properties of this bank have been established across different clinic populations. An 8-item short-form specific to MS, derived based on input from clinicians (n=36) and participants with MS (n=48), is available.

The PROMIS approach offers flexibility in the selection of items and how these are administered, including use of bespoke measures, fixed short forms, or computerized adaptive testing. PROMIS based short forms for physical functioning and fatigue are currently undergoing FDA qualification as a drug development tool (DDT) in MS.

Medical Outcomes Study 36-Item Short Form Survey Instrument

The Medical Outcomes Study 36-Item Short Form Survey Instrument (SF-36v2) is a 36-item questionnaire that measures 8 areas of participant reported health rated from 0 to 100 for a total score ranging from 0 to 800. The areas are:
Physical function
Role limitations due to health problems
Bodily pain
Social functioning
General mental health
Role limitations due to emotional problems
Energy/fatigue
General health perceptions The instrument will be used to calculate a normalized score for each of the 8 health domain scales, a physical component summary (PCS) score, and a mental component summary (MSC) score, with higher scores indicating better health.

EuroQoL 5 Dimension 5 Levels

The EuroQoL 5 Dimension (EQ-5D) is a standardized instrument developed as a measure of health-related quality of life that can be used in a wide range of health conditions and treatments. The 5-level EQ-5D version (EQ-5D-5L) was introduced in 2009 to improve the instrument's sensitivity and to reduce ceiling effects, as compared to the EuroQoL 5 Dimension 3 Levels (EQ-5D-3L). The EQ-5D-5L essentially consists of 2 pages: the EQ-5D descriptive system and the EQ visual analogue scale (EQ VAS).

The descriptive system comprises five dimensions: mobility, self-care, usual activities, pain/discomfort and anxiety/depression. Each dimension has 5 levels: no problems, slight problems, moderate problems, severe problems and extreme problems. The levels of the five dimensions can be combined into a 5-digit number that describes the patient's health state.

EQ-5D-5L health states, defined by the EQ-5D-5L descriptive system, may be converted into a single health utility index value using country specific value sets. Health utility values facilitate the calculation of quality-adjusted life years that are used to inform pharmacoeconomic evaluations of health care interventions.

The EQ VAS records the respondent's self-rated health on a 20 cm vertical, visual analogue scale with endpoints labelled 'the best health you can imagine' and 'the worst health you can imagine'. This information can be used as a quantitative measure of health as judged by the individual respondents.

Higher scores on both EQ-5D-5L health utility values and EQ VAS represent a better HRQoL.

Symbol Digit Modalities Test

The SDMT has demonstrated sensitivity in detecting not only the presence of cognitive impairment, but also changes in cognitive functioning over time and in response to treatment. The SDMT is brief, easy to administer, and involves a simple substitution task that normal children and adults can easily perform. Using a reference key, the examinee has 90 seconds to pair specific numbers with given geometric figures. Responses can be written or oral, and for either response mode, administration time is just 5 minutes. SDMT will be administered by the Investigator or a qualified designee.

Exemplary Assessments and Procedures for Evaluating Safety

Exemplary assessments and procedures for evaluating safety include:

Physical Examinations
   A complete physical examination will include, at a minimum, assessments of the Cardiovascular, Respiratory, Gastrointestinal and Neurological systems. Height (at Screening) and weight will also be measured and recorded. Weight will be measured and recorded at each visit where vital signs are recorded.
   A brief physical examination will include, at a minimum, assessments of the skin, lungs, cardiovascular system, and abdomen.
   Investigators should pay special attention to clinical signs related to previous serious illnesses.
   Any physical exam abnormality findings which are clinically significant, before the ICF signed will be captured on the Medical History eCRF. After the ICF is signed, new physical exam abnormality will be captured on the Adverse Event form.

Vital Signs
   Temperature, pulse rate, respiratory rate, and blood pressure will be assessed.
   Blood pressure and pulse measurements will be assessed with a completely automated device. Manual techniques will be used only if an automated device is not available.
   Blood pressure and pulse measurements should be preceded by at least 5 minutes of rest for the participant in a quiet setting without distractions (e.g., television, cell phones).
   Vital signs will be measured in a semi-supine position after 5 minutes rest and will include temperature, systolic and diastolic blood pressure, and pulse.

Electrocardiograms
  12-lead ECG will be obtained using an ECG machine that automatically calculates the heart rate and measures PR, QRS, QT, and QTc intervals.
  At each time point at which triplicate ECG are required, 3 individual ECG tracings should be obtained as closely as possible in succession, but no more than 2 minutes apart. The full set of triplicates should be completed in less than 4 minutes.
  The 12-lead ECG recordings will be obtained after 10 minutes of rest in a semisupine position.

Clinical Safety Laboratory Assessments
  Blood and urine samples will be collected for the clinical laboratory tests.
  Additional tests may be performed at any time during the study, as determined necessary by the Investigator or required by local regulations.
  The tests will be performed by the central or the local laboratory.
  Local laboratory results are only required when central laboratory results are not available in time for study intervention administration and/or response evaluation. If a local sample is required, it is important that the sample for central analysis is obtained at the same time. Additionally, if the local laboratory results are used to make a study intervention decision or response evaluation, the results must be entered in the CRF.
  The Investigator must review each laboratory report, document their review, and record any clinically relevant changes occurring during the study in the AE section of the CRF. The laboratory reports must be filed with the source documents.
  Laboratory/analyte results that could unblind the study will not be reported to investigative sites or other blinded personnel until the study has been unblinded.
  Pregnancy testing (serum or highly sensitive urine, as required by local regulations) will be conducted at monthly intervals during study intervention administration.
  Pregnancy testing (serum or highly sensitive urine, as required by local regulations) will be conducted at the end of relevant systemic exposure of the study intervention and correspond with the time frame for female participant contraception.

Immunoglobulin Levels
  Blood samples for Ig levels (IgM, IgA, IgG, and IgE) will be collected. Samples will be analyzed by the central laboratory selected by the Sponsor. Samples will be collected, labeled, processed, stored, and shipped according to the instructions in the Laboratory Manual. Results will not be disclosed to the sites, Sponsor, or representative, to avoid unblinding. However, the IDMC will have access to these data as applicable.

Chest X-Ray
  Posteroanterior CXRs will be performed. For participants in the OLE Period, a CXR will be performed at OLE Day 1. Participants who had a CXR performed for clinical reasons within 3 months prior to Day 1 do not need to have the CXR repeated. The CXR should show no evidence of active infective process, or any other clinically significant abnormalities. The overall evaluation (normal/abnormal) will be recorded on the eCRF, and if abnormal, the specific abnormality will be recorded. Abnormal evaluations will be judged as clinically significant or not clinically significant by the Investigator. The CXR will be performed and read locally.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated as described, and all changes that come within the meaning and range of equivalency of the claims are intended to be embraced therein.

The invention claimed is:

1. A method for treating multiple sclerosis, the method comprising:
  orally administering to a patient in need thereof, a compound of Formula I at a daily amount ranging from about 85 mg to about 95 mg, or a pharmaceutically acceptable salt thereof, wherein Formula I is represented by:

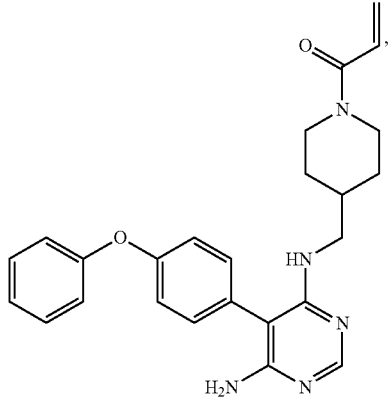

wherein the multiple sclerosis is relapsing multiple sclerosis, relapsing-remitting multiple sclerosis, secondary-progressive multiple sclerosis, or progressive-relapsing multiple sclerosis,
  wherein the compound of Formula I or the pharmaceutically acceptable salt thereof is administered twice per day, and
  wherein
  (i) the patient has consumed food within 1 hour prior to receiving said compound;
  (ii) the administering is performed at a time the patient consumes a meal; or
  (iii) the patient consumes a meal within 1 hour of receiving said compound.

2. The method of claim 1, wherein the patient is orally administered the compound of Formula I at the daily amount of about 90 mg, or the pharmaceutically acceptable salt thereof.

3. The method of claim 1, wherein the patient is orally administered twice per day a unit dosage, wherein each unit dosage contains the compound of Formula I in an amount of about 45 mg, or the pharmaceutically acceptable salt thereof.

4. The method of claim 1, wherein the patient has consumed food within 1 hour prior to receiving said compound.

5. The method of claim 1, wherein the patient has not consumed food within 1 hour prior to receiving said compound.

6. The method of claim 1, wherein the patient consumes a meal within 1 hour of receiving said compound.

7. The method of claim 1, wherein the administering is performed at a time the patient consumes a meal.

8. A method for treating multiple sclerosis, the method comprising:
orally administering to a patient in need thereof, two times per day a unit dosage containing a compound of Formula I in an amount ranging from about 25 mg to about 50 mg, or a pharmaceutically acceptable salt thereof, wherein Formula I is represented by:

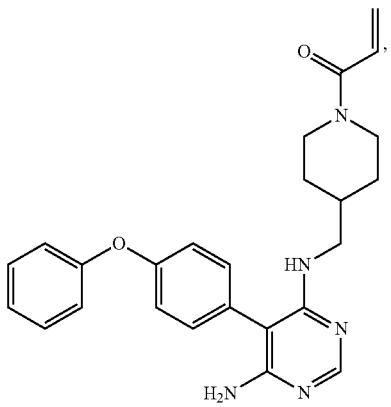

wherein the multiple sclerosis is relapsing multiple sclerosis, relapsing-remitting multiple sclerosis, secondary-progressive multiple sclerosis, or progressive-relapsing multiple sclerosis,
and wherein
(i) the patient has consumed food within 2 hours prior to receiving the unit dosage;
(ii) said administering is performed at the time the patient consumes a meal; or
(iii) the patient consumes food within 30 minutes of receiving the unit dosage.

9. The method of claim 8, wherein the unit dosage is administered to the patient in the form of two unit formulations containing the compound of Formula I, or the pharmaceutically acceptable salt thereof.

10. The method of claim 8, wherein the unit dosage is administered to the patient in the form of a single unit formulation containing the compound of Formula I, or the pharmaceutically acceptable salt thereof.

11. The method of claim 9, wherein the unit formulation(s) are a tablet or a capsule.

12. The method of claim 8, wherein there is at least 8 hours between administration of a first unit dosage and a second unit dosage to the patient on the same day.

13. The method of claim 8, wherein a first unit dosage is administered to the patient in the morning, and a second unit dosage is administered to the patient in the evening.

14. The method of claim 8, wherein the patient has consumed food within 2 hours prior to receiving the unit dosage.

15. The method of claim 8, wherein the patient has consumed food within 1 hour prior to receiving the unit dosage.

16. The method of claim 8, wherein the patient consumes food within 30 minutes of receiving the unit dosage.

17. A method for treating multiple sclerosis, the method comprising:
orally administering to a patient in need thereof, twice daily a unit dosage containing a compound of Formula I in an amount of about 45 mg or a pharmaceutically acceptable salt thereof, wherein the patient consumes a meal within about 1 hour of said administering, and Formula I is represented by:

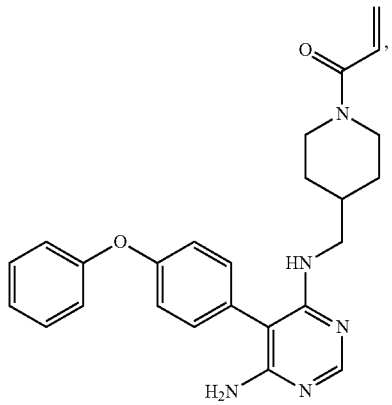 [SMILES: C=CC(=O)N1CCC(CNc2ncnc(N)c2-c2ccc(Oc3ccccc3)cc2)CC1]

wherein the multiple sclerosis is relapsing multiple sclerosis, relapsing-remitting multiple sclerosis, secondary-progressive multiple sclerosis, or progressive-relapsing multiple sclerosis.

18. The method of claim 17, wherein the unit dosage is administered to the patient in the form of one or more unit formulations containing the compound of Formula I, or the pharmaceutically acceptable salt thereof.

19. The method of claim 18, wherein the unit formulation(s) are a tablet or a capsule.

20. The method of claim 17, wherein said administering is performed at the time the patient consumes the meal.

21. The method of claim 17, wherein there is at least 8 hours between administration of a first unit dosage and a second unit dosage to the patient on the same day.

22. The method of claim 17, wherein a first unit dosage is administered to the patient in the morning, and a second unit dosage is administered to the patient in the evening.

23. The method of claim 17, wherein a first unit dosage is administered to the patient at the time the patient consumes a breakfast meal in the morning, and a second unit dosage is administered to the patient at the time the patient consumes a dinner meal in the evening.

24. The method of claim 17, wherein the multiple sclerosis is relapsing multiple sclerosis.

25. The method of claim 1, wherein the multiple sclerosis is relapsing multiple sclerosis.

26. The method of claim 1, wherein the patient experiences at least a 5% reduction in the number of gadolinium positive T1 magnetic resonance imaging lesions after receiving for a duration of 24 weeks the compound of Formula I or the pharmaceutically acceptable salt thereof.

27. The method of claim 8, wherein the patient experiences at least a 5% reduction in the number of gadolinium positive T1 magnetic resonance imaging lesions after receiving for a duration of 24 weeks the compound of Formula I or the pharmaceutically acceptable salt thereof.

28. The method of claim 17, wherein the patient experiences at least a 5% reduction in the number of gadolinium positive T1 magnetic resonance imaging lesions after receiving for a duration of 24 weeks the compound of Formula I or the pharmaceutically acceptable salt thereof.

29. The method of claim 1, which comprises treating multiple sclerosis with a twice daily unit dosage containing a compound of Formula I in an amount of about 45 mg or a pharmaceutically acceptable salt thereof, and wherein said administering is performed at the time the patient consumes a meal.

30. The method of claim 17, which comprises treating multiple sclerosis with a twice daily unit dosage containing a compound of Formula I in an amount of about 45 mg or a pharmaceutically acceptable salt thereof and wherein said administering is performed at the time the patient consumes a meal.

31. The method of claim 3, wherein the administering is performed at a time the patient consumes a meal.

32. The method of claim 29, wherein the administering is performed at a time the patient consumes a meal.

* * * * *